US012781169B2

(12) United States Patent
Skelley et al.

(10) Patent No.: US 12,781,169 B2
(45) Date of Patent: Nov. 3, 2026

(54) SYSTEMS AND METHODS FOR PARTICLE SEPARATION AND CONCENTRATION

(71) Applicant: ZEON CORPORATION, Tokyo (JP)

(72) Inventors: Alison Skelley, Richmond, VA (US); Khushroo Gandhi, Richmond, VA (US); Anthony Ward, Richmond, VA (US); Yasna Behmardi, Richmond, VA (US)

(73) Assignee: ZEON CORPORATION, Tokyo (JP)

( * ) Notice: Subject to any disclaimer, the term of this patent is extended or adjusted under 35 U.S.C. 154(b) by 651 days.

(21) Appl. No.: 18/261,748

(22) PCT Filed: Jan. 20, 2022

(86) PCT No.: PCT/US2022/013072

§ 371 (c)(1),
(2) Date: Jul. 17, 2023

(87) PCT Pub. No.: WO2022/159552

PCT Pub. Date: Jul. 28, 2022

(65) Prior Publication Data

US 2024/0101944 A1 Mar. 28, 2024

Related U.S. Application Data

(60) Provisional application No. 63/163,593, filed on Mar. 19, 2021, provisional application No. 63/140,196, (Continued)

(51) Int. Cl.

| | |
|---|---|
| ***C12M 3/00*** | (2006.01) |
| ***C12M 1/00*** | (2006.01) |

(Continued)

(52) U.S. Cl.

CPC ............ *C12M 23/42* (2013.01); *C12M 23/16* (2013.01); *C12M 27/00* (2013.01); *C12M 29/20* (2013.01); *C12M 41/48* (2013.01); *C12M 47/04* (2013.01)

(58) Field of Classification Search

CPC ...... C12M 23/42; C12M 23/16; C12M 27/00; C12M 29/20; C12M 41/48; C12M 47/04; C12M 47/02

See application file for complete search history.

(56) References Cited

U.S. PATENT DOCUMENTS

| | | | | |
|---|---|---|---|---|
| 2015/0225685 A1* | 8/2015 | Hirschel | C12M 23/00 | 435/235.1 |
| 2016/0024450 A1* | 1/2016 | Quick | C12M 45/09 | 435/379 |

(Continued)

FOREIGN PATENT DOCUMENTS

| | | | |
|---|---|---|---|
| CA | 2123695 A1 | 4/1994 | |
| CA | 2123695 C * | 9/2003 | F04B 43/1276 |

(Continued)

OTHER PUBLICATIONS

Jul. 17, 2025, Office Action issued by the IP Australia in the corresponding Australian Patent Application No. 2022209752.

(Continued)

*Primary Examiner* — Michael L Hobbs
(74) *Attorney, Agent, or Firm* — KENJA IP LAW PC

(57) ABSTRACT

Described herein are systems and methods for generating a product enriched in one or more target particles, comprising a cassette to which the one or more microfluidic cartridges are releasably coupled and supported, the cassette comprising (i) a plurality input containers releasably and fluidically coupled thereto, wherein at least one of the plurality of input containers comprises an incoming sample, (ii) a plurality of outlets having a plurality of output containers releasably and fluidically coupled thereto, (iii) one or more microfluidic cartridges for separating one or more target particles from the sample, and (iv) a plurality of fluidic channels extending between the plurality of inlets, the plurality of outlets, and the one or more microfluidic cartridges, wherein the cassette having the plurality of input containers, the plurality of output containers, and the one or more microfluidic cartridges coupled thereto, collectively provides a closed end-to-end sterile environment that enables inline continuous processing of the incoming sample without external manual handling or intervention, so as to generate a product that is enriched in one or more target particles and free of contamination.

23 Claims, 59 Drawing Sheets

Related U.S. Application Data filed on Jan. 21, 2021, provisional application No. 63/139,737, filed on Jan. 20, 2021.

(51) Int. Cl.

| | |
|---|---|
| ***C12M 1/02*** | (2006.01) |
| ***C12M 1/36*** | (2006.01) |
| ***C12M 3/06*** | (2006.01) |

(56) References Cited

U.S. PATENT DOCUMENTS

| | | | | |
|---|---|---|---|---|
| 2016/0047735 | A1 | 2/2016 | Grisham et al. | |
| 2016/0139012 | A1 | 5/2016 | D'Silva et al. | |
| 2017/0209864 | A1* | 7/2017 | Grisham | G01N 33/5094 |
| 2017/0248508 | A1 | 8/2017 | Ward et al. | |
| 2017/0333900 | A1 | 11/2017 | Grisham et al. | |
| 2018/0251723 | A1 | 9/2018 | Murthy | |
| 2019/0071639 | A1 | 3/2019 | Ward et al. | |
| 2020/0070167 | A1 | 3/2020 | Raillon et al. | |

FOREIGN PATENT DOCUMENTS

| | | | | |
|---|---|---|---|---|
| WO | WO-2007139742 | A1 * | 12/2007 | C12M 47/04 |
| WO | WO-2010025302 | A2 * | 3/2010 | B01L 3/50273 |
| WO | 2017035262 | A1 | 3/2017 | |
| WO | 2019222049 | A1 | 11/2019 | |

OTHER PUBLICATIONS

Mar. 28, 2025, the Extended European Search Report issued by the European Patent Office in the corresponding European Patent Application No. 22743149.1.

Han-Sheng Chuang et al., A diffusion-based cyclic particle extractor, Microfluidics and Nanofluidics, 2010, pp. 743-753, vol. 9.

Sep. 10, 2026, the Partial European Search Report issued by the European Patent Office in the corresponding European Patent Application No. 25225534.4.

Sep. 11, 2026, Communication pursuant to Article 94(3) EPC issued by the European Patent Office in the corresponding European Patent Application No. 22743149.1.

* cited by examiner

300

System Run Report

| | | | |
|---|---|---|---|
| **Run ID** | 4 | **Organization** | |
| **Protocol ID** | Separation/Wash | **Location Name** | |
| **Sample ID** | 4 | **Location Address** | |
| | | **Location City/State** | |

General Information

| | | | |
|---|---|---|---|
| **User ID** | administrator | **Run Status** | COMPLETE |
| **Curate SN** | 2 | **Start Time** | 01/20/2021 05:34 (05:34AM) |
| **Software Version** | 2.3 | **End Time** | 01/20/2021 06:31 (06:31AM) |
| | | **Time Zone** | UTC-08:00 |

Protocol Description Separation of WBCs from RBCs and PLTs and wash into new buffer/media

Results and Estimations

| | |
|---|---|
| **Sample Volume Input [mL]** | 130 |
| **Estimated Sample Processed weight [grams]** | 201.47 |
| **Final Product weight [grams]** | 198.31 |
| **Total Procedure Duration (HH:MM:SS)** | 00:56:50 |

Performance Metrics

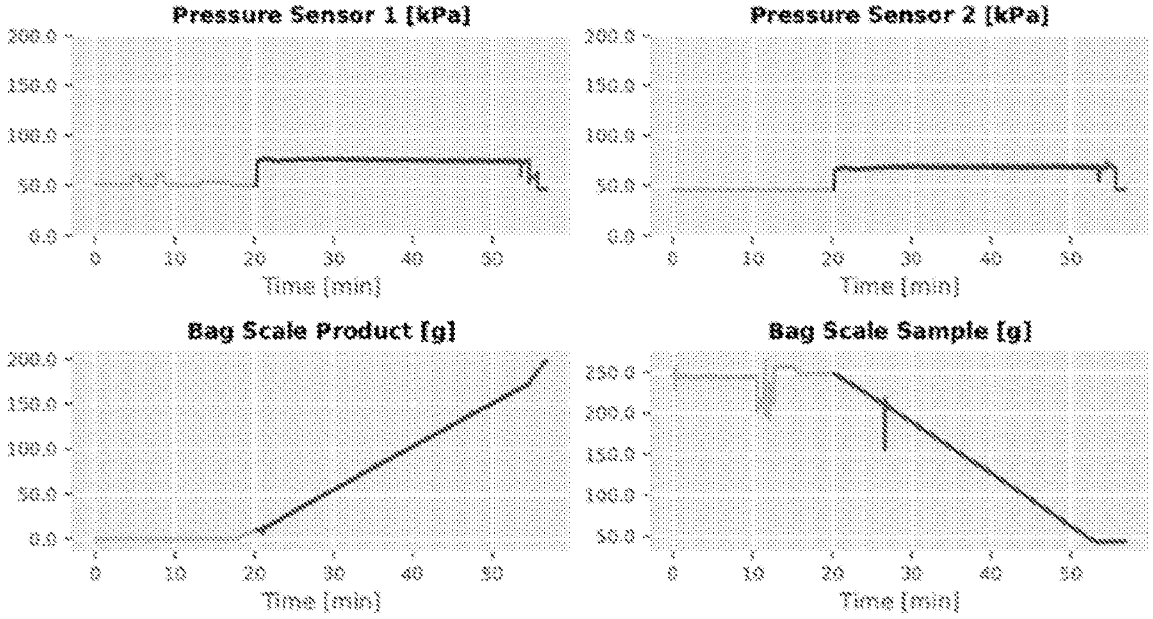

Signature ______________________ Date ______________________

*FIG. 5I*

Fold senescence and exhaustion of Ficoll vs. DLD value in CD 3+ T cells

| | Senescence CD57+/KLRG1+ | Exhausted CD57-/KLRG1+/PD1+/Tim3+ |
|---|---|---|
| CAR19 (- Sig domain) | 1.6 | 1.4 |
| CAR19 (+ Sig domain) | 2.7 | 3.4 |
| No CAR | 2.1 | 1.4 |
| Average | 2.1 | 2.1 |

FIG. 24

| Attribute | Ficoll | DLD | Results |
| --- | --- | --- | --- |
| Mass balance (cell recovery) | ++ | ++++ | WBC ~2.4x vs Ficoll (n-35/22)<br>T cells ~2.25x vs Ficoll (n=28/19). Can be as high as ~5x more |
| Product purity | + | +++ | RBC/WBC ~6x less vs Ficoll (n=31/21)<br>PLT/WBC 9x less vs Ficoll (n=31/21) |
| Transduction efficiency | + | +++ | GPB prepared cells stably uptake ~30% more Lentivirus |
| Time to dose | + | ++++ | 3 Days to achieve 2x10e9 cells with efficient viral construct<br>4 Days to with typical achieve 2x10e9 CAR+ T Cells |
| Product telomere length | + | ++++ | GPB recovers and delivers the full doubling potential of the sample as a result of more naïve T cells with longer telomeres |
| Effector memory conversion | ++ | +++ | In the presence of virus, Tcm bias is retained |
| Cell killing | ++ | ++ | Preliminary data shows that GPB prepared cells are effective killers |
| Cytokine release profile | + | +++ | GPB prepared cells produce a less pro-inflammatory state and cytokine profile consistent with good killing ability |
| Senescence and Anergic Profile | + | ++ | Senescence: ~2.0x # Exhausted Cells ~2.0x fewer than Ficoll at end of an expansion (13 days) |

FIG. 29

SYSTEMS AND METHODS FOR PARTICLE SEPARATION AND CONCENTRATION

CROSS-REFERENCE

This application claims the benefit of U.S. Provisional Application No. 63/139,737, filed Jan. 20, 2021, U.S. Provisional Application No. 63/140,196, filed Jan. 21, 2021, and U.S. Provisional Application No. 63/163,593, filed Mar. 19, 2021, each of which is incorporated herein by reference.

BACKGROUND

The separation of target cells from patient samples often requires the use of systems and methods that face several obstacles. The systems and methods may require the use of human intervention during the processing of a sample, affecting the sterility of the environment and of the product solution generated. Current systems and methods may struggle to achieve high throughput of a sample solution. They may also comprise moving parts throughout the separation process, introducing the possibility of further failure and contamination. Thus, the development of better performing devices and better methods for increasing the rate at which biological materials can be purified and increasing the sterility of the environment performing the separation process are of considerable interest.

SUMMARY

Described herein are certain cassettes, microfluidic devices, particle separation units, and components connecting the three for providing a system for improved separation time of target particles in an end-to-end closed system for improved sterility. Certain cassettes can have multiple input and output channels connecting a plurality of inputs to a plurality of outputs in a closed end-to-end environment providing for the continuous inline processing of an incoming sample, while maintaining a sterile operating environment with the need for little or no human intervention. The cassettes can also have multiple pathways for guiding an incoming sample, and multiple components for the gentle mixing and transportation of a sample solution with a plurality of other input and output solutions, preserving the sterility and viability of the sample solution.

The methods and systems described herein can produce therapeutic immune cell populations (including T cell populations), that exhibit beneficial properties compared to other methods of producing therapeutic immune cell populations. The advantages include greater expansion capability, increased ability to take up, integrate exogeneous nucleic acids and express proteins from lentivirus vectors, increased retention of advantageous cell populations such as naïve, resting, and unactivated or central memory T cells. The immune cells and T cells produced by the systems and methods described herein also possess a lower inflammatory phenotype as indicated by reduced levels of pro-inflammatory cytokines in culture, indicating that they have a reduced potential to contribute to cytokine release syndrome. Lower levels of pro-inflammatory cytokines in product T cells are significant as cytokine release syndrome is a major adverse event associated with T cell therapies (such as CART cells and recombinant T cell therapies), and is associated with the presence of differentiated and activated T cell subsets, such as, effector memory T cells (Tem) or effector T cells that regain expression of CD45RA (Temra), that release IL-1RA, IL-6, and IL-13. As shown herein cells produced by the systems and methods described also show lower release of key inflammatory cytokines that contribute to cytokine release syndrome.

Described herein in one aspect is a microfluidic cartridge for purifying target particles or target cells of a predetermined size from contaminants in a sample, the cartridge comprising a first and a second planar support the first and second planar support each having a top surface and a bottom surface, wherein the top surface of the first and/or second planar support comprises at least one embedded channel extending from one or more inlets to one or more outlets; the at least one embedded channel comprising a plurality of obstacles.

Described herein in one aspect is a particle separation unit comprising a plurality of components for the receiving, supporting, and/or operating the cassette, microfluidic cartridges, and input and output solutions.

In one aspect described herein is a system for generating a product enriched in one or more target particles, comprising: a cassette comprising (i) one or more cartridge ports, (ii) at least one inlet for receiving a sample, (iii) at least one outlet for outputting the product, and (iv) at least one recirculating pathway; and one or more microfluidic cartridges operably coupled to the one or more cartridge ports to establish fluidic communication with the cassette, such that the one or more microfluidic cartridges are used to separate the one or more target particles from the sample, the at least one recirculating pathway is used to recirculate the one or more target particles through the cassette to concentrate the one or more target particles into a predefined volume of media or to a predefined concentration, and the one or more microfluidic cartridges and the at least one recirculating pathway are operated in parallel to optimize a run time for generating the product. In certain embodiments, the one or more microfluidic cartridges and the at least one recirculating pathway are operated independently of each other. In certain embodiments, the one or more microfluidic cartridges are configured to separate the one or more target particles from the sample without affecting a recirculation process by the at least one recirculating pathway. In certain embodiments, the at least one recirculating pathway is configured to recirculate the one or more target particles through the cassette without affecting a separation process by the one or more microfluidic cartridges. In certain embodiments, the one or more microfluidic cartridges and the at least one recirculating pathway are individually controllable in real-time to achieve a desired concentration of the one or more target particles in the product. In certain embodiments, the at least one recirculating pathway extends between the at least one inlet and the at least one outlet. In certain embodiments, the at least one recirculating pathway is configured to recirculate the one or more target particles in a clockwise direction on the cassette. In certain embodiments, the at least one recirculating pathway is configured to recirculate the one or more target particles in a counter-clockwise direction on the cassette. In certain embodiments, the cassette further comprises a plurality of pathways for directing the sample into and out of the one or more microfluidic cartridges. In certain embodiments, the at least one recirculating pathway is provided separate from the plurality of pathways. In certain embodiments, the at least one recirculating pathway is adjoined or connected to one or more of the plurality of pathways. In certain embodiments, the system further comprises one or more mass sensors, and wherein the recirculation of the one or more target particles through the cassette is controlled based on one or more readings obtained from the one or more mass sensors.

In another aspect described herein is a system for generating a product enriched in one or more target particles, comprising: a cassette to which the one or more microfluidic cartridges are releasably coupled and supported, the cassette comprising a plurality of fluidic channels extending longitudinally and spaced apart on the cassette; and a plurality of pumps peristaltically coupled to the plurality of fluidic channels to control flow of fluidic content through the plurality of fluidic channels downstream to the one or more microfluidic cartridges for separation of one or more target particles from the sample, without any moving parts from the pumps directly contacting the fluidic content during its flow. In certain embodiments, the plurality of fluidic channels comprises flexible tubing. In certain embodiments, each of the plurality of pumps comprises a set of pump heads that are peristaltically coupled to each subset of the plurality of fluidic channels. In certain embodiments, the set of pump heads in each pump comprises two or more pump heads. In certain embodiments, the two or more pump heads comprises two or more sets of rollers. In certain embodiments, each subset of the plurality of fluidic channels comprises two or more fluidic channels. In certain embodiments, the fluidic content comprises the sample, a media solution, a diluent, and waste that is generated by the one or more microfluidic cartridges after the one or more target particles have been separated from the sample. In certain embodiments, the fluidic content further comprises a priming solution. In certain embodiments, the fluidic content further comprises a recirculated solution comprising a concentrated amount of the one or more target particles. In certain embodiments, the plurality of pumps comprises a first pump for controlling a flow of the sample, a second pump for controlling a flow of the media solution, a third pump for controlling a flow of the diluent, and a fourth pump for controlling a flow of the waste. In certain embodiments, the plurality of pumps are individually controllable to modulate relative flowrates between the sample, the media solution, the diluent, and the waste. In certain embodiments, the set of pump heads in each pump are configured to actuate out-of-phase relative to each other. In certain embodiments, the set of pump heads in each pump actuate out-of-phase by less than or equal to about 180 degrees. In certain embodiments, the set of pump heads in each pump have a fixed motion relative to each other. In certain embodiments, the fixed motion comprises the set of pump heads in each pump moving at a same rate and in a same direction relative to each other. In certain embodiments, for each pump and each subset of fluidic channels, the fluidic content transported by the set of pump heads is combined together at an outlet of each subset of fluidic channels into a single fluid path. In certain embodiments, a pulsatility of each pump is reduced by moving the set of pump heads out of phase. In certain embodiments, the plurality of pumps are individually controllable to (a) control a ratio of an amount of the waste relative to an amount of the sample, (b) control a ratio of an amount of the sample relative to an amount of the diluent, or (c) adjust a dilution factor. In certain embodiments, the plurality of pumps are individually controllable to be in phase or out of phase relative to each other. In certain embodiments, the plurality of pumps are individually controllable to achieve a same flow rate, different flow rates, a same flow direction, or different flow directions. In certain embodiments, the plurality of pumps are individually controllable to adjust the flow of the fluidic content in real-time as the one or more microfluidic cartridges are separating out the one or more target particles from the sample. In certain embodiments, the plurality of pumps are individually controllable to enable a desired concentration of the one or more target particles in the product. In certain embodiments, the plurality of pumps comprises peristaltic pumps. In certain embodiments, the plurality of pumps comprises at least 2, 3, 4, 5, 6, 7, or 8 pumps.

In another aspect described herein is a system for generating a product enriched in one or more target particles, comprising: one or more microfluidic cartridges that are configured to separate the one or more target particles from a sample; one or more sensors for detecting a presence of air bubbles in the sample or another solution; one or more controllable valves; and a cassette to which the one or more microfluidic cartridges are releasably coupled and supported, the cassette comprising one or more bypass channels downstream of the one or more controllable valves for diverting a portion of the sample or the another solution having the air bubbles away from the one or more microfluidic cartridges, based on a detection of the presence of the air bubbles by the one or more sensors. In certain embodiments, the one or more sensors are used for detecting the presence of the air bubbles prior to circulating the sample into the one or more microfluidic cartridges. In certain embodiments, the system is configured to generate one or more alerts upon the one or more sensors detecting the presence of air bubbles in the sample or the another solution. In certain embodiments, the one or more sensors and the one or more bypass channels work in concert to prevent the air bubbles from entering and reducing an efficiency of the one or more microfluidic cartridges. In certain embodiments, the one or more sensors and the one or more bypass channels work in concert to reduce or eliminate contamination in the product.

Also described herein is a system for generating a product enriched in one or more target particles, comprising: one or more microfluidic cartridges that are configured to separate the one or more target particles from a sample; a cassette to which the one or more microfluidic cartridges are releasably coupled and supported; and at least one degassing unit for removing dissolved gases and preventing bubble formation prior to the sample being circulated through the one or more microfluidic cartridges. In certain embodiments, the at least one degassing unit is integrated onto the cassette. In certain embodiments, the at least one degassing unit is fabricated as part of the cassette. In certain embodiments, the at least one degassing unit is located on the cassette in proximity to the one or more microfluidic cartridges. In certain embodiments, the at least one degassing unit is in fluidic communication with a plurality of pathways leading into the one or more microfluidic cartridges. In certain embodiments, the system further comprises a panel operably coupled to the cassette, and wherein the at least one degassing unit is integrated onto the panel. In some embodiments, the degassing unit is a vacuum-based degassing unit. In some embodiments, an integrated vacuum pump is connected to the vacuum degassing unit, which applies vacuum to a vacuum chamber of the vacuum degassing unit. In some embodiments, fluid entering the degassing unit is passed through tubing made from a porous membrane that separates the fluidic path of the degassing unit from the vacuum chamber of the degassing unit. In some embodiments, dissolved gasses in the fluid contained in the fluidic path of the degassing unit pass through the membrane while the fluid does not, thereby removing the dissolved gas from the fluid into the vacuum of the vacuum chamber.

In another aspect described herein is a system for generating a product enriched in one or more target particles, comprising: a cassette to which the one or more microfluidic cartridges are releasably coupled and supported, the cassette comprising (i) a plurality of inlets having a plurality of input containers releasably and fluidically coupled thereto, wherein at least one of the plurality of input containers comprises an incoming sample, (ii) a plurality of outlets having a plurality of output containers releasably and fluidically coupled thereto, (iii) one or more microfluidic cartridges for separating one or more target particles from the sample, and (iv) a plurality of fluidic channels extending between the plurality of inlets, the plurality of outlets, and the one or more microfluidic cartridges, wherein the cassette having the plurality of input containers, the plurality of output containers, and the one or more microfluidic cartridges coupled thereto, collectively provides a closed end-to-end sterile environment that enables inline continuous processing of the incoming sample without external manual handling or intervention, so as to generate a product that is enriched in one or more target particles and free of contamination. In certain embodiments, the plurality of inlets and the plurality of input containers are releasably and fluidically coupled using a plurality of sterile coupling mechanisms. In certain embodiments, the plurality of sterile coupling mechanisms comprises at least one sterile spike and at least one spike port. In certain embodiments, the plurality of sterile coupling mechanisms comprises at least one sterile Luer fitting. In certain embodiments, the plurality of sterile coupling mechanisms comprises at least one sterile tubing weld. In certain embodiments, the plurality of sterile coupling mechanisms comprises at least one sterile quick connect fitting. In certain embodiments, the product is collected in at least one of the plurality of output containers. In certain embodiments, the product is collected in at least one of the plurality of output containers without exposing the product to an external non-sterile environment. In certain embodiments, the product is collected in at least one of the plurality of output containers without exposing the product to an external non-sterile environment. In certain embodiments, the sample is input from the at least one of the plurality of input containers into the cassette without exposing the sample to an external non-sterile environment. In certain embodiments, the system does not require any intermediary reagent to be externally added from outside of the closed end-to-end sterile environment during the inline continuous processing of the incoming sample. In certain embodiments, the system does not require any intermediary byproduct to be removed outside of the closed end-to-end sterile environment during the inline continuous processing of the incoming sample. In certain embodiments, the sample has a volume of at least about 200 mL, and the system is configured to process the sample to generate in less than 1 hour the product being enriched with at least about 70% recovery of the one or more target particles. In certain embodiments, the system is configured to process the sample at a rate equal to or greater than about 300 mL/hr.

Also described herein is a system for generating a product enriched in one or more target particles, comprising: one or more microfluidic cartridges that are configured to separate the one or more target particles from a sample; and a cassette to which the one or more microfluidic cartridges are releasably coupled and supported, the cassette comprising a mixer that is configured to mix the sample with a diluent inline on the cassette without using any moving parts, prior to the sample being circulated through the one or more microfluidic cartridges. In certain embodiments, the mixer comprises a first fluidic channel for the sample and a second fluidic channel for the diluent. In certain embodiments, the first fluidic channel and the second fluidic channel converge to permit mixing of the sample and the diluent. In certain embodiments, the first fluidic channel and the second fluidic channel comprise a plurality of structural elements for facilitating inline mixing of the sample and the diluent.

Also described herein is a method comprising: (a) providing a system comprising a cassette to which one or more microfluidic cartridges are releasably coupled and supported; (b) priming the cassette by flowing a priming solution through the system; (c) processing a sample by flowing the sample through the system and using the one or more microfluidic cartridges to separate one or more target particles from the system; (d) collecting a product comprising the one or more target particles that have been separated from the sample, wherein the sample has a volume of at least about 40 mL, the product is enriched with at least about 70% recovery of the one or more target particles, and (b) through (d) are completed continuously inline in a closed sterile environment in less than or equal to about 1 hour. In certain embodiments, (b) is completed in less than or equal to about 20 minutes. In certain embodiments, (c) and (d) are completed in less than or equal to about 40 minutes. In certain embodiments, the cassette and the one or more microfluidic cartridges are configured for single use. In certain embodiments, (b) permits the cassette to be reusable for multiple use. In certain embodiments, (b) permits the one or more microfluidic cartridges to be reusable for multiple use. In certain embodiments, the sample is a human sample. In certain embodiments, the sample comprises a blood-related product. In certain embodiments, the blood-related product comprises an apheresis product. In certain embodiments, the apheresis product is a leukapheresis product. In certain embodiments, the one or more target particles that have been separated from the sample comprise cells. In certain embodiments, the cells are human cells. In certain embodiments, the cells are greater than about 90% viable upon recovery. In certain embodiments, the cells comprise peripheral blood mononuclear cells. In certain embodiments, the cells comprise CD3+ T cells. In certain embodiments, the T cells exhibit a naïve or central memory phenotype. In certain embodiments, the method further comprises culturing or expanding the cells in vitro. In certain embodiments, the method further comprises rendering the cells transgenic with an exogenous nucleic acid. In certain embodiments, the exogenous nucleic acid encodes a chimeric antigen receptor or a recombinant T cell receptor. In certain embodiments, the sample has a volume of at least about 300 mL. In certain embodiments, the sample has a volume of at least about 100 mL. In certain embodiments, the product is enriched with at least about 80% of the one or more target particles. In certain embodiments, the product is enriched with at least about 90% of the one or more target particles. In certain embodiments, the product is enriched with at least about 95% of the one or more target particles. In certain embodiments, the sample has a volume of at least about 100 mL. In certain embodiments, the sample has a volume of at least about 150 mL. In certain embodiments, the sample has a volume of at least about 200 mL.

Also described herein is a method comprising: displaying a graphical user interface (GUI) on a computer, the GUI comprising (i) a control panel and (ii) a visual representation of a system, the system comprising (a) a cassette to which one or more microfluidic cartridges are releasably coupled and supported, and (b) a plurality of components for facilitating fluidic transport and process control; receiving user input for a run protocol entered via the control panel; activating the run protocol on the system to process a sample by using the one or more microfluidic cartridges to separate one or more target particles from the sample; and displaying substantially in real-time a progress or status as the system is processing the sample, wherein the progress or status is depicted by graphical changes to the visual representation of the system. In certain embodiments, the plurality of components comprises flow channels, valves, pressure sensors, and pumps. In certain embodiments, the plurality of components further comprises one or more bubble sensors and at least one degassing unit. In certain embodiments, the graphical changes comprise an on/off status of one or more of the plurality of components. In certain embodiments, the graphical changes comprise a fluidic flow of the sample or other media through the cassette and the one or more microfluidic cartridges. In certain embodiments, the method further comprises generating one or more notifications on the GUI that indicate that the system is processing the sample in accordance with the run protocol. In certain embodiments, the method further comprises generating one or more notifications on the GUI that indicate that the system is experiencing one or more deviations from the run protocol as the sample is being processed. In certain embodiments, the method further comprises generating one or more options on the GUI for a user to rectify the one or more deviations. In certain embodiments, the method further comprises automatically reducing a pressure and a flow rate of the sample upon detection of the one or more deviations from the run protocol. In certain embodiments, the method further comprises generating a report comprising a plurality of run metrics when the system has completed processing the sample. In certain embodiments, the GUI allows a user to view a status and control an operation of one or more of the plurality of components substantially in real-time as the system processing the sample.

The systems and methods described herein in certain embodiments, are for and directed to uses in the enrichment of cells for cell therapies (e.g., CART-cell therapies, cell based immune therapies, and stem cell therapies. The source of the cells for enrichment, isolation, or separation is blood related products that are obtained from a patient to be treated or an HLA matched donor. In certain embodiments, the sample is a human sample. In certain embodiments, the sample comprises a blood-related product. In certain embodiments, the blood-related product comprises an apheresis product. In certain embodiments, the apheresis product is a leukapheresis product. In certain embodiments, the one or more target particles that have been separated from the sample comprise cells. In certain embodiments, the cells are human cells. In certain embodiments, the cells are greater than about 90% viable upon recovery. In certain embodiments, the cells comprise peripheral blood mononuclear cells. In certain embodiments, the cells are greater than about 80%, 85%, 90%, or 95% of the peripheral blood mononuclear cells are recovered from a starting sample. In certain embodiments, the cells comprise CD3+ T cells. In certain embodiments, the T cells exhibit a naïve or central memory phenotype. In certain embodiments, the method further comprises culturing or expanding the cells in vitro. In certain embodiments, the method further comprises rendering the cells transgenic with an exogenous nucleic acid. In certain embodiments, the exogenous nucleic acid encodes a chimeric antigen receptor or a recombinant T cell receptor. In certain embodiments, the sample has a volume of at least about 300 mL. In certain embodiments, the sample has a volume of at least about 100 mL. In certain embodiments, the sample has a volume of at least about 100 mL. In certain embodiments, the sample has a volume of at least about 150 mL. In certain embodiments, the sample has a volume of at least about 200 mL.

In certain embodiments leukocytes are enriched to at least about 85% or greater of a resulting product. In certain embodiments leukocytes are enriched to at least about 90% or greater of a resulting product. In certain embodiments leukocytes are enriched to at least about 85% or greater of a resulting product. In certain embodiments at least about $2\times10^9$ leukocytes are obtained from a leukopak of at least about 200 mL. In certain embodiments at least about $2\times10^9$ leukocytes are obtained from a leukopak of at least about 300 mL. In certain embodiments at least about $2\times10^9$ leukocytes are obtained from a 100 mL leukopak. In certain embodiments at least about $5\times10^9$ leukocytes are obtained from a leukopak of at least about 200 mL. In certain embodiments at least about $5\times10^9$ leukocytes are obtained from a leukopak of at least about 300 mL. In certain embodiments at least about $5\times10^9$ leukocytes are obtained from a leukopak of at least about 100 mL.

In certain embodiments enriched leukocytes possess a telomere length of at least about 2 kilobases. In certain embodiments enriched leukocytes possess a telomere length of at least about 3 kilobases. In certain embodiments enriched leukocytes possess a telomere length of at least about 5 kilobases.

In certain embodiments at least about $4\times10^8$ naïve T cells are obtained from a leukopak of at least about 200 mL. In certain embodiments at least about $4\times10^8$ naïve T cells are obtained from a leukopak of at least about 300 mL. In certain embodiments at least about $4\times10^8$ naïve T cells are obtained from a leukopak of at least about 100 mL. In certain embodiments at least about $5\times10^8$ central memory T cells are obtained from a leukopak of at least about 200 mL. In certain embodiments at least about $5\times10^8$ central memory T cells are obtained from a leukopak of at least about 300 mL. In certain cases, at least about $5\times10^8$ central memory T cells are obtained from a leukopak of at least about 100 mL.

In certain embodiments a product comprising at least about 1.5-fold, about 2.5-fold, or about 5-fold more leukocytes is obtained as compared to the number of leukocytes obtained by using a density gradient centrifugation method. In certain embodiments a product comprising CD 3+ cells, CD 45+ cells, CD 4+ cells, CD4+ naïve cells, CD 4+ memory cells, CD 4+ effector cells, CD 8+ cells, CD 8+ naïve cells, CD 8+ effector cells, CD 8+ memory cells, memory cells, effector cells, naïve cells, Temra cells, or any combination thereof is obtained. In certain embodiments a product comprising at least about 1.5-fold, about 2.5-fold, or about 5-fold more CD 45+ cells is obtained as compared to those obtained by using a density gradient centrifugation method. In certain embodiments a product comprising at least about 1.5-fold, about 2.5-fold, or about 5-fold more CD 3+ cells is obtained as compared to those obtained by using a density gradient centrifugation method.

In some embodiments, the system or method further comprises removing one or more target particles from the sample. In some aspects, the target particles are cells. In some aspects, the cells are red blood cells or platelets. In some aspects, at least about 95% of the red blood cells are removed from the sample. In some aspects, at least 95% of the platelets are removed from the sample.

In certain embodiments a product is produced that comprises a mixture of red blood cells and leukocytes at a ratio less than 2.5:1, 1.5:1, or 0.7:1. In certain embodiments a product is produced that comprises a mixture of platelets and leukocytes at a ratio less than 9:1, 5:1, 3:1, 1.1:1. In certain embodiments a product is produced that comprises at least about 1.5-fold, about 2.5-fold, or about 5-fold more CD 4+ cells are obtained as compared to those obtained by using a density gradient centrifugation method. In certain embodiments a product is produced that comprises at least about 1.5-fold, about 2.5-fold, or about 5-fold more CD 8+ cells are obtained as compared to those obtained by using a density gradient centrifugation method. In certain embodiments a product is produced that comprises at least about 1.5-fold, about 2.5-fold, about 5-fold more naïve CD 4+ cells are obtained as compared to those obtained by using a density gradient centrifugation method. In certain embodiments a product is produced that comprises at least about 1.5-fold, about 2.5-fold, or about 2.5-fold more memory CD 4+ cells are obtained as compared to those obtained by using a density gradient centrifugation method. In certain embodiments a product is produced that comprises at least about 1.5-fold, about 2.5-fold, or about 2.5-fold more effector CD 4+ cells are obtained as compared to those obtained by using a density gradient centrifugation method. In certain embodiments a product is produced that comprises at least about 1.5-fold, about 2.5-fold, about 5-fold more naïve CD 8+ cells are obtained as compared to those obtained by using a density gradient centrifugation method. In certain embodiments a product is produced that comprises at least about 1.5-fold, about 2.5-fold, or about 5-fold more memory CD 8+ cells are obtained as compared to those obtained by using a density gradient centrifugation method. In certain embodiments a product is produced that comprises at least about 1.5-fold, about 2.5-fold, about 5-fold more effector CD 8+ cells are obtained as compared to those obtained by using a density gradient centrifugation method. In certain embodiments a product is produced that comprises at least about 1.5-fold, about 2.5-fold, or about 5-fold more leukocytes are obtained as compared to the number of leukocytes obtained by using a density gradient centrifugation method. In certain embodiments a product is produced that comprises at least 1.5-fold, about 2.5-fold, or about 3-fold fewer red blood cells than that of a product obtained by using a density gradient centrifugation method. In certain embodiments a product is produced that comprises at least 3-fold or 10-fold fewer platelets than that of a product obtained by using a density gradient centrifugation method.

In some aspects, the methods and systems disclosed herein produce a cell population that exhibits an increase in one or more biological properties when compared to a population of cells produced by a density gradient centrifugation method wherein the one more biological properties are selected from the list consisting of: ability to readily integrate a lentiviral vector, ability to expand in culture, ability to retain T cell memory composition while in cell culture, receptivity to viral transduction, average telomere length, ability to retain a relative population of less differentiated naïve and central memory cells, functional killing capacity, IFN gamma expression, GM-CSF expression, TNF-a expression, and viability. In some embodiments, the population of cells exhibits at least about 25% increase in ability to readily integrate a lentiviral vector when compared to a population of cells produced by a density gradient centrifugation method. In some embodiments, the population of cells exhibits an increased ability to expand in culture, wherein the cells are expanded before or after being genetically modified when compared to a population of cells produced by a density gradient centrifugation method. In some embodiments, the population of cells exhibits at least about 1.5-fold increased ability to expand in culture when compared to a population of cells produced by a density gradient centrifugation method. In some embodiments, the population of cells exhibits an increased ability to retain T cell memory composition while in cell culture comprising retaining about the same T cell memory composition after at least 9 days in culture when compared to a population of cells produced by a density gradient centrifugation method. In some embodiments, the population of cells exhibits at least 30% increase in receptivity to viral transduction when compared to a population of cells produced by a density gradient centrifugation In some embodiments, the population of cells exhibits at least 30% increase in telomere length when compared to a population of cells produced by a density gradient centrifugation method.

In some embodiments, the population of cells exhibits an increased ability to retain a relative population of less differentiated naïve and central memory cells while in cell culture comprising retaining about the same relative population of less differentiated naïve and central memory cells after at least 9 days in culture when compared to a population of cells produced by a density gradient centrifugation method. In some embodiments, the population of cells exhibits at least 30% increase in functional killing capacity when compared to a population of cells produced by a density gradient centrifugation method. In some embodiments, the population of cells exhibits at least 2-fold increase in IFN gamma expression after 9 days in culture when compared to a population of cells produced by a density gradient centrifugation method. In some embodiments, the population of cells exhibits at least 1.5-fold increase in GM-CSF expression after 9 days in culture when compared to a population of cells produced by a density gradient centrifugation method. In some embodiments, the population of cells exhibits at least 10% increase in TNF-a expression after 9 days in culture when compared to a population of cells produced by a density gradient centrifugation method. In some embodiments, the population of cells exhibits at least 10% increase in viability when compared to a population of cells produced by a density gradient centrifugation method.

In some aspects, the methods and systems disclosed herein produce a cell population that exhibits a decrease in one or more biological properties when compared to a population of cells produced by a density gradient centrifugation method wherein the one more biological properties are selected from the list consisting of: time required to expand in culture to produce a single therapeutic dose equivalent of cells, time required to express a gene delivered by a vector, relative population of effector or Temra cells, IL-1Ra expression, IL-6 expression, IL-13 expression, MCP-1 expression, PD1 and Tim3 co-expression, cell senescence or exhaustion, propensity to trigger cytokine release syndrome, and time in culture required before being delivered to a patient. In some embodiments, the population of cells exhibits at least decrease of 3 days of time required to expand in culture to produce a single therapeutic dose equivalent of cells when compared to a population of cells produced by a density gradient centrifugation method. In some embodiments, the population of cells exhibits at least decrease of 1 day of time required to express a gene delivered by a vector when compared to a population of cells produced by a density gradient centrifugation method. In some embodiments, the population of cells exhibits at least 10% decrease in relative population of effector or Temra cells when compared to a population of cells produced by a density gradient centrifugation method. In some embodiments, the population of cells exhibits at least 40% decrease in IL-1Ra expression after 13 days in culture when compared to a population of cells produced by a density gradient centrifugation method. In some embodiments, the population of cells exhibits at least 60% decrease in IL-6 expression after 13 days in culture when compared to a population of cells produced by a density gradient centrifugation method. In some embodiments, the population of cells exhibits at least 10% decrease of IL-13 expression when compared to a population of cells produced by a density gradient centrifugation method. In some embodiments, the population of cells exhibits at least 20% decrease of MCP-1 expression when compared to a population of cells produced by a density gradient centrifugation method. In some embodiments, the population of cells exhibits at least 50% decrease in PD1 and Tim3 co-expression when compared to a population of cells produced by a density gradient centrifugation method. In some embodiments, the population of cells exhibits at least 50% decrease in cell senescence or exhaustion when compared to a population of cells produced by a density gradient centrifugation method. In some embodiments, the population of cells exhibits at least 20% decreased propensity to trigger cytokine release syndrome when compared to a population of cells produced by a density gradient centrifugation method. In some embodiments, the population of cells exhibits at least 3 day decrease in time in culture required before being delivered to a patient. In some embodiments, the exhibited increase or decrease of one or more biological properties when compared to a population of cells produced by a density gradient centrifugation method is apparent at least at about 0, 3, 6, 9, 13, or 16 days after being produced.

INCORPORATION BY REFERENCE

All publications, patents, and patent applications mentioned in this specification are herein incorporated by reference to the same extent as if each individual publication, patent, or patent application was specifically and individually indicated to be incorporated by reference. Furthermore, each of U.S. 62/954,478, U.S. 62/875,942, PCT/US2020/066812, and PCT/US2020/042634 is incorporated by reference herein in its entirety. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 5I-5J illustrate example data reports produced by a system in accordance with some embodiments.

(FIG. 9A) Shows greater recovery of central memory and naïve T cells. (FIG. 9B) Shows greater recovery of CD4+ T cell subsets

FIG. 24 illustrates that cell populations enriched according to the systems and methods herein show two-fold reduced senescence and exhaustion with significantly less PD1/Tim3 co-expression at day 13 of culture, and fewer cells entering TEMRA state (T effector memory cells that express CD45Ra) compared to Ficoll preparations.

FIG. 29 summarizes various advantages of cell populations enriched according to the systems and methods herein compared to Ficoll preparations.

DETAILED DESCRIPTION

Figure 1:
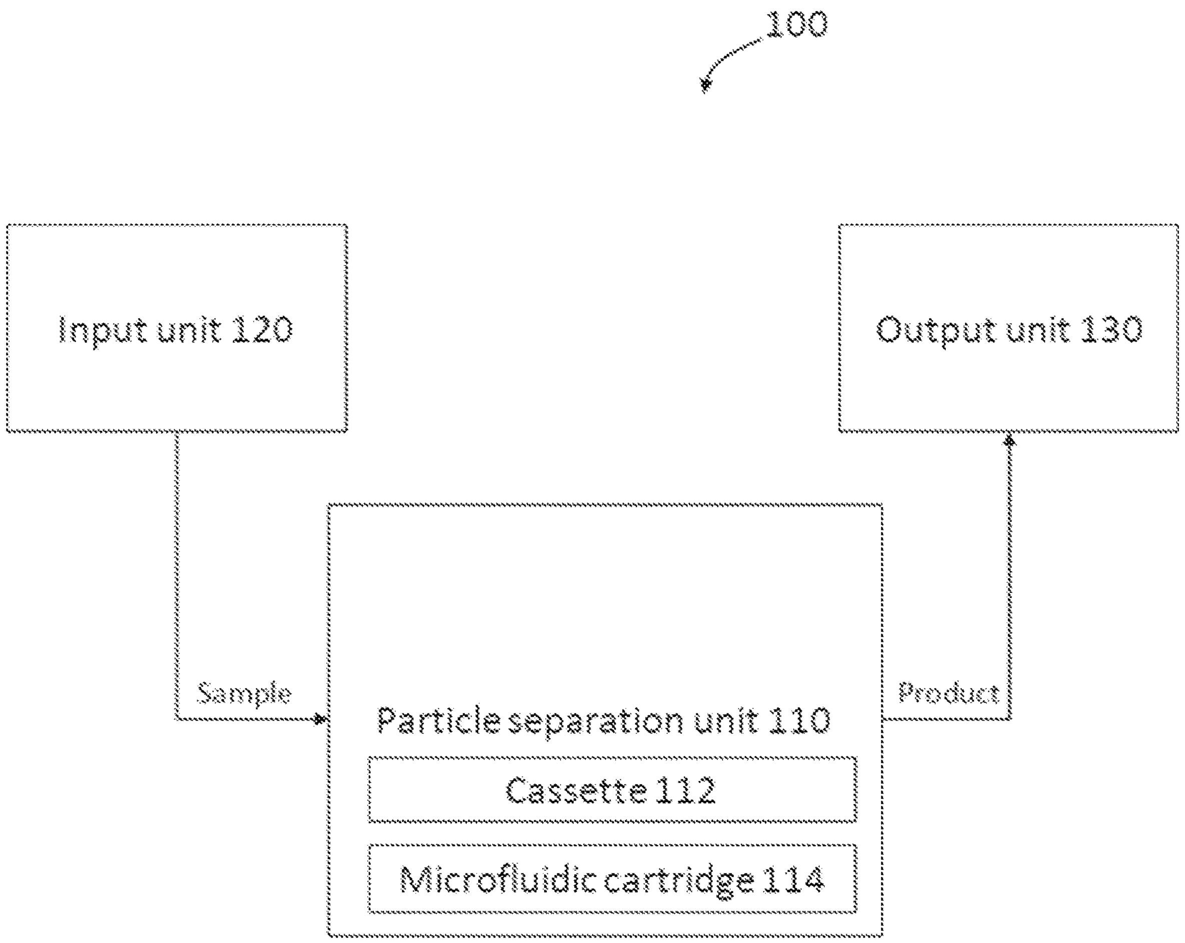
FIG. 1 schematically illustrates a system for processing an inlet solution and generating an outlet solution that is enriched in one or more target particles in accordance with some embodiments.

The present invention is primarily concerned with systems and methods for separating target particles. The text herein describes and relates to the making and the use of the systems and methods for carrying out separations involving biological materials.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Definitions

Apheresis: As used herein this term refers to a procedure in which blood from a patient or donor is separated into its components, e.g., white blood cells, platelets and red blood cells. An "apheresis sample" is the product that is the end result of this procedure. More specific terms are "plateletpheresis" (referring to the separation of platelets) and "leukapheresis" (referring to the separation of leukocytes). In this context, the term "separation" refers to the obtaining of a product that is enriched in a particular component compared to whole blood or other starting material and does not mean that absolute purity has been attained.

Sample: The term "sample," as used herein, generally refers to any sample containing or suspected of containing a nucleic acid molecule or cells. For example, a sample can be a biological sample containing one or more nucleic acid molecules or cells. The biological sample can be obtained (e.g., extracted or isolated) from or include blood (e.g., whole blood), plasma, serum, urine, saliva, mucosal excretions, sputum, stool and tears. The sample may contain blood, a blood-related product (such as a leukapheresis or apheresis product) also containing an anti-coagulant (e.g., EDTA, EGTA, heparin, citrate, ACD-A, or a thrombin inhibitor). The sample can be a human sample. The biological sample can be a fluid or tissue sample (e.g., skin sample). In some examples, the sample is obtained from a cell-free bodily fluid, such as plasma.

In some examples, the sample can include circulating tumor cells. In some examples, the sample is an environmental sample (e.g., soil, waste, ambient air and etc.), industrial sample (e.g., samples from any industrial processes), and food samples (e.g., dairy products, vegetable products, and meat products). The sample may be processed prior to loading into the microfluidic device. The sample may suitably be an apheresis product or a leukapheresis product (e.g., leukopak).

Target cells: As used herein "target cells" are the cells that various procedures described herein require or are designed to purify, collect, engineer etc. What the specific cells are will depend on the context in which the term is used. For example, if the objective of a procedure is to isolate a particular kind of stem cell, that cell would be the target cell of the procedure.

Isolate or purify: Unless otherwise indicated, these terms, as used herein, are synonymous and refer to the enrichment of a desired product relative to unwanted material. The terms do not necessarily mean that the product is completely isolated or completely pure. For example, if a starting sample had a target cell that constituted 2% of the cells in a sample, and a procedure was performed that resulted in a composition in which the target cell was 60% of the cells present, the procedure would have succeeded in isolating or purifying the target cell.

Obstacle array: As used herein, this term describes an ordered array of obstacles that are disposed in a flow channel through which a cell or particle-bearing fluid can be passed. An obstacle array comprises a plurality of obstacles arranged in a column (along the path of fluid flow). Gaps are formed between the obstacles (along the path of the fluid flow) that allows the passage of cells or other particles. Such arrays or columns can be arranged into one or more repeating rows (perpendicular to the path of fluid flow).

As used herein, the term "Deterministic Lateral Displacement" or "DLD" refers to a process in which particles are deflected on a path through an array, deterministically, based on their size in relation to some of the array parameters. This process can be used to separate cells, which is generally the context in which it is discussed herein. However, it is important to recognize that DLD can also be used to concentrate cells and for buffer exchange. Processes are generally described herein in terms of continuous flow DC conditions; i.e., bulk fluid flow in only a single direction). However, DLD can also work under oscillatory flow (AC conditions; i.e., bulk fluid flow alternating between two directions).

Critical size: The "critical size," "critical diameter" or "predetermined size" of particles passing through an obstacle array describes the size limit of particles that are able to follow the laminar flow of fluid. Particles larger than the critical size can be 'bumped' from the flow path of the fluid while particles having sizes lower than the critical size (or predetermined size) will not be displaced.

Fluid flow: The terms "fluid flow" and "bulk fluid flow" as used herein in connection with microfluidic cartridges refer to the macroscopic movement of fluid in a general direction across an obstacle array. These terms do not take into account the temporary displacements of fluid streams for fluid to move around an obstacle in order for the fluid to continue to move in the general direction.

Tilt angle F: In an obstacle array device, the tilt angle is the angle between the direction of bulk fluid flow and the direction defined by alignment of rows of sequential obstacles in the array.

Array Direction: In an obstacle array device, the "array direction" is a direction defined by the alignment of rows of sequential obstacles in the array. A particle is "deflected" in an obstacle array if, upon passing through a gap and encountering a downstream obstacle, the particle's overall trajectory follows the array direction of the obstacle array (i.e., travels at the tilt angle F relative to bulk fluid flow). A particle is not bumped if its overall trajectory follows the direction of bulk fluid flow under those circumstances.

About: As used herein the term about refers to that number plus or minus 10%, 9%, 8%, 7%, 6%, 5%, 4%, 3%, 2%, 1% of that number.

Real-time: As used herein, "real-time" generally refers to a response time that does not appear to be of substantial delay to a user as graphical elements are pushed to the user via a user interface. In some embodiments, a response time may be associated with processing of data, such as by a computer processor, and may be less than 5 seconds, 4 seconds, 3 seconds, 2 seconds, 1 second, tenth of a second, hundredth of a second, a millisecond, or less. Real-time can also refer to a simultaneous or substantially simultaneous occurrence of a first event with respect to occurrence of a second event. The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

Input: As used herein, the term "input" or "inlet," as used interchangeably herein, generally refers to an incoming solution to the cassette. For example, a sample solution. Such solution may comprise fluid or buffer that comprises cells or fluid or buffer that does not comprise cells. The cells may be human cells.

Output: As used herein, the term "output" or "outlet," as used interchangeably herein, generally refers to an outgoing solution from the cassette. For example, a product solution comprising isolated or enriched cells and/or a waste solution comprising "non-target" cells and/or waste components. The isolated or enriched cells and the non-target cells may be human cells.

Sample Processing System

FIG. 1 schematically illustrates a sample processing system 100 for processing an input solution and generating an outlet solution that is enriched in one or more target particles. The sample processing system 100 may have a particle separation unit 110, an input unit 120, and an output unit 130.

The input unit 120 can comprise one or more containers or bags for storing an input solution that can comprise a sample. A sample can contain or be suspected of containing a nucleic acid molecule or cells. For example, a sample can be a biological sample containing one or more nucleic acid molecules or cells. The biological sample can be obtained (e.g., extracted or isolated) from or include blood (e.g., whole blood), plasma, serum, urine, saliva, mucosal excretions, sputum, stool and tears. The sample may contain blood, a blood product (such as a leukapheresis or apheresis product) also containing an anti-coagulant (e.g., EDTA, EGTA, heparin, citrate, ACD-A, or a thrombin inhibitor). The sample can be a human sample. The biological sample can be a fluid or tissue sample (e.g., skin sample). In some examples, the sample is obtained from a cell-free bodily fluid, such as whole blood. In some examples, the sample can include circulating tumor cells. In some examples, the sample is an environmental sample (e.g., soil, waste, ambient air and etc.), industrial sample (e.g., samples from any industrial processes), and food samples (e.g., dairy products, vegetable products, and meat products). The sample may be processed prior to loading into the microfluidic device. The sample may suitably be an apheresis product or a leukapheresis product (e.g., leukopak).

The particle separation unit 110 can be configured to process a variety of volumes of a sample solution. For example, the particle separation unit 110 can be configured to process a sample solution of about 50 mL, 100 mL, 150 mL, 200 mL, 250 mL, 300 mL, 350 mL, 400 mL, 450 mL, or about 500 mL or greater. The sample may comprise a blood product or an apheresis product such as a leukapheresis product. The particle separation unit 110 can successfully and efficiently separate out the target cells from the input sample solution. For example, the sample solution can be processed, and a product solution generated enriched in target particles collected, in about 120 minutes, 110 minutes, 100 minutes, 90 minutes, 80 minutes, 70 minutes, 60 minutes, 50 minutes, 40 minutes, 30 minutes, 20 minutes, or about 10 minutes or less. To accomplish this, the particle separation unit 110 can operate at a variety of flow rates. For example, the particle separation unit 110 can process a sample solution at a rate greater than or equal to about 200 mL/hr, 250 mL/hr, 300 mL/hr, 350 mL/hr, 400 mL/hr, 450 mL/hr, or about 500 mL/hr.

The input unit 120 can also comprise containers for holding several other types of input solutions. For example, the input unit 120 can comprise a priming solution. The priming solution may comprise low surface tension liquids such as alcohols. For example, the priming solution may comprise isopropyl alcohol at varying concentrations in water. The isopropyl alcohol can be configured to be in a solution at about 10%, 20%, 30%, 40%, 50%, 60%, 70%, 80%, 90%, 95%, 96%, 97%, 98%, or about 99% or higher with the remaining percentage of solution being water. The priming solution can further comprise surfactants added to buffers. For example, the priming solution can comprise a surfactant (e.g., Polyethylene glycol sorbitan monolaurate (TWEEN)) 10%, 9%, 8%, 7%, 6%, 5%, 4%, 3%, 2%, or 1% or lower of a buffer in a saline solution. The priming solution can further comprise poloxamers added to the buffers. For example, the priming solution may comprise a poloxamer (e.g. F68, F127, 407, L64, P65, P84, P85, F88, P103, P104, P105, F108, or P123) at about 10%, 9%, 8%, 7%, 6%, 5%, 4%, 3%, 2%, or 1% or lower in a buffered or isotonic solution. The priming solution can be configured to be the first input solution that enters the particle separation unit 110 before a separation process occurs. The priming solution can be configured to prime the particle separation unit 110 in preparation for receiving a sample. For example, the priming solution can ensure the removal of all air from a fluid path in the particle separation unit 110. The particle separation unit 110 can use the priming solution to get primed and ready to receive a sample in solution in about 60 minutes, 50 minutes, 40 minutes, 30 minutes, 20 minutes, or about 10 minutes or less.

The input unit 120 can also comprise a media solution. The media solution may comprise a clean buffer solution that is configured to enter the particle separation unit 110 alongside a sample solution. The media solution can comprise solutions with or without the inclusion of added proteins. For example, the media solution can comprise a saline solution (e.g., 0.9% NaCl, phosphate buffered saline, tris buffered saline, or Hank's balanced salt solution) with or without the inclusion of proteins such as bovine serum albumin (BSA) or human serum albumin (HSA). Media based solutions may comprise plasmalyte, DMEM, TexMACS, OpTmizer, RPMI, MEM, Hams F12, EMEM, F-12 K, StemXVivo, Stemline, IMDM, or other commercially available cell culture media. The solutions may be appropriately buffered at a pH at or near normal physiological pH (e.g. about 7.4).

The input unit 120 can also comprise a diluent solution. The diluent solution can also be configured to enter the particle separation unit 110 alongside the sample solution and media solution. The diluent solution can be configured to combine with the sample solution to achieve a desired concentration of the sample solution. The exposure time of the diluent solution to the sample solution can be brief and limited to the time each solution is inside the cassette 112. The diluent solution can be the same as the sample solution. The diluent solution can also be different. For example, the diluent solution can comprise a saline solution with or without the inclusion of proteins such as BSA or HSA. The diluent solution can also comprise a reagent that is exposed to the sample solution and then washed out during the separation process.

The particle separation unit 110 can further comprise a cassette 112 and microfluidic cartridge 114 subunit. The particle separation unit 110 may comprise housing to store the cassette 112. The cassette 112 can be configured to receive any one of the aforementioned input solutions. The cassette 112 can be configured to receive and hold the microfluidic cartridge 114 subunit. The cassette 112 can be configured to receive and hold one or more microfluidic cartridges 114, and such microfluidic cartridges can operate in series, in parallel, or have a combination of microfluidic cartridges in series and microfluidic cartridges in parallel. The microfluidic cartridge 114 can be configured to process the sample solution to generate an outlet solution that is enriched in one or more target particles of the sample solution.

The input unit 120, particle separation unit 110, and output unit 130 can all be configured to be fluidically coupled to each other. For example, the input unit 120 can comprise a plurality of containers comprising the one or more input solutions discussed herein. The particle separation unit 110 can comprise a cassette and one or more microfluidic cartridges configured to perform a target particle separation. The cassette can comprise a plurality of fluidic channels that extend between the inputs, outlets, and microfluidic cartridges. The output unit 130 can comprise a plurality of containers comprising the one or more outlet solutions discussed herein.

The sample processing system 100 can be such that each of these components are releasably and fluidically coupled to one another. The components of the input unit 120, particle separation unit 110, and output unit 130 can be fluidically coupled to each other in such a way that the entire sample processing system 100 operates under a closed end-to-end sterile environment. The closed environment provides the benefits of operating under a sterile environment. For example, no user intervention manual control and/or contact is required for the sample processing system 100 to perform a separation process generating a product that is enriched in one or more target particles and free of contamination. Thus, a product can be collected in one of the outlet containers that has not been exposed to an external non-sterile environment. Further, a sample from an input container can enter the cassette without being exposed to an external non-sterile environment. Further, the closed end-to-end environment is such that the sample solution need not come into contact with any non-reusable components of the sample processing system 100 to prevent contamination. Non-reusable components can comprise pumps, sensors, and valves, as will be described herein. In addition, during the separation process, no intermediary reagents may be required to be externally added into or internally removed from the closed end-to-end environment, further supporting a sterile inline continuous processing of an incoming sample.

The sample processing system 100 can be configured to use a plurality of sterile coupling mechanisms in order to preserve the sterility of the sample processing system 100. For example, a coupling mechanism between an input container and a tubing connecting the input container to the cassette can comprise a sterile spike and a sterile spike port. For example, an input container can be a bag having a sterile spike port, and tubing comprising a sterile spike can be configured to fluidically connect the bag to the cassette in such a way to preserve the sterility of the sample processing system 100.

The output unit 130 can comprise one or more containers or bags for storing an output solution that can comprise a product. For example, the output unit 130 can comprise a product solution, a primary waste solution, and a secondary waste solution. The product solution may comprise the target particles that were desired to be separated from the input sample solution.

The product solution may further comprise a clean buffer from the input media solution, or the product solution may solely comprise the target particles. The primary and secondary waste solutions can comprise the unwanted particles from the input sample solution. For example, the target particles can be separated by the particle separation unit 110 and leave the particle separation unit 110 in the product solution, and the unwanted particles can remain in the input sample solution stream and exit the particle separation unit 110 in the primary and secondary waste solution streams. The product outlet stream can comprise a high percentage recovery of target particles as compared to the input sample stream. For example, the percent recovery of target particles in the product solution can be about 50%, 55%, 60%, 65%, 70%, 75%, 80%, 85%, 90%, or about 95% of the target particles from the sample input stream. The target particles recovered may be recovered in an intact and viable form in the product solution stream. For example, at least 50%, 55%, 60%, 65%, 70%, 75%, 80%, 85%, 90%, 91%, 92%, 93%, 94%, 95%, 96%, 97%, 98%, or 99% or more of the target cells recovered in a product solution can remain viable after a separation process occurs. In some cases, at least 50%, 55%, 60%, 65%, 70%, 75%, 80%, 85%, 90%, 91%, 92%, 93%, 94%, 95%, 96%, 97%, 98%, or 99% or more of the target cells recovered in a product solution can remain viable after a separation process occurs relative to the input material or sample or input sample.

In certain embodiments, the enriched target particles may comprise live cells from a blood or blood-related sample input solution. In certain embodiments, the enriched target cells comprise leukocytes. In certain embodiments, the enriched target cells comprise stem cells. In certain embodiments, the enriched target cells comprise peripheral blood mononuclear cells. In certain embodiments, the peripheral blood mononuclear cells comprise CD3+ cells. The target particles recovered may be recovered in an intact and viable form in the product solution stream. To accomplish this, the fluidic content in the particle separation unit 110 can be configured to be subject to pressures no greater than about 30 psi to about 60 psi. For example, the fluidic content can be generally subject to pressures from about 5 psi to about 40 psi during a separation process. In further embodiments, the average pressure during particle/cell separation is about 10 to about 30 psi, about 10 to about 20 psi, about 10 to about 15 psi, or about 15 to about 20 psi. The pressure of the fluid can vary or be adjusted, depending on the volume and/or rate at which the fluid is moved through the channels. These forces can allow for gentle separation of the target particles from the sample solution thereby improving cell viability in the product stream.

In certain embodiments, the unwanted particles in the sample solution may comprise platelets. In certain embodiments, unwanted particles may also comprise red blood cells. In certain embodiments, the target particles in the sample solution may comprise white blood cells.

The particle separation unit 110 can separate out a high percentage of unwanted particles from the product solution. For example, the particle separation unit 110 can separate out about 50%, 55%, 60%, 65%, 70%, 75%, 80%, 85%, 90%, or about 95% or more of the unwanted particles in the sample solution from the product solution.

The particle separation unit 110 can also be configured to recirculate any of the input solutions after the input solutions have passed through the cassette 112 and microfluidic cartridge 114. Recirculation may allow the cassette 112 to concentrate the target cells into a fixed volume or a fixed concentration. For example, the target cells can be fixed to be recovered in about 10 ml, 20 mL, 30 mL, 40 mL, 50 mL, 60 mL, 70 mL, 80 mL, 90 mL, 100 mL, 110 mL, 120 mL, 130 mL, 140 mL, or about 150 mL or more of a buffer and target cell fluid. The recirculation may occur in parallel, in series, or a combination of in series and in parallel, to the target cell separation, enabling collection of the product cells, in clean buffer, and in a specified volume. If the recirculation occurs in parallel, the recirculation process does not affect the overall run time of the target cell separation. The recirculation can be configured to begin at a specified time in the separation process. The recirculation can also be configured to begin based on feedback from the sample process system 100. For example, the input unit 120 and output unit 130 can comprise mass sensors configured to weigh each of the solutions contained in the one or more containers or bags of the input unit 120 and output unit 130. For example, the mass sensor can measure the weight of solution in a product solution bag, and once a threshold weight has been reached in the product solution bag, the recirculation process can begin.

The particle separation unit 110 can be fully or partially automated. For example, a user can input desired process settings and the particle separation unit 110 can perform the separation without user intervention, as will be discussed herein. The particle separation unit 110 can also allow a user to manually adjust process setting while the particle separation unit 110 is performing the separation process.

In certain embodiments, data from the pressure sensors, bubble sensors, or mass sensors are logged over a time interval to track and periodically evaluate sensor drift and periodically evaluate. In some embodiments, sensor data may be tracked over a time interval which may consist of a period of a few days, a week, several weeks, a month, or several months (e.g. 1, 2, 3, 4, 5, 6, 7, 8, 9, 10, 11, 12, 24, 36, 48, 60, or 72 months). In some embodiments, sensor data may be tracked over an interval of up to 1, 5, 10, 20, 50, 100, 1000, or 2000 past run protocol instances. In some embodiments, the sensor data are evaluated to identify drift once per hour, once per day, once per instance of a run protocol, or in real time during the course of a run protocol. In some embodiments, the sensor data are evaluated to identify whether a drift is significant by comparing measured sensor values to expected sensor values. In some embodiments, the expected sensor values are determined based at least in part on a factory sensor calibration. In some embodiments, the expected sensor values are determined at least in part based on the stored sensor data from a past time interval of a few days, a week, several weeks, a month, or several months (e.g. 1, 2, 3, 4, 5, 6, 7, 8, 9, 10, 11, 12, 24, 36, 48, 60, or 72 months), or from up to 1, 5, 10, 20, 50, 100, 1000, or 2000 past run protocol instances. In some embodiments, the expected sensor values are determined based at least in part on information about a current run protocol. In some embodiments, the expected sensor values are determined based at least in part on a maximum error tolerance (e.g. about 1%, about 5%, about 10%, about 15%, or about 20%). In some embodiments, the maximum error tolerance defines a maximum tolerated deviation of sensor data from an expected value determined using a factory sensor calibration and/or the information about the current run protocol. In some embodiments, the sensor data are evaluated to identify whether a drift is significant by comparing measured sensor values to expected sensor values. In some embodiments, the expected sensor values may comprise a range, wherein the range is defined by the expected value plus or minus the maximum error tolerance. In some embodiments, if a drift outside of the expected value range is detected a user may be alerted, the run protocol may be suspended, an error condition may be set, and/or a service warning may be displayed.

In certain embodiments, a plurality of systems or particle separation units may be networked together to provide greater throughput.

Particle Separation Unit

Figure 2A:
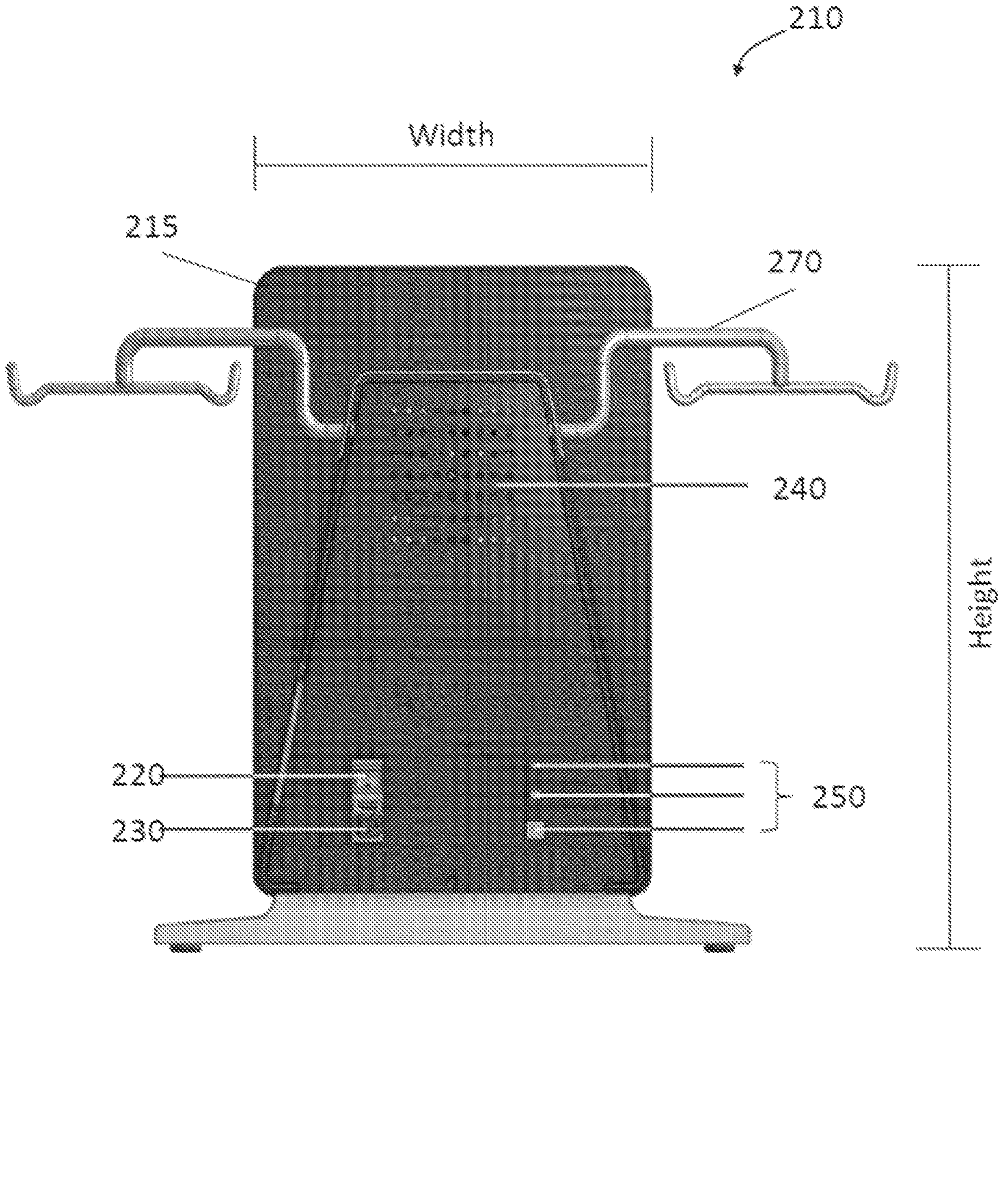
FIG. 2A illustrates a perspective view of a rear portion of a particle separation unit in accordance with some embodiments.

FIGS. 2A-2E illustrate several perspective views of a particle separation unit 210 that can be used in embodiments described herein. FIG. 2A illustrates a perspective view of the rear portion of the particle separation unit 210. The particle separation unit 210 can be contained in housing 215 that can be sized and shaped to hold the particle separation unit 210. The housing 215 can be of a lightweight, compact, and portable nature. For example, the housing can store the particle separation unit 210 and be placed on a desk/tabletop such as a wet bench. The housing 215 can have a height, width, or depth dimension ranging from about 280 mm to about 1,220 mm. The housing 215 can have a surface area ranging from about 470,400 $mm^2$ to about 8,930,400 $mm^2$. The housing 215 can have an internal volume ranging from about 21,952,000 $mm^3$ to about 1,815,848,000 $mm^3$. The particle separation unit 210, together with the housing 215, can have a total weight ranging from about 20 kg to about 120 kg, from about 40 to about 100 kg, or from about 50 to about 70 kg. In some aspects, the particle separation unit may weigh less than about 100 kg, 80 kg, or less than about 70 kg.

The rear of the particle separation unit 210 can comprise a power switch 220, a power inlet 230, and network connections 250. The power switch 220 can be toggled to turn the particle separation unit on and off. The network connection 250 can comprise an ethernet, USB-C, and USB mini-B connection. The network connection 250 can connect the particle separation unit 210 to a computer network, as will be discussed herein, allowing the computer system to control the processing settings and allowing a user to monitor the separation process and change process settings in real time.

The rear of the particle separation unit 210 can also comprise a vent 240. The vent 240 can be configured to dispel heat from inside the housing 215 as the particle separation unit is performing the separation process.

The rear of the particle separation unit 210 can also be configured to have one or more hangers 270 that extend from the rear of the housing 215 and out to the sides. The hangers 270 can be releasably or permanently coupled to the housing 215 of the particle separation unit 210. The hangers 270 can be configured to receive and retain a variety of inlet/outlet solution bags. For example, the hangers 270 can hold a sample solution bag for entry into the particle separation unit 210. Each of the hangers 270 can also be configured to include a mass sensor. The mass sensor can help the system keep track in real-time of how much solution is remaining in a solution bag and help to monitor and manage, in real-time, fluid movement throughout the particle separation unit 210.

Figure 2B:
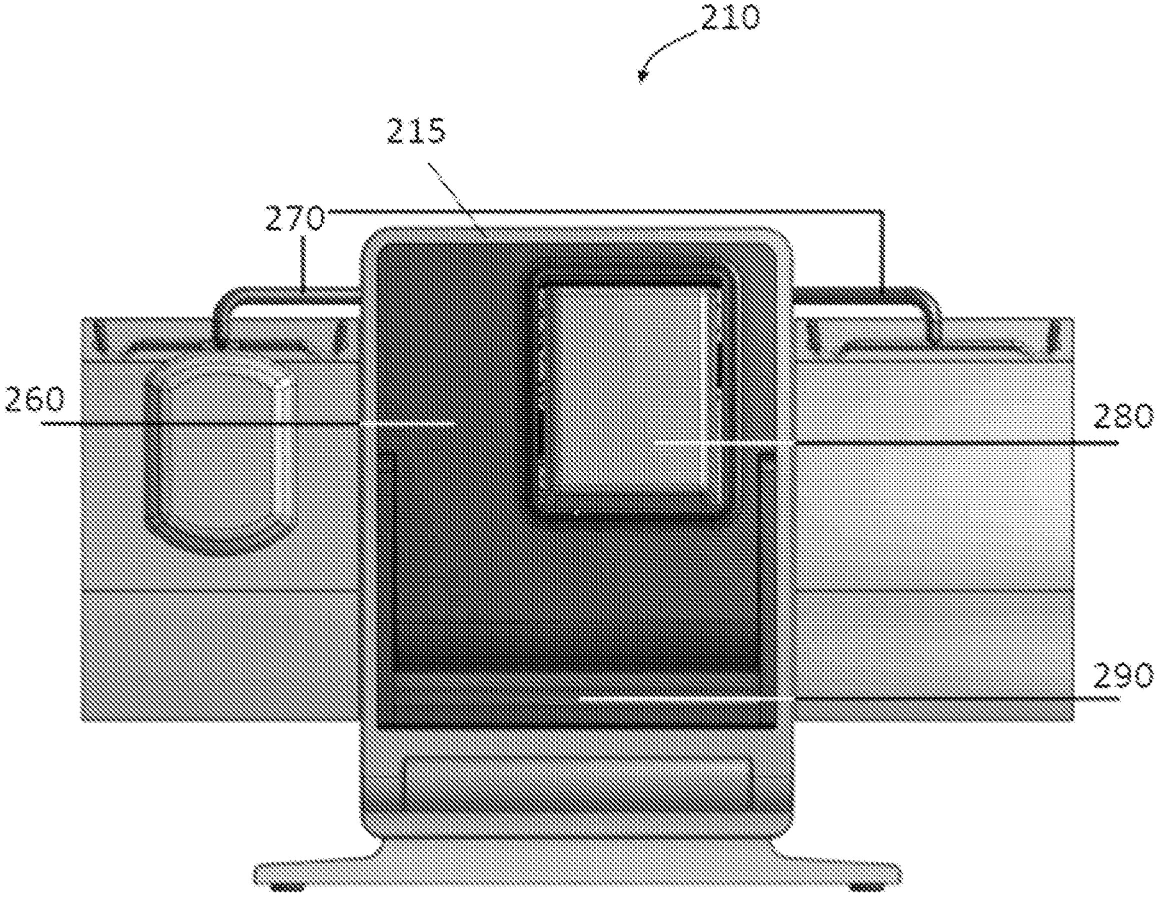
FIG. 2B illustrates a perspective view of a front of a particle separation unit with a door in a closed position in accordance with some embodiments.

FIG. 2B illustrates a perspective view of the front of the particle separation unit 210 with a door 260 in the closed position. The front of the particle separation unit 210 can comprise a door 260. The door 260 can further comprise a microfluidic cartridge housing 280 and a handle 290. The door 260 can be opened and closed, allowing a user to gain access to the internals of the particle separation unit 210.

Figure 2C:
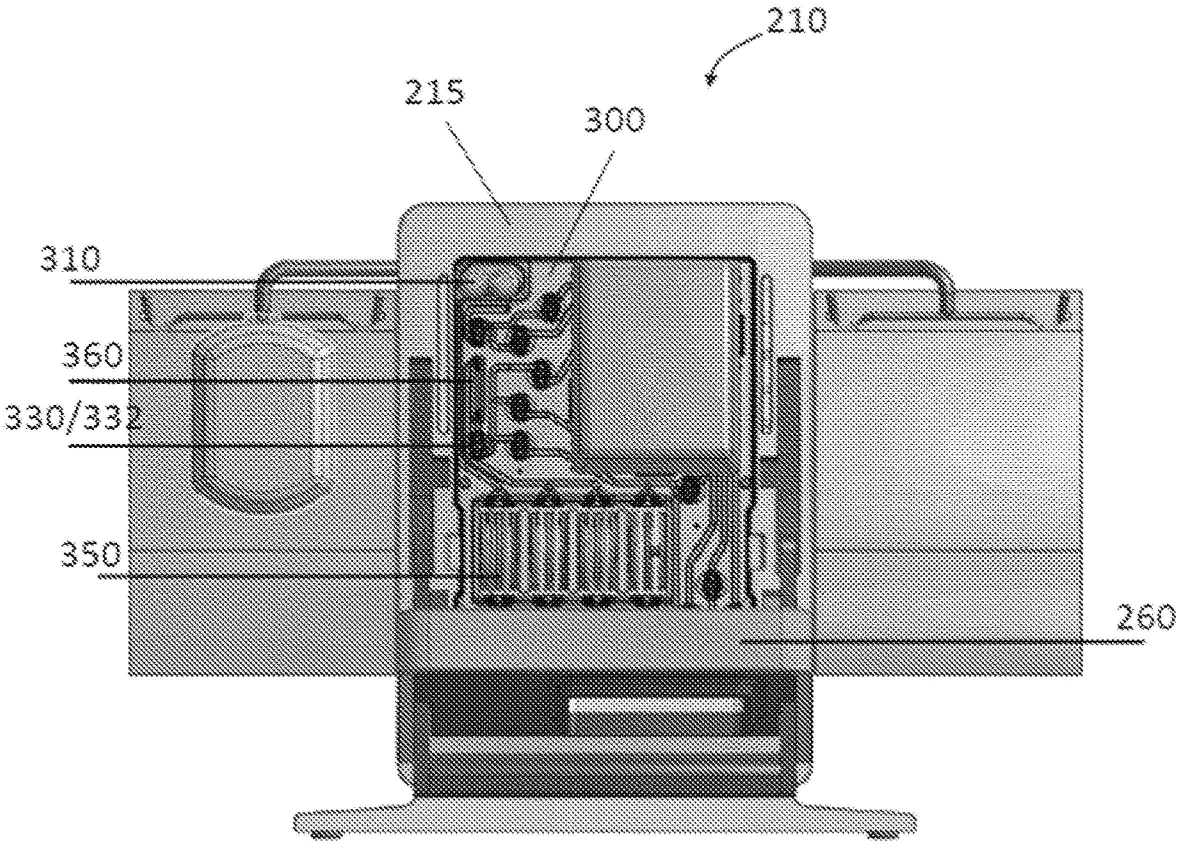
FIG. 2C illustrates a perspective view of a front of a particle separation unit with a door in an open position in accordance with some embodiments.

FIG. 2C illustrates a perspective view of the front of the particle separation unit 210 with a door 260 in an open position, showing the cassette 300 inside the particle separation unit 210. The housing 215 may include a receiving portion comprising a recess, cavity, or slot. The cassette 300 may be releasably coupled to the particle separation unit 210 at this receiving portion. The cassette 300 can be configured to be interchanged and/or mounted onto the particle separation unit 210 using a quick release mechanism and/or without the use of tools. The receiving portion of the housing 215 may be configured to releasably couple to a variety of different types of cassettes. Other cassettes may be configured for different types of cell/target particle processing. For example, an exemplary cassette can be configured for blood sample processing, whereas another cassette may be configured for processing silica beads in a sample solution. The housing 215 can be configured to releasably couple to these variety of cassette's, allowing the particle separation unit 210 to perform a variety of separation processes for a desired target particle separation. In addition, a variety of microfluidic cartridges can be releasably coupled to the cassettes, allowing for the separation of target particles with a variety of critical sizes.

Figure 2D:
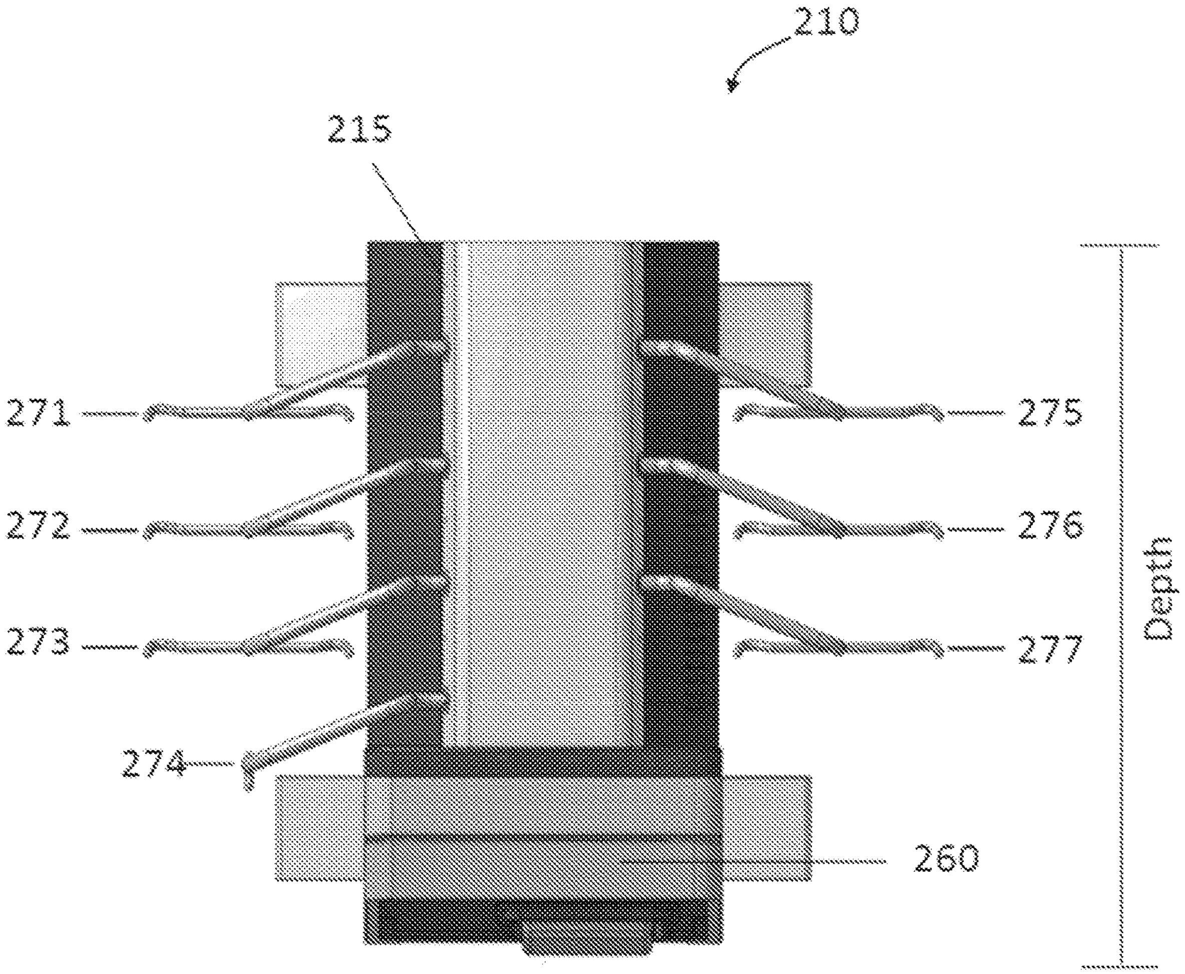
FIG. 2D illustrates a perspective view of a top portion of a particle separation unit in accordance with some embodiments.

FIG. 2D illustrates a perspective view of the top portion of the particle separation unit 210. As illustrated, all of the hangers 270 are in view from this perspective. The particle separation unit 210 can comprise 2, 3, 4, 5, 6, 7, 8, 9, or 10 or more hangers 270. As illustrated in FIG. 2D, the particle separation unit comprises seven hangers 270. The hangers 270 can comprise a priming bag hanger 271, a media bag hanger 272, a diluent bag hanger 273, a sample bag hanger 274, a secondary waste bag hanger 275, a primary waster bag hanger 276, and a product bag hanger 277. These hangers may be configured to hold a bag containing a solution configured to enter into or exit out of the particle separation unit 210. For example, the sample bag hanger 274 can be configured to receive and hold a sample bag comprising a sample solution that is to be separated in the particle separation unit 210. The solution bags may be releasably coupled to the hangers 270.

Figure 2E:
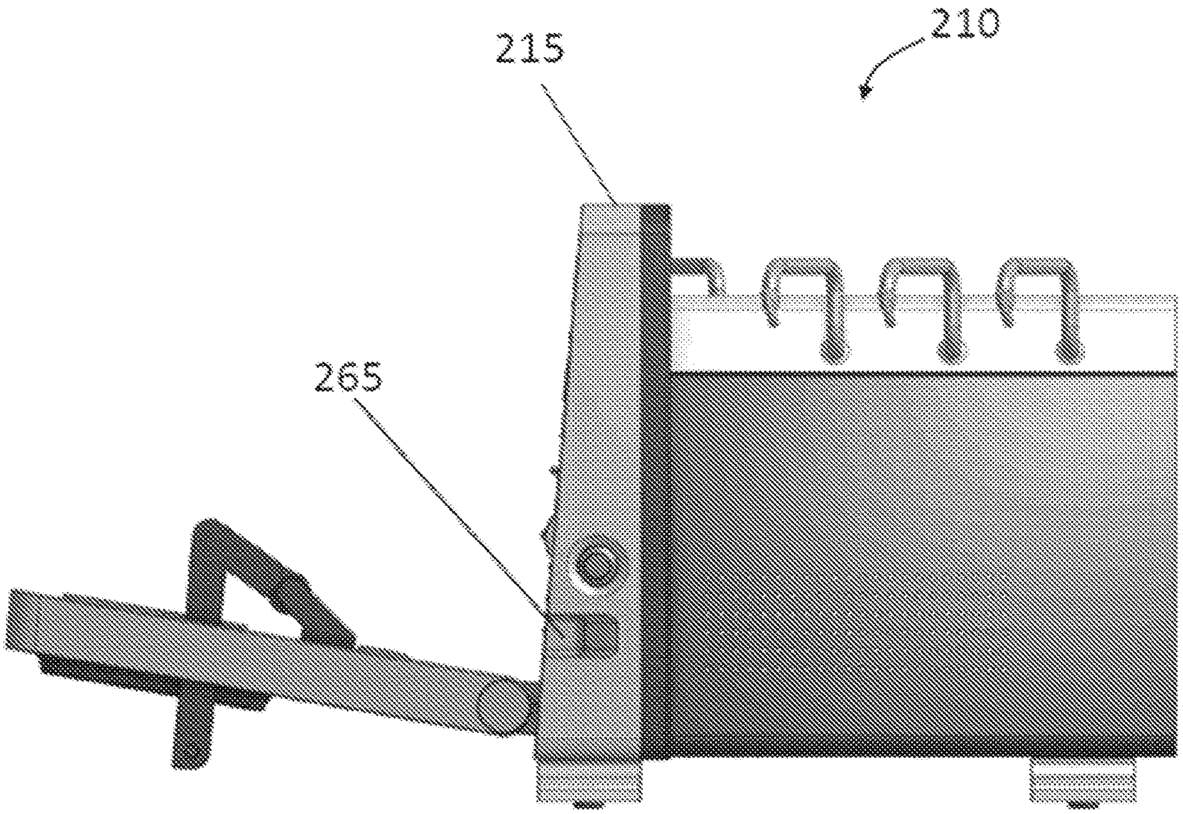
FIG. 2E illustrates a perspective view of a side of a particle separation unit in accordance with some embodiments.

FIG. 2E illustrates a perspective view of a side of the particle separation unit 210. The housing 215 of the particle separation unit 210 may comprise a recess 265 on a side of the particle separation unit 210. The recess may be on a left side, a right side, or on both sides of the particle separation unit 210. The recess 265 can be configured to hold tubing that fluidically couples the inlet and outlet solutions to the particle separation unit 210, as will be discussed herein.

Figure 2F:
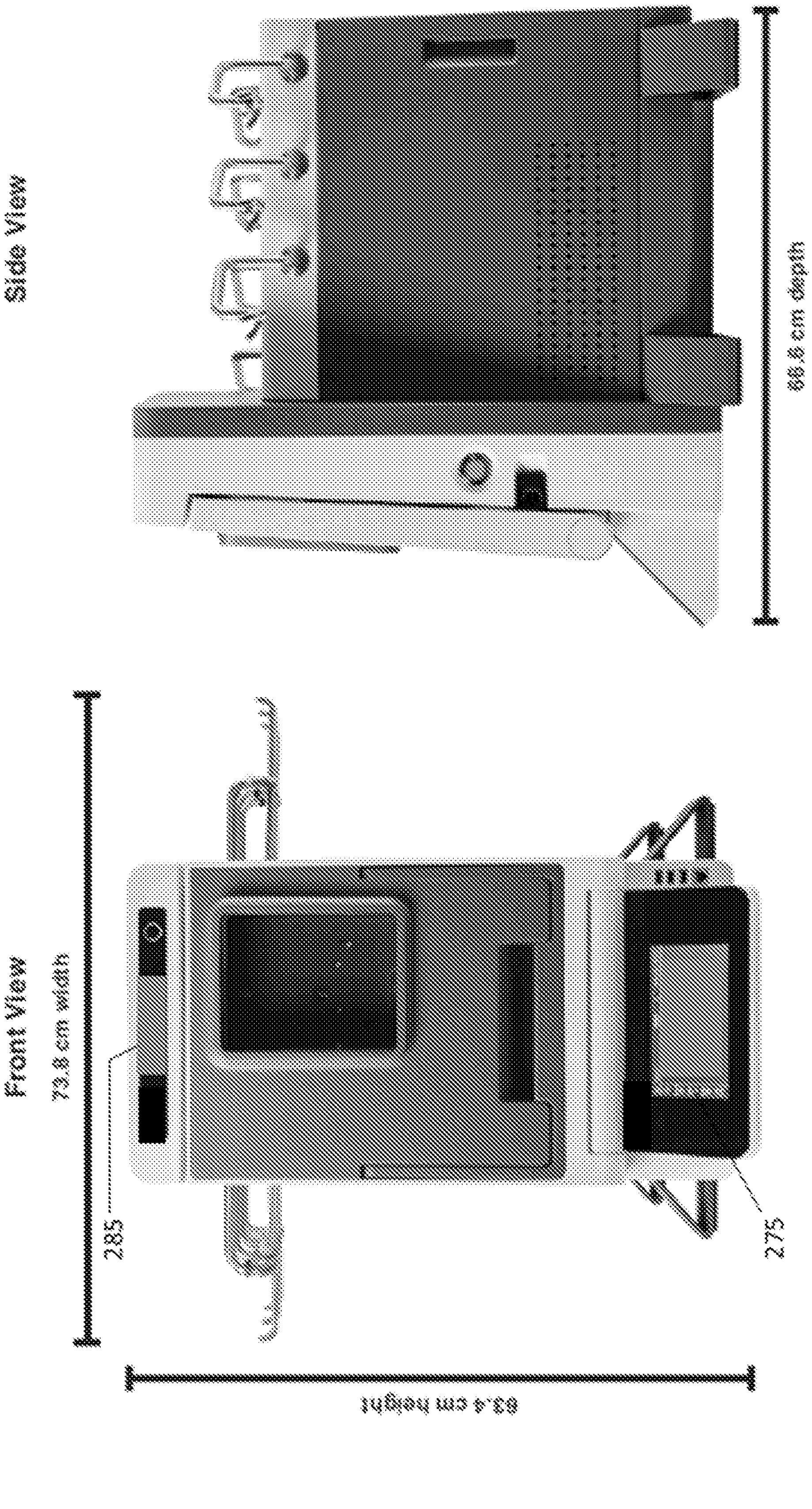
FIG. 2F illustrates front and side views of a particle separation unit with a primary and secondary display in accordance with some embodiments.

FIG. 2F illustrates front and side views of an example particle separation unit in accordance with some embodiments, wherein the particle separation unit comprises a primary touchscreen display 275 and a secondary status display 285.

Cassette

In an exemplary embodiment, FIGS. 3A-3F illustrate a cassette 300 for sorting target particles. The present disclosure envisions target particles to include a wide range of particles, such organic and inorganic particles, natural and synthetic particles, and combinations thereof. The target particles presented herein are exemplary embodiments of target particles and are not limited by the exemplary embodiments. In various embodiments, target particles may include any particles having a critical size of at least about 1, 2, 3, 4, 5, 6, 7, 8, 9, 10, 11, 12, 13, 14, or 15 microns. In some embodiments, target particles may be identifiable through fluorescence. In some embodiments, target particles may include inorganic particles, such as metal beads and silica beads. For instance, metal beads may include beads containing alumina (e.g., gamma alumina). In some embodiments, target particles may include silica beads. Target particles may include polymers, such as polystyrene, polyethylene, poly(vinylpyrrolidone), acrylamidopropyl-PEG and derivatives thereof. For example, the polymers may be a Merrifield resin, hydroxymethyl resin, Wang resin, aminomethyl resin, SASRIN resin, TentaGel S AC resin, TentaGel PHB resin or TentaGel S NI-I2 resin. Target particles may also include carbon nanotubes and fullerenes. Such target particles may include particles that are used in split-pool synthesis. Additionally, in some embodiments, target particles may include cellular material. Cellular material may include whole cells, lysed cells, cellular components, extracellular matrix, biological tissue, and portions thereof. In some embodiments, target particles may also include biomolecules, which include proteins, peptides, antibodies, carbohydrates, lipids, nucleic acids, nucleotides, primary metabolites, secondary metabolites, and natural products. Target particles may also include small molecules, both synthetic and natural small molecules, which weigh less than 1000 Daltons. In some embodiments, target particles may include viruses. Cellular material may comprise a cell suspension. Cells may be any cell derived from an organism, which include human, animal, fungal, microbial, insect, and modified cells thereof. A cellular material mixture comprises cellular material, opaque particles, and an aqueous solution. Examples of an aqueous solution include media, buffer, and water. The device of the present disclosure may be used to isolate cells that differentially express or produce proteins, carbohydrates, enzymes, peptides, hormones, receptors, and additionally cells that produce antibodies, genetically engineered cells, and activated cells. In an exemplary embodiment, according to FIGS. 3A-3F, the cassette 300 can be configured to be operably coupled to a panel of the particle separation unit 210 comprising a degassing unit 310, bubble sensors 320, pressure sensors 330, valves 340, and pumps 350. The cassette 300 may comprise an in-line mixer 360, pressure sensor membranes 332, pressure sensor gaskets 335, valve membranes 342, valve gaskets 345, a microfluidic cartridge housing 370 for receiving and holding one or more microfluidic cartridges, and tubing 380. Alternatively, the cassette 300 can be configured to comprise all of the degassing unit 310, bubble sensors 320, pressure sensors 330, pressure sensor membranes 332, valves 340, valve membranes 342, pumps 350, an in-line mixer 360, a microfluidic cartridge housing 370, and tubing 380.

A cassette 300 can be configured to be for single use or the cassette 300 can be reusable for multiple uses. In one embodiment of a cassette 300 for sorting target particles, the cassette 300 may comprise a microfluidic cartridge housing 370 configured to receive and hold one or more microfluidic cartridges configured to sort target particles, as will be discussed herein. The one or more microfluidic cartridges can be releasably coupled to the cassette 300 at the one or more microfluidic cartridge ports 372 of the cassette 300. The cassette may comprise tubing 380 configured to connect the cassette 300 to a sample bag which may comprise a sample comprising target particles that are desired to be separated. The tubing 380 may also be configured to connect the cassette 300 to a variety of other sources and be configured to provide the cassette with a variety of outlets. For example, the tubing 380 may comprise inlet tubing comprising priming solution tubing 381, media tubing 382, diluent tubing 383, and sample tubing 384. In addition, the tubing 380 may comprise outlet tubing comprising product recirculation tubing 385, product collection tubing 386, and waste tubing 387. The tubing 380 may be configured to allow a sample to flow freely through a plurality of pathways in the cassette 300 and allow the separation process to be performed. The tubing 380 may be configured to enter/exit at a bottom portion of the cassette 300, as illustrated in FIG. 3B. The inlet tubing may be configured to enter at a left side of the bottom of the cassette 300, and the outlet tubing may be configured to exit at a right side of the bottom of the cassette 300. The tubing 380 may run through the cassette 300, providing the cassette with a plurality of pathways.

Figure 3A:
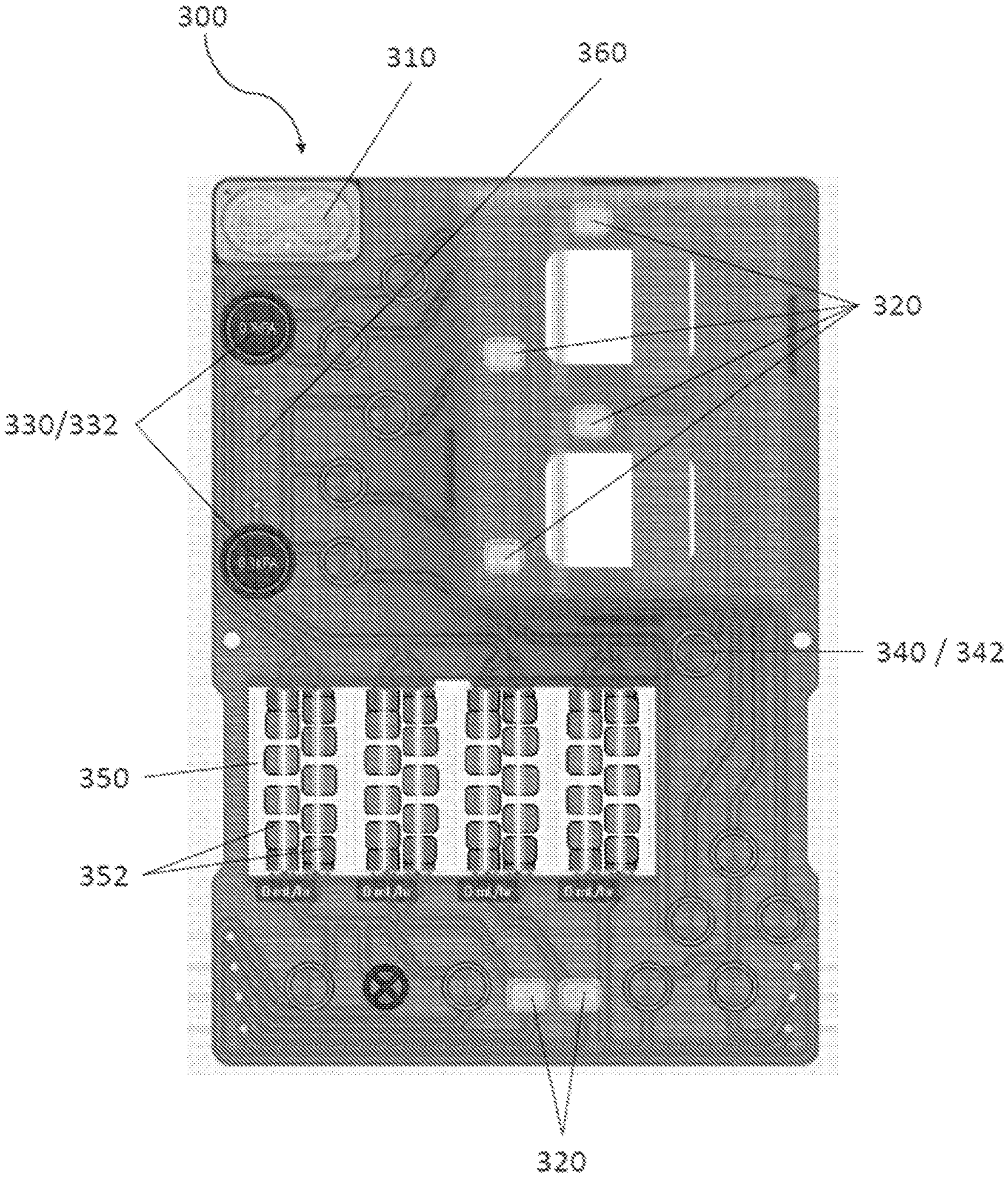
FIG. 3A-3C illustrates a cassette with several components in accordance with some embodiments.
Figure 3B:
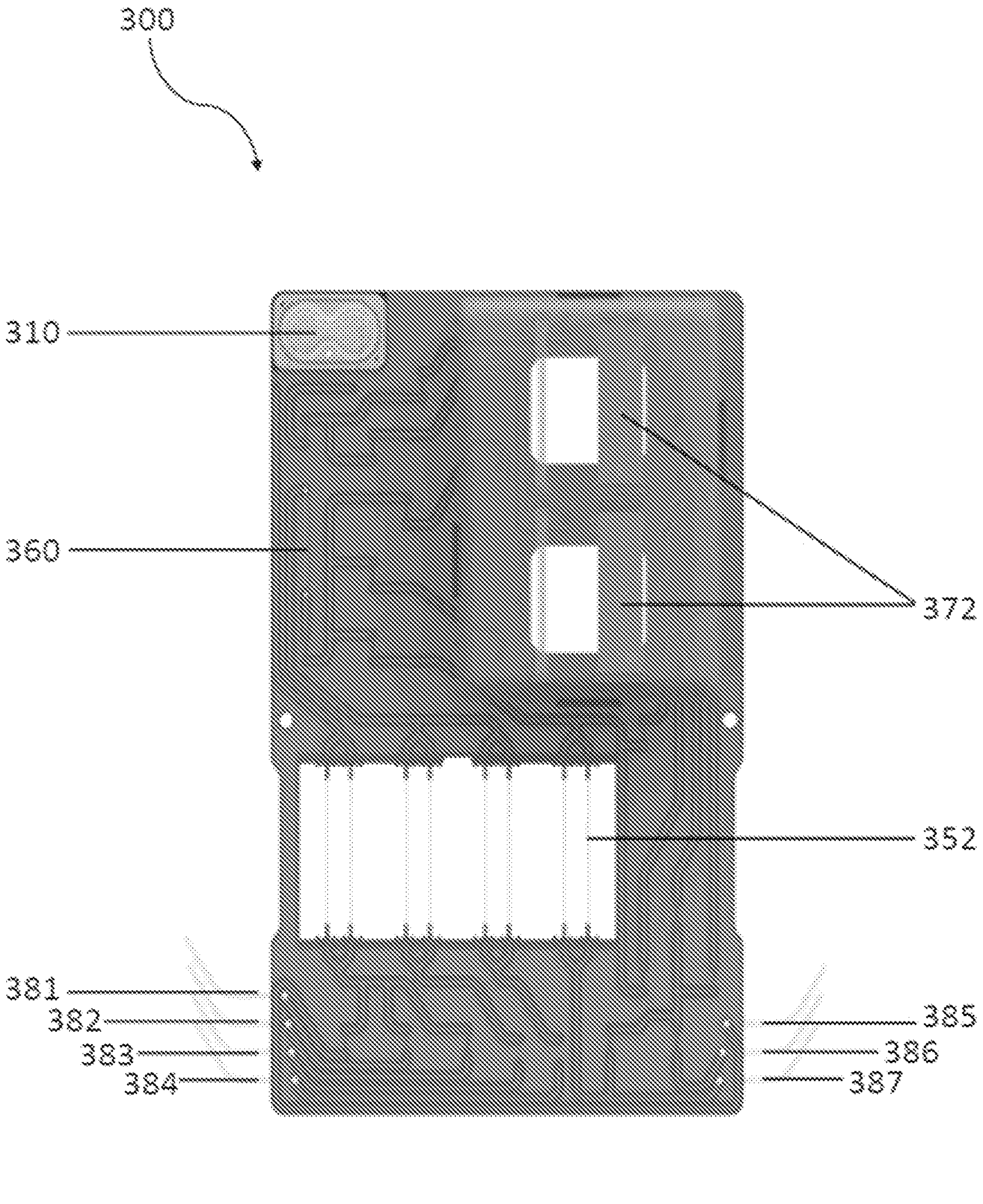
Figure 3C:
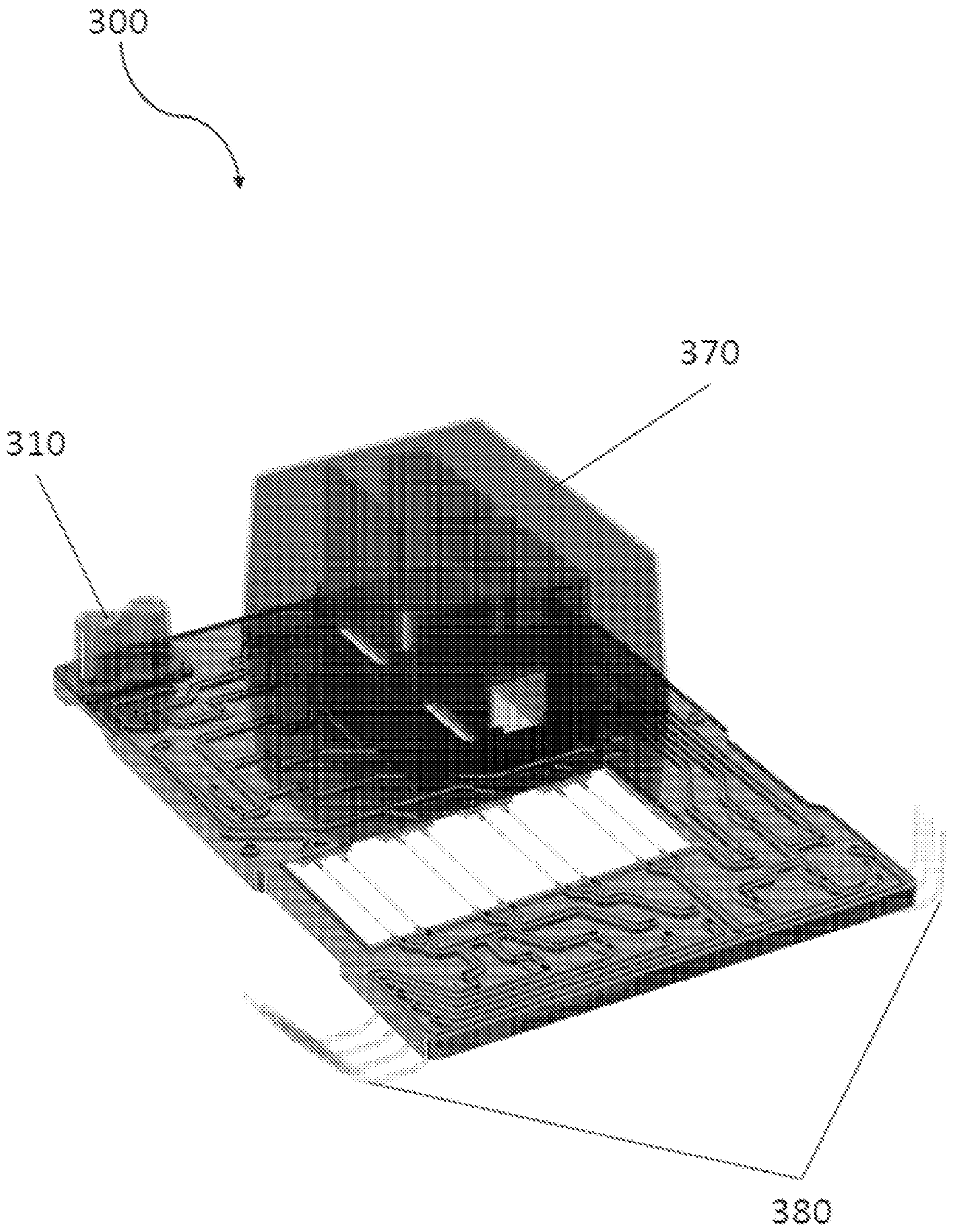
Figure 3D:
FIG. 3D illustrates a product bag and a waste bag in accordance with some embodiments.
Figure 3E:
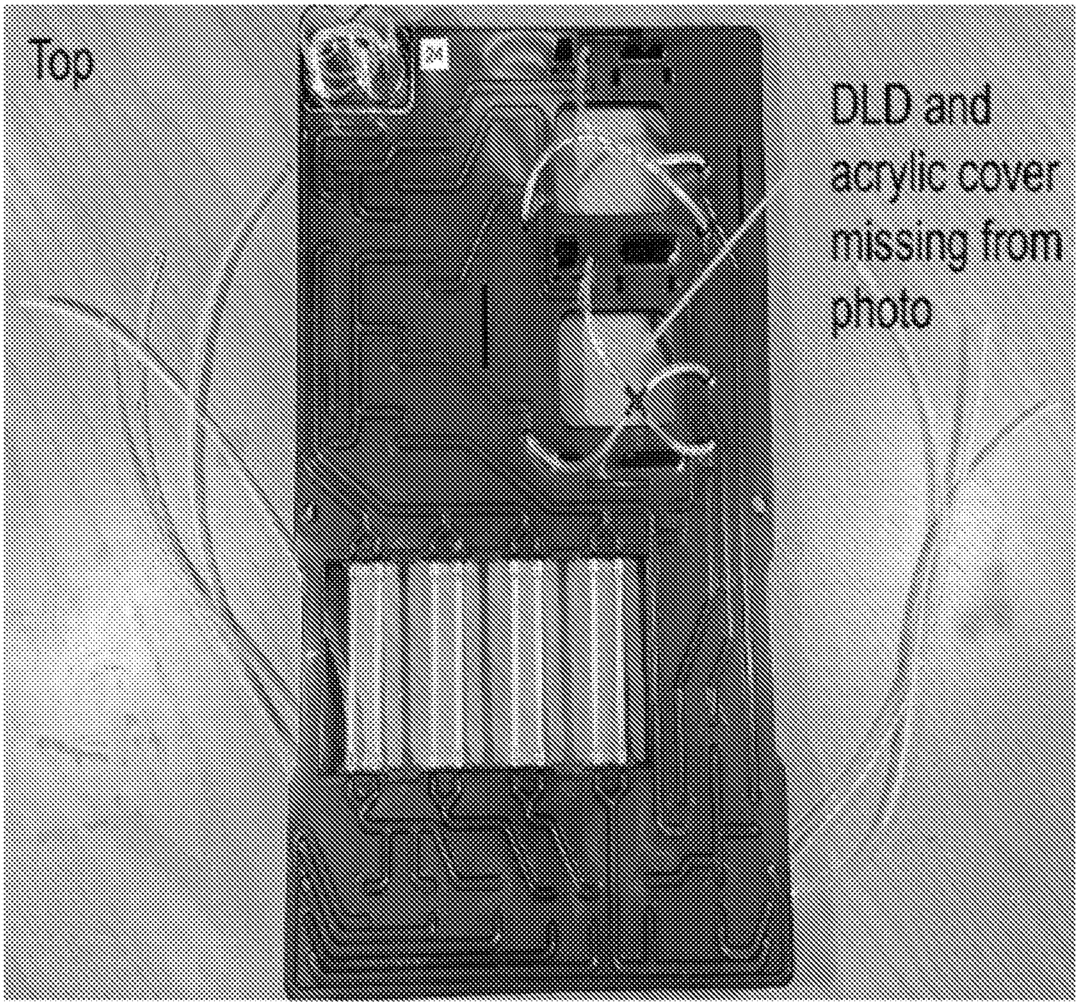
FIG. 3E illustrates a perspective view of a top portion of a cassette in accordance with some embodiments.
Figure 3F:
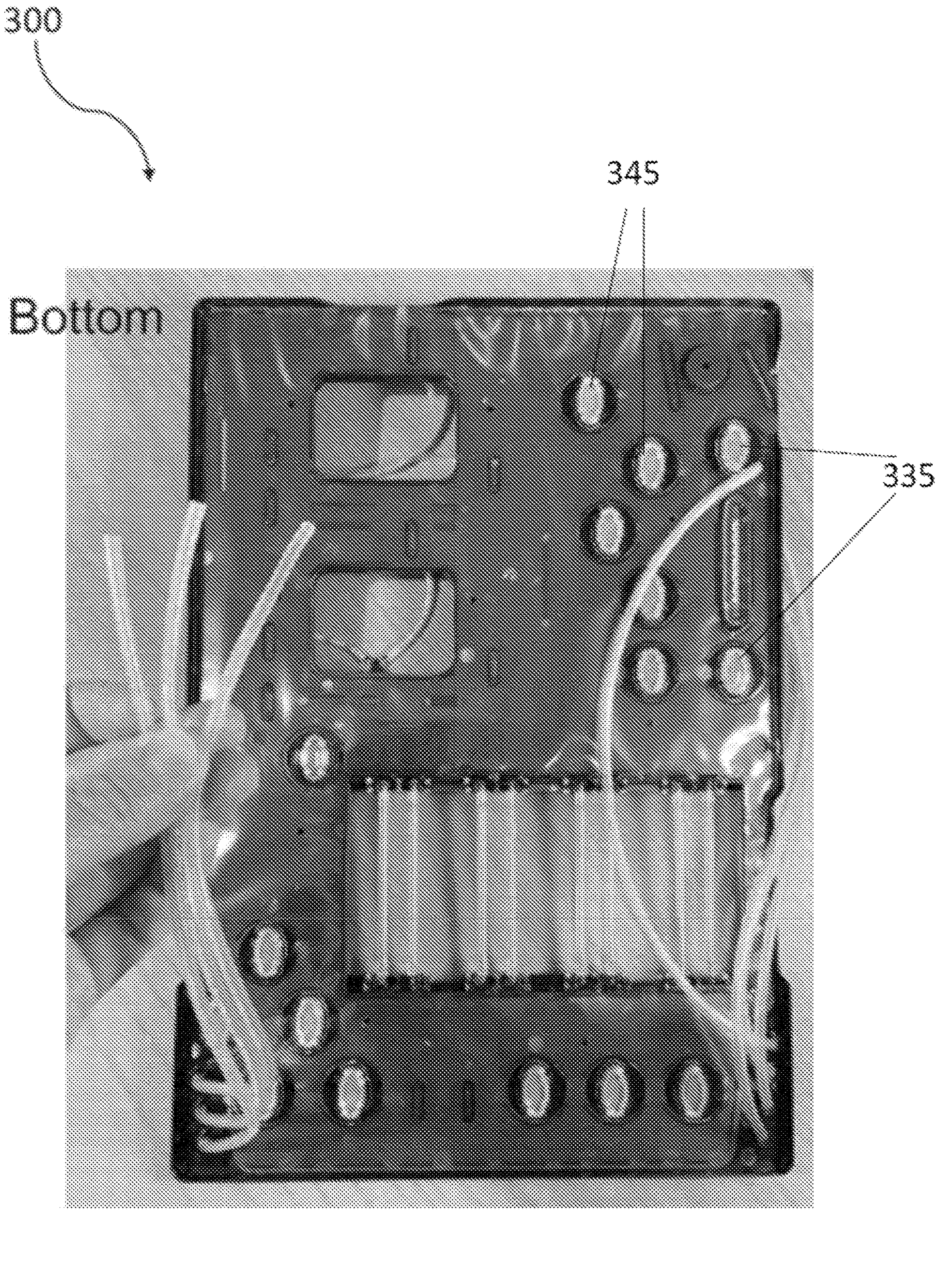
FIG. 3F illustrates a perspective view of a bottom portion of a cassette including a plurality of valve gaskets and two pressure sensor gaskets, which fluidically connect the cassette to a particle separation unit in accordance with some embodiments.

The product collection tubing 386 and waste tubing 387 can be configured to fluidically couple the cassette 300 to a product bag 396 and waste bag 398 via a tubing connection 392, as illustrated in FIG. 3D. The product collection tubing 386 and waste tubing 387 may allow the product bag 396 and waste bag 398 the cassette 300 and the microfluidic device to be in fluidic communication with each other. In a similar fashion, the priming solution tubing 381, media tubing 382, diluent tubing 382, and sample tubing 384 may also be configured to allow a priming solution bag, media bag, a diluent bag, and a sample bag, respectively, to be in fluidic communication with the cassette 300 and microfluidic device. The product collection tubing 386 and waste tubing 387 can be configured to allow a product collection bag and waste bag, respectively, to be in fluidic communication with the cassette 300 and microfluidic device. The product recirculation tubing 385 may be configured to take an outlet stream from the microfluidic device and recirculate that stream back into the microfluidic device for further processing.

The product recirculation tubing 385 can be operably connected to at least one recirculating pathway in the cassette 300. The recirculation pathways can be configured to be separate from any other pathway in the cassette 300 or can be configured to adjoin or connect to one or more of the other plurality of pathways of the cassette 300. The recirculation pathway can be configured to extend from an inlet portion to an outlet portion of the cassette 300 and be configured to operate and recirculate target particles in a clockwise or counter-clockwise direction on the cassette 300. In addition, a plurality of recirculation pathways can be configured to direct a sample into and out of the one or more microfluidic cartridges. The microfluidic cartridges may be operably coupled to the one or more cartridge ports 372 to establish fluidic communication with the cassette, such that the one or more microfluidic cartridges are configured to separate the one or more target particles from the sample, and the at least one recirculating pathway is configured to recirculate the one or more target particles through the cassette 300 to concentrate the one or more target particles into a predefined volume of media. The recirculation pathway can be configured to operate in this way so as to achieve a desired concentration or volume of target particles in a product solution. The microfluidic cartridges and the at least one recirculating pathway can be configured to be operated in parallel, in series, or a combination of in series and in parallel. Operating in parallel allows for optimized and minimized run times for the particle separation unit to complete a target particle separation process.

The microfluidic cartridges and the recirculating pathways can be configured to be operated independently of each other. For example, the microfluidic cartridges can be configured to separate the target particles from a sample solution without affecting a recirculating process performed in the recirculation pathways. Additionally, the recirculating process performed in the recirculation pathways can be performed without affecting the separation process performed by the microfluidic cartridges. The microfluidic cartridges and the at least one recirculating pathway may also be individually controllable in real-time to achieve a desired concentration of the one or more target particles in the product.

The tubing 380 may be releasably coupled to the inlet and outlet solution bags. For example, the tubing 380 and tubing connection 392 of a solution bag can comprise weld-compatible tubing and the tubing 380 and tubing connection 392 may be coupled together with the use of a sterile tube welder.

A sample bag may be configured to hold a sample comprising any of the target particles described herein that may be desired to be separated. The priming tubing 381 may connect a priming bag to the cassette 300 that may contain a priming solution. The priming solution may be configured to run through the cassette before the introduction of any other sample/solution to ensure the cassette is ready to receive a sample/solution for processing. For example, the priming solution can be configured to run through the cassette and ensure the removal of all air from the fluid path. The media tubing 382 may connect a media bag to the cassette 300 that may contain a media solution. The media solution may comprise a clean buffer solution that is configured to be collected alongside the target cells in a product collection bag. The diluent tubing 383 may connect a diluent bag to the cassette that may contain a diluent solution. The diluent tubing may be configured to introduce a diluent solution in the cassette 300 which may affect the concentration that the target cells are recovered in the product collection bag.

The product collection tubing 386 may connect a product collection bag to the cassette 300 that may collect the product stream from the microfluidic device comprising the target cells. The product collection stream may also comprise buffer from the media bag. The waste tubing 387 may connect a waste bag to the cassette 300 that may collect the waste stream from the microfluidic device comprising the unseparated target from the original sample. The product recirculation tubing 385 may recirculate the target cells into the microfluidic cartridges, as mentioned herein. This may allow the cassette to concentrate the target cells into a fixed amount. For example, the target cells can be fixed to be recovered in about 10 mL, 20 mL, 30 mL, 40 mL, 50 mL, 60 mL, 70 mL, 80 mL, 90 mL, 100 mL, 110 mL, 120 mL, 130 mL, 140 mL, or about 150 mL or more of a buffer and target cell fluid. A fixed recovery volume may be achieved through use of a specialized bag designed with a compartment having the desired fixed volume. For example, cells may enter the product bag on the side with the compartment, and the bag may be configured so that there is only a minimal amount of overflow to the other side of the bag, which is the recirculation side. The fluid in the recirculation side may remain relatively free of cells which settle out on the fixed volume compartment side. For example, if the flow into the bag is constant at 300 mL/hr, a fixed percentage of the total flow is product. The outflow may be varied such that the outflow is equal to the buffer flow rate. The buffer flow rate may be controlled using mass triggers to determine when to begin recirculation. For example, when the product bag mass is less than a high-mass set point such as 30 g, product is fed at a constant rate into the product bag. When the product bag reaches the high-mass set point i.e. 30 g in this example, the product may be drawn out of the recirculation side until the product bag mass reaches a low-mass set point, such as for example 25 g. When the low-mass setpoint is reached, the recirculation (or the drawing of the product out of the bag) is stopped, and buffer is flowed back into the DLD, to fill the bag with product until it reaches the high-mass set point. In some examples, the buffer flow rate may be 600 mL/hr, in which case, the net flow into the bag may be 300 mL/hr or −300 ml/hr (300 in, 600 out). In some examples, the flow rates are adjusted to continuously oscillate between the upper and lower mass triggers until a separation run is complete, whereupon the product bag can be filled to a final dilution level, for example to produce a final mass of 40 g. In some embodiments, the weir bag is constructed to overflow at 20-25 g for a lower mass trigger of 25 g, so there is always a small amount of fluid on the other side of the weir, even when the lower mass trigger is reached, to reduce the risk of pulling air into the system. The mass triggers can be user-selected. Weir bags may also be user selected based upon chosen mass triggers, to prevent air from entering the system. In some embodiments, recirculation may be performed without specialized weir bags as long as the cellularity in the product bag is kept to a level of 150 M/mL or below. The recirculation may occur in parallel, in series, or a combination of in parallel and in series, to the target cell separation, enabling collection of the product cells, in clean buffer, and in a specified volume. If the recirculation occurs in parallel, the recirculation process does not affect the overall run time of the target cell separation.

As illustrated in FIG. 3A, the flexible fluidic channels 352 of the cassette 300 may be operably coupled to the one or more pumps 350 of the panel of the particle separation unit 210. Alternatively, the pumps 350 may be configured to be part of the cassette 300 itself. The flexible fluidic channels 352 may be configured to extend longitudinally on the cassette 300. The flexible fluidic channels 352 may comprise subsets of fluidic channels. Each subset of the flexible fluidic channels 352 may comprise two or more fluidic channels. The pumps 350 may comprise two or more pump heads configured to operably couple to the two or more fluidic channels in each subset of the flexible fluidic channels 352. The one or more pumps 350 can be configured to transport and control a flow rate of the fluidic content of the one or more inlet and outlet streams of the cassette 300. For example, the pumps can transport a sample, media, diluent, waste, product, priming, and a recirculation solution stream throughout the cassette 300. The pumps 350 can be configured to transport the fluidic content without any moving parts contacting the fluidic content. The pumps 350 may include peristaltic pumps peristaltically coupled to the flexible fluidic channels 352 and configured to control the flow rate of the streams in the cassette 300. The pumps 350 can be configured to be operably coupled to the flexible fluidic channels 352 of the cassette 300 and extend longitudinally on the flexible fluidic channels 352. The pumps 350 may also be configured to be controllable independent from one another. The pumps 350 can be independently controlled in real-time as the separation process is occurring. The pumps 350 can operate out-of-phase or in-phase relative to each other. For example, the pumps 350 can operate out-of-phase by about 180 degrees, 170 degrees, 160 degrees, 150 degrees, 140 degrees, 130 degrees, 120 degrees, 110 degrees, 100 degrees, 90 degrees, 80 degrees, 70 degrees, 60 degrees, 50 degrees, 40 degrees, 30 degrees, 20 degrees, or about 10 degrees or less. Additionally, the pumps 350 can be configured to each achieve the same flow rate, different flow rates, a same flow direction, or different flow directions.

The panel of the particle separation unit 210 may comprise an independent pump to be operably coupled to each of the inlet and outlet streams of the cassette 300. For example, an independent pump may be included for each of the sample solution, diluent solution, and media solution, and priming solution. Additionally, an independent pump can be used for each of the outlet streams. For example, the waste streams, product streams, and recirculation streams. These pumps can be individually controllable to modulate the flow rate of each of these streams. In an example where an independent pump is provided for a sample solution stream and a diluent solution stream, the pumps may be independently controllable so as to adjust a dilution factor of the target particles entering the cassette 300. The pump controlling the flowrate of the sample solution and the pump controlling the flow rate of the diluent solution can be independently controlled in real time so as to adjust or achieve a desired diluent factor of the target particles as the target particles enter the cassette 300.

Additionally, an independent pump may be included to control the flow rates of the outlet streams. For example, an independent pump can be configured to control the flow rate of the waste streams and product streams. Independent pumps can be provided for each stream, for example, to reach a desired ratio of flow rates of a waste stream exiting the particle separation unit relative to an amount entering the cassette 300 from any of the inlet streams and the product stream exiting the cassette 300. For example, an independent pump can be used to control the flow rate of a waste stream exiting the cassette 300 to influence a ratio of the amount of waste relative to an amount of the product exiting the cassette and/or an amount of the sample provided to the cassette 300. Additionally, an independent pump can be used to control the flow rate of a sample stream relative to a flow rate of a diluent stream in order to influence a ratio of the amount of sample relative to an amount of diluent that is entering the cassette 300. Further, individually controllable pumps can be used for the recirculation stream and sample stream to enable a desired concentration of the target particles in the product solution.

As mentioned, the pumps 350 may comprise peristaltic pumps. The peristaltic pumps may be desired for their ability to gently promote the flow of fluid throughout the pathways of the cassette 300. This can increase the likelihood of recovering viable cells at the end of a separation process. For example, at least 50%, 55%, 60%, 65%, 70%, 75%, 80%, 85%, 90%, 91%, 92%, 93%, 94%, 95%, 96%, 97%, 98%, or 99% or more of the target cells recovered in a product solution can remain viable after a separation process occurs.

The pumps 350 can be configured to be operably coupled to and sandwich the flexible fluidic channels 352 that extend longitudinally along the cassette 300. The pumps 350 can thus be configured to actuate in a longitudinal direction parallel to the flexible fluidic channels 352. The pumps 350 can also be configured to actuate in a traverse direction perpendicularly to the flexible fluidic channels 352.

The pumps 350 can comprise a set of pump heads that can be operably coupled to each subset of the plurality of flexible fluidic channels 352. Each set of pump heads in each pump can comprise two or more pump heads. The two or more pump heads can comprise two or more sets of rollers. The two or more pump heads can be configured to actuate in-phase with each other. The two or more pump heads can be configured to actuate out-of-phase relative to each other to transport the fluidic content through the flexible fluidic channels 352 towards or away from the microfluidic cartridges. Operating the two or more pump heads out-of-phase with each other in this fashion can result in a flow of fluidic content that is less pulsatile than if the pump had a single pump head. The two or more pump heads can be configured to actuate out-of-phase by about 180 degrees, 170 degrees, 160 degrees, 150 degrees, 140 degrees, 130 degrees, 120 degrees, 110 degrees, 100 degrees, 90 degrees, 80 degrees, 70 degrees, 60 degrees, 50 degrees, 40 degrees, 30 degrees, 20 degrees, or about 10 degrees or less.

The two or more pump heads in each pump 350 can each be configured to be operably coupled to and sandwich the two or more fluidic channels in a subset of the flexible fluidic channels 352. The fluidic content in the two or more fluidic channels in each subset of the flexible fluidic channels 352 can be transported by the two or more pump heads and be combined together at an outlet of each subset into a single fluid path. The two or more pump heads in each pump 350 can be configured to have a fixed motion relative to each other. For example, the two or more pump heads in each pump 350 can be moving at a same rate and in a same direction relative to each other. Alternatively, the two or more pump heads in each pump 350 can be moving at different rates and in directions opposite relative to each other.

The pumps 350 can be configured such that the fluidic content running through the cassette 300 is subject to pressures no greater than about 30 psi to about 60 psi. For example, the fluidic content can be generally subject to pressures from about 5 psi to about 40 psi during a separation process. The pumps can operate at a desired frequency. For example, the pumps can operate at about 200 revolutions per minute (rpm), 190 rpm, 180 rpm, 170 rpm, 160 rpm, 150 rpm, 140 rpm, 130 rpm, 120 rpm, 110 rpm, 100 rpm, 90 rpm, 80 rpm, 70 rpm, 60 rpm, or about 50 rpm or less. The pressure of the fluidic content can vary or be adjusted, depending on the volume and/or rate at which the fluid is moved through the channels. The pumps 350 can gently move the fluids along pathways of the cassette 300 in this fashion prior the inlet solutions meeting and mixing. The pumps 350, operating in this fashion, can also ensure that a minimum amount of clumping of particles occurs within any given stream.

In addition to the pumps 350, the panel of the particle separation unit 210 may also be configured to include one or more valves 340 that may be configured to help control the flow rate of the streams in the cassette 300. For example, the valves 340 can be operably coupled to valve membranes 342 on the cassette 300. Pressure sensors 330 may be operably coupled to pressure sensor membranes 332, which translate fluidic pressure into linear force on a load cell. The panel and cassette 300 may include 1, 2, 3, 4, 5, 6, 7, 8, 9, 10, 11, 12, 13, 14, 15, 16, 17, 18, 19, or 20 or more valves 340 and valve membranes 342 operably coupled to each other. The valve membranes 342 may be configured to lie in several locations throughout the cassette 300. For example, the streams may come into contact with the valve membranes 342 right at the entrance of the inlet streams before the pumps 350, after coming into contact with the pressure sensor membranes 332 and before coming into contact with the microfluidic devices, after coming into contact with the microfluidic devices, and upstream of the one or more bypass channels. The valve membranes 342 may be configured to lie in-line and be in fluidic communication with the several streams of the cassette 300. Each valve 340 can be individually controlled to help reach a desired flow rate for each of the individual streams. For example, each valve 340 can fully or partially prevent flow through a pathway of the cassette 300 by fully or partially closing the valve membrane 342 of a pathway. The valve 340 may comprise a pin, or other suitable component, to fully or partially push a valve membrane 342 closed in a pathway of the cassette 300 to restrict the flow of fluid through the pathway. For example, a valve membrane 342 may exist in line for the diluent stream, which may be closed or fully or partially opened by a valve 340 in order to help achieve a desired flow rate of the diluent stream entering the cassette 300 to help achieve a desired diluent factor of the target particles entering the cassette 300 in the sample solution. While a valve membrane 342 for the diluent stream is fully or partially closed by a valve 340, for example, a valve membrane 342 for the sample solution stream can be configured to remain in a position closer or further away from a closed position to help achieve the desired diluent factor. The valves 340 may also close or open the valve membranes 342 at a percentage value in comparison to being fully closed or opened. For example, the valve membranes 342 may be opened at 10%, 20%, 30%, 40%, 50%, 60%, 70%, 80%, or 90% or higher in order to achieve a desired flow rate of the stream where the valve membrane 342 sits.

In addition to the pumps 350 and valves 340, the panel of the particle separation unit 210 may also be configured to include one or more pressure sensors 330 that may be configured to help control the flow rate of the streams in the cassette 300. The cassette 300 may be configured to include one or more flexible pressure sensor membranes 332 operably coupled to the one or more pressure sensors 330. For example, the panel of the particle separation unit 210 and the cassette 300 may include 1, 2, 3, 4, 5, 6, 7, 8, 9, or 10 or more pressure sensors 330 and pressure sensor membranes 332 operably coupled together. The streams may come into contact with the pressure sensor membranes 332 after coming into contact with the flexible pump tubing 352 but before coming into contact with the microfluidic devices. The pressure sensors 330 can measure a pressure of the fluidic content passing through a pathway in the cassette 300 based on a force applied to the pressure sensor membranes 332 by the fluidic content as the fluidic content passes by. The pressure sensors 330 may be in communication with the other devices of the panel of the particle separation unit 210. For example, if a pressure sensor reads a pressure higher than a desired pressure reading, the pressure sensor may send a communication to one or more valves or one or more pumps that will cause the one or more valves or one or more pumps to adjust in order to lower the flow rate of the stream that has a high pressure reading and thus lower the pressure.

The panel of the particle separation unit 210 may also be configured to include a degassing unit 310. The degassing unit 310 may be configured to be operably coupled to gas permeable tubing in the cassette 300. The degassing unit 310 may be operably coupled to gas permeable tubing at a top portion of the cassette 300, and/or in proximity with the microfluidic cartridges.

It may be desired in a cassette 300 that any inlet stream to the microfluidic cartridges is absent any bubbles or dissolved gases. This may be desired to ensure efficient and proper processing of the microfluidic cartridges. The degassing unit 310 can be configured to remove dissolved gases via the gas permeable tubing and prevent bubble formulation prior to a sample being circulated through the one or more microfluidic cartridges. This can ensure that the cassette 300 is ready to receive a sample solution and that the cassette 300 will perform efficiently and properly throughout the separation process.

In addition to the degassing unit 310, the panel of the particle separation unit 210 may also include several bubble sensors 320. For example, the panel may comprise 1, 2, 3, 4, 5, 6, 7, 8, 9, or 10 or more bubble sensors 320 configured to detect the presence of bubbles in any of the several streams in the cassette 300. The pathways in the cassette 300 may be configured to abut up against the bubble sensors 320 on the panel in such a way that the bubble sensors can detect the presence or absence of bubbles in the pathways. The pathways may abut and come into contact with the bubble sensors as the pathways enter the cassette 300 before the pumps 350, and before and after coming into contact with the microfluidic devices. For example, the bubble sensors 320 may be configured to detect the presence of air bubbles in a sample stream prior to the sample stream entering the microfluidic cartridges. If the bubble sensors 320 detect the presence of air bubbles, the system may provide an alert/notification to the user. A non-limiting example of bubble sensors may include optical, ultrasonic, and capacitor-based bubble sensors.

The cassette 300 may be configured to include one or more bypass channels. The cassette 300 can be configured to use the valves 340 and pumps 350 to direct a stream into the bypass channels in order to direct a steam away from one of the sensors and/or the microfluidic cartridges of the cassette 300.

The bubble sensors 320 may be configured to work in concert with the bypass channels of the cassette 300. For example, if the bubble sensors 320 detect the presence of an air bubble in a sample stream, the bypass channels can be used in order to direct this sample stream away from the microfluidic cartridges to ensure the stream does not enter the microfluidic cartridges with the air bubbles. As an additional example, the bubble sensors 320 can help to redirect another stream that has air bubbles detected in it before it comes into contact with a sample stream, thereby preventing the contamination of the sample stream with air bubbles.

The cassette 300 may further be configured to include an in-line mixer 360. The in-line mixer 360 may be configured to be in fluidic communication with any of the streams of the cassette 300. The in-line mixer 360 may be configured to come after the pumps 350 and before the microfluidic devices. The in-line mixer 360 may be configured to mix any of the streams in the cassette in order to deliver a homogenous mixed solution. For example, the in-line mixer 360 may be configured to mix the product recirculation stream with the media stream in order to reach a homogenous mixture of product and buffer in the product collection stream.

The in-line mixer 360 can comprise channels that run in parallel with the other plurality of pathways and channels that run through the cassette 300. The in-line mixer 360 can be configured to receive multiple different solution streams and can comprise one or more gates/obstacles that can gently mix the one or more streams together. The in-line mixer 360 can also comprise a plurality of channels, wherein the gates/obstacles can be configured to promote mixing. The components of the in-line mixer can be configured such that no moving parts are required to perform a mixing of fluidic channels. This mixing can be performed gently, thereby influencing a higher likelihood of recovering viable cells at the end of a separation process. For example, the in-line mixer may be configured to mix an incoming sample with a diluent inline on the cassette prior to the sample being circulated through the microfluidic cartridges. The in-line mixer 360 can receive the sample solution in a first fluidic channel, and receive the diluent in a second fluidic channel, and the first and second channel can converge to permit the mixing of the solutions. The in-line mixer 360 can comprise two or more channels in order to provide the mixing of two or more solutions.

Microfluidic Cartridge(s)

Figure 4A:
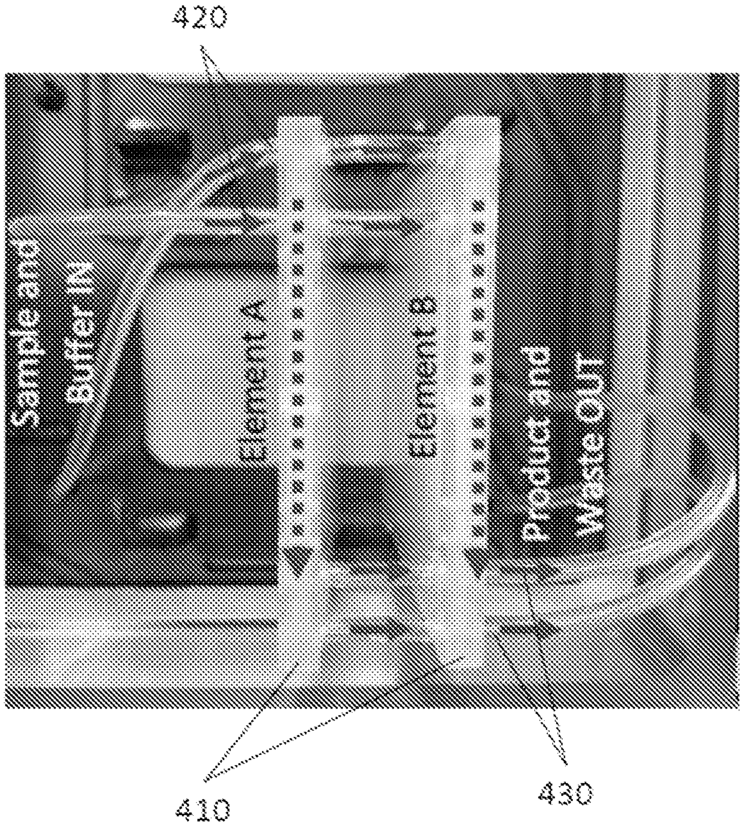
FIGS. 4A-4C illustrate perspective views of microfluidic cartridges in accordance with some embodiments.
Figure 4B:
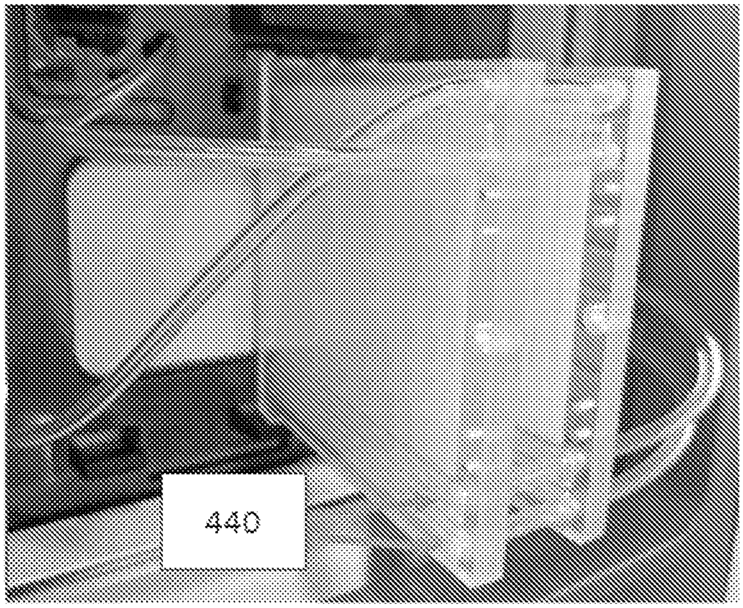
Figure 4C:
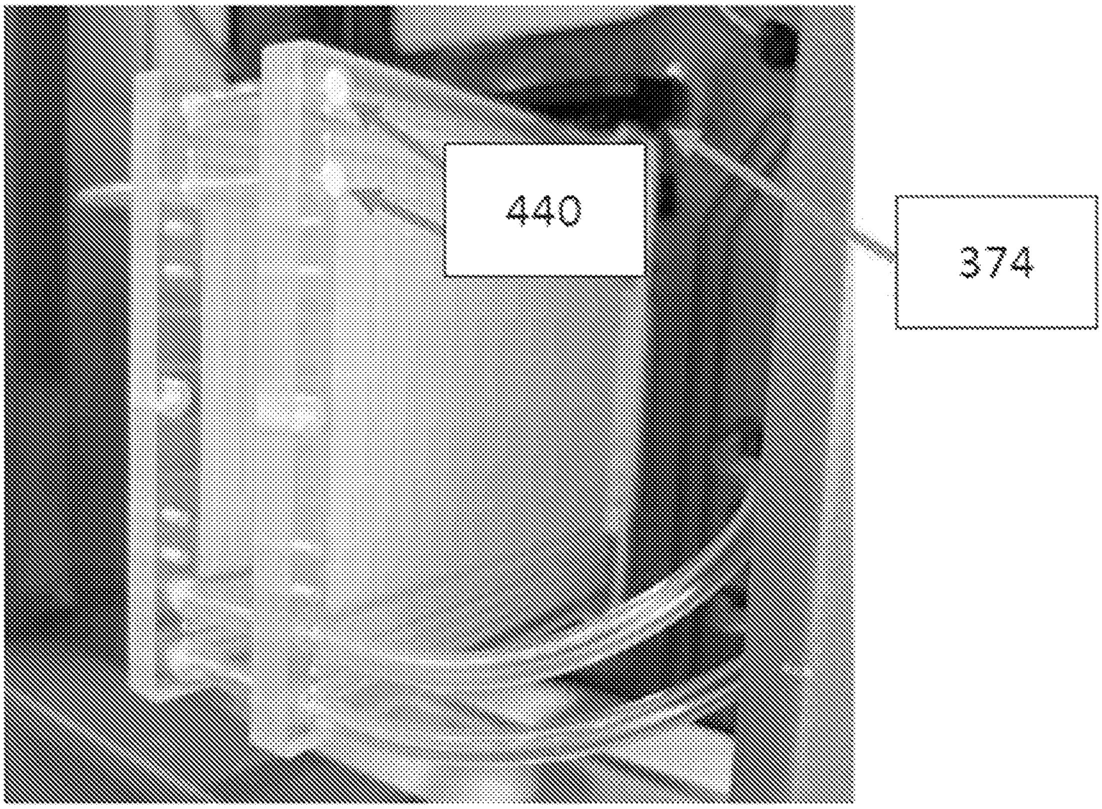

FIGS. 4A-4C illustrate microfluidic cartridges 410 which can be used in embodiments described herein. The microfluidic cartridges can be configured to be for single use, or the microfluidic cartridges can be reusable for multiple uses. As illustrated, two microfluidic cartridges 410 can be used stacked in parallel with each other in the cassette 300 to perform the separation process. The separation process can also be configured to be performed with one microfluidic cartridge, or three or more microfluidic cartridges, all of which can be stacked to operate in series, in parallel, or a combination of in series and in parallel. As illustrated, the microfluidic cartridges 410 can comprise two inlets 420 and two outlets 430. The microfluidic cartridges can also comprise one inlet and outlet, or three or more inlets and outlets. The number of inlets 420 may differ from the number of outlets 430. For example, a microfluidic cartridge can comprise more or less inlets 420 than outlets 430.

As illustrated in FIGS. 4B and 4C, the microfluidic cartridges 410 can comprise vents 440. The vents 440 can be configured to allow air bubbles to escape a stream as it passes through the microfluidic cartridge 410 while still keeping the fluidic content inside the channels of the microfluidic cartridge 410. For example, the vents 440 may be of a dual filter system. The two filters may comprise a hydrophilic membrane and a hydrophobic or oleophobic membrane. The hydrophilic membrane can be configured to reside closest to a fluid stream that is passing through the microfluidic cartridge 410, and the hydrophobic or oleophobic membrane can reside closest to an ambient environment surrounding the microfluidic cartridge 410. Each membrane can be of a variety of thicknesses. Each membrane can be of the same thickness, or one membrane may be thicker/thinner than the other membrane. For example, a hydrophilic membrane may be configured to be thicker than a hydrophobic membrane. The membranes may be of a thickness of about 10 microns, 20 microns, 30 microns, 40 microns, 50 microns, 60 microns, 70 microns, 80 microns, 90 microns, 100 microns, 110 microns, 120 microns, 130 microns, 140 microns, 150 microns, 160 microns, 170 microns, 180 microns, 190 microns, 200 microns, 210 microns, 220 microns, 230 microns, 240 microns, 250 microns, 260 microns, 270 microns, 280 microns, 290 microns, 300 microns, 310 microns, 320 microns, 330 microns, 340 microns or about 350 microns or thicker. Either membrane or both membranes can be selectively permeable such that gasses may escape the system, while cells, and fluids are maintained inside the system, and contaminants (e.g., viruses, bacteria) are excluded. Such selectively permeable membranes allow for escape of gasses and gas bubbles that may be detrimental to the system to while maintaining the sterility of the system. The pore size of the membranes may be about 5.0, 4.0, 3.0, 2.0, 1.0, 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, 0.09, 0.08, 0.07, 0.06, 0.05, 0.04, 0.03, 0.02, or about 0.01 microns or less. The membranes may comprise different pore sizes, such that, for example the hydrophilic membrane may comprise a larger pore size than the hydrophobic membrane. Configuring the vents 440 in this fashion can allow air bubbles to escape a stream as it passes through the microfluidic cartridge, while still maintaining the fluid inside the microfluidic cartridge 410 pathway.

As described herein, the microfluidic cartridges 410 can be releasably coupled to the cassette 300. As illustrated in FIG. 4C, the microfluidic cartridge 410 can be releasably coupled to the cassette 300 via a tab 374 of the cassette. The tab 374 can allow the microfluidic cartridges 410 to snap into and snap out from the cassette 300 without the need of tools.

The microfluidic cartridges 410 may have a planar support that will typically be rectangular and can be made of any material compatible with a separation method, including silicon, glasses, hybrid materials or (preferably) polymers. The support will have a top surface and a bottom surface, one or both of which have at least one embedded channel extending from one or more sample inlets and one or more distinct fluid inlets, to one or more product outlets and one or more distinct waste outlets. Fluid inlets (as opposed to sample inlets) may sometimes be referred to as "buffer" or "wash" inlets and, depending on the objectives of a separation may be used to transport a variety of fluids into channels. Unless otherwise indicated by usage or context, it will be understood that a "fluid" may be a buffer, contain reagents, constitute growth medium for cells or generally be any liquid, and contain any components, compatible with operation of a device and the objectives of the user.

When fluid is applied to a device through a sample or fluid inlet, it flows through the channel toward the outlets, thereby defining a direction of bulk fluid flow. In order to separate cells or particles of different sizes, the channel includes an array of obstacles organized into one or more columns that extend longitudinally along the channel (from inlet to outlet), and rows that extend laterally across the channel. Each subsequent row of obstacles is shifted laterally with respect to the previous row, thereby defining an array direction that deviates from the direction of bulk fluid flow by a tilt angle (F). The obstacles are positioned so as to define a critical size such that when a sample is applied to an inlet of the microfluidic cartridge 410 and flows to an outlet, particles or cells in the sample larger than the critical size follow in the array direction and particles smaller than the critical size flow the direction of bulk fluid flow, thereby resulting in a separation.

Target Cells and Methods of Producing Target Cells

The systems and devices described herein may be used to otherwise isolate, purify, or enrich one or more target cells or a population of target cells from a suitable sample. The target cells can be isolated based upon a critical size or a critical diameter. Enriched cells may have a critical size greater than about 1, 2, 3, 4, 5, 6, 7, 8, 9, 10, 11, 12, 13, 14, 15 microns.

Setting an appropriate critical size may allow for the separation of certain cell types such as hematopoietic stem cells, peripheral blood mononuclear cells (PBMCs), white blood cells (WBCs or CD 45+ cells) or leukocytes, or other immune cells. Enriched cell populations may comprise one or more target cells selected from T cells (CD3+ cells), B cells (CD19+ cells), NK cells (CD56+ cells), or a combination thereof. Enriched T cell populations may comprise CD4+ T cells, CD8+ T cells or a combination thereof. T cells may exhibit a naïve, central memory, central memory effector or effector, or Temra phenotype. Enriched cell populations may be enriched such that a product obtained from the system is about 80%, 85%, 90%, 95%, 96%, 97%, 98%, or 99% pure for the particular cell type. In some cases, the resulting product is 80%, 85%, 90%, 95%, 96%, 97%, 98%, or 99% leukocytes. In specific examples, a leukapheresis product or leukopak may be applied to the system and/or device and a population of PBMCs that is at least 90%, 95%, 96%, 97%, 98%, or 99% PBMC cells may be obtained. Such purity may be determined by examining CD45 (pan-leukocyte marker) expression on obtained cells.

Such systems and devices described herein may also produce particle or leukocyte populations with high yield compared to an input population. For example, a sample may be applied to the device and a population of particles or cells that is at least 70%, 80%, 90%, 95%, 96%, 97%, 98%, or 99% of the particle or cell input may be obtained upon recovery. For example, a leukapheresis product may be applied to the device and a population of PBMCs that is at least 70%, 80%, 90%, 95%, 96%, 97%, 98%, or 99% of the PBMC input cells may be obtained upon recovery. For example, a leukapheresis product may be applied to the device and a population of T cells that is at least 70%, 80%, 90%, 95%, 96%, 97%, 98%, or 99% of the T cell input cells may be obtained upon recovery. Recovered one or more cell or particle populations may comprise an enriched product. The population of cells recovered may be 80%, 85%, 90%, 95%, 96%, 97%, 98%, 99%, or 100% viable upon recovery.

The enriched target cells may be subjected to one or more steps post collection from the device including culturing, expanding, cryopreserving, or genetically engineering. These processes may occur in vitro or ex vivo in a cell culture device, hood, or incubator. For example, the cells may be further cultured or expanded in vitro. Such steps can be used to produce a population of cells expressing a chimeric antigen receptor, a recombinant T cell receptor, or another therapeutic protein. For example, such steps can render the cells transgenic with an exogenous nucleic acid configured to encode a chimeric antigen receptor or a recombinant T cell receptor. Such cells may be genetically engineered by one or more steps comprising use of viral transduction, electroporation, or chemical transfection reagents (e.g., cationic lipids, calcium chloride precipitation). Viral transduction may occur using a lentiviral vector, retroviral vector, or adenoviral vector. The chimeric antigen receptor may comprise Tisagenlecleucel, Axicabtagene ciloleucel, or a combination thereof. The chimeric antigen receptor may comprise one or a combination of sequences that may facilitate a cellular recognition event, such as MART-1, CD444v6, CAIX, CEA, CD133, c-Met, EGFR, EGFRvIII, Epcam, EphA2, FR alpha, GD2, GPC3, GUCY2C, HER1, HER2, ICAM-1, IL13R alpha 2, I11IR alpha, Kras, Kras G12D, L1CAM, MAGE, MET, Mesothelin, MUC1, MUC16 ecto, NKG2D, NY-ESO-1, PSCA, or WT-1.

Described herein are methods of producing a product comprising particles, including cells, by flowing a sample through a system or device. In some cases, the system is a microfluidic system. In some embodiments, the microfluidic system comprises a cassette or cartridge that separates one or more particles from the system or device. In some cases, the system comprises a cassette to which one or more microfluidic cartridges are releasably coupled and supported. In some cases, the cassette is primed by flowing a priming solution though the system. The methods may involve processing the sample by flowing the sample through the system and using the one or more microfluidic cartridges to separate one or more target particles from the system. Product can be collected comprising one or more target particles that have been separated from the system or device. In some cases, the sample has a volume of at least about 40 mL. In some cases, the product is enriched with at least about 70% recovery of the one or more target particles. In some cases, the method is achieved in a closed sterile setting that is continuously inline. In some embodiments, the method is performed in less than or equal to 1 hour.

Described herein are methods of obtaining an enriched cellular product or population of cells comprising flowing or processing a blood-related sample through a microfluidic device to produce an enriched cellular product that comprises at least 90% of the WBCs from the sample, and fewer than 5% of the red blood cells and fewer than 5% of the platelets from the sample. In some embodiments, the method processes the blood related sample at a flow rate of 300 mL/hr. In some embodiments, the method has a maximum cell throughput of $30\times10^9$ cells/hr.

Described herein are methods of obtaining an enriched cellular product or population of cells comprising of flowing or processing a blood-related sample through a device or system described herein. In some embodiments, the method comprises producing a product that contains target cells comprising leukocytes. In some methods, the leukocyte product is at least about 95% pure.

In some cases, the sample is processed at a rate of at least about 10 mL/hr, 30 mL/hr, 100 mL/hr, 150 mL/hr, 200 mL/hr, 300 mL/hr, 400 mL/hr, 500 mL/hr, 600 mL/hr, or 700 mL/hr. In some embodiments, the sample is processed with a cell throughput of at least about $1\times10^8$ cells/hr, $10\times10^8$ cells/hr, $30\times10^8$ cells/hr, $10\times10^9$ cells/hr, $30\times10^9$ cells/hr, or $100\times10^9$ cells/hr. In some cases, the product is enriched with particles having a diameter of at least about 4, 5, 6, 7, 8, 9, 10, 11, 12, or 13 microns. In some cases, the wash efficiency of the methods described herein are greater than at least 1 log, 2 log, 3 log, 3.3 log, 4 log, or 5 log. In some cases, the methods described herein produce a dose equivalent of therapeutic lymphocytes within 1, 2, 3, 4, 5, 6, 7, 8, 9, 10, 11, 12, 13, or 14 days. In some embodiments, the methods described herein produce cell populations from a single leukopak that are able to produce more dose equivalents of therapeutic lymphocytes than cells produced using ficoll or other methods. In some cases, the methods described herein produce cell populations that are able to produce at least about 2-fold, 2.5-fold, 3-fold, 4-fold, 5-fold, 7-fold, 10-fold, or 20-fold more dose equivalent of therapeutic lymphocytes than cells produced using ficoll or other methods. For example, it has been shown that DLD methods produce cell population that produce 2-fold more dose equivalents of therapeutic lymphocytes than cells produced using ficoll or other methods. See FIG. 20.

Other methods of operating the devices described herein comprise applying a heterogeneous sample to one or more inlets and obtaining a target cell population from one or more outlets enriched for one or more target cells. In specific examples, the method comprises applying a sample comprising a heterogenous cell population with a volume of 100 mL, 200 mL, 300 mL and 400 mL or more and collecting a population enriched for one or more target cells. For example, at least 100 mL of a leukapheresis product may be applied to one or more inlets of the device and a cell population that is greater than about 90% PBMC may be obtained from one or more outlets of the device. In certain embodiments, the sample can be processed in one hour or less.

In some embodiments, the methods are completed in about 10 minutes, 20 minutes, 30 minutes, 40 minutes, 50 minutes, an hour, two hours, three hours, or less. In some cases, the method uses a cartridge or cassette configured for a single use or multiple uses.

In some cases, the sample is a human sample and comprises human cells of certain cell types such as hematopoietic stem cells, red blood cells, platelets, peripheral blood mononuclear cells (PBMCs), white blood cells (WBCs or CD 45+ cells) or leukocytes, or other immune cells. In some cases, the sample volume is at least about 20 mL to about 500 mL. In some cases, the sample volume is at least about 20 mL to about 40 mL, about 20 mL to about 100 mL, about 20 mL to about 200 mL, about 20 mL to about 300 mL, about 20 mL to about 400 mL, about 20 mL to about 500 mL, about 40 mL to about 100 mL, about 40 mL to about 200 mL, about 40 mL to about 300 mL, about 40 mL to about 400 mL, about 40 mL to about 500 mL, about 100 mL to about 200 mL, about 100 mL to about 300 mL, about 100 mL to about 400 mL, about 100 mL to about 500 mL, about 200 mL to about 300 mL, about 200 mL to about 400 mL, about 200 mL to about 500 mL, about 300 mL to about 400 mL, about 300 mL to about 500 mL, or about 400 mL to about 500 mL. In some cases, the sample volume is at least about 20 mL, about 40 mL, about 100 mL, about 200 mL, about 300 mL, about 400 mL, or about 500 mL. In some cases, the sample volume is at least about at least about 20 mL, about 40 mL, about 100 mL, about 150 mL, about 200 mL, about 300 mL, or about 400 mL. In some cases, the sample volume is at least about at most about 40 mL, about 100 mL, about 200 mL, about 300 mL, about 400 mL, or about 500 mL.

Figure 11:
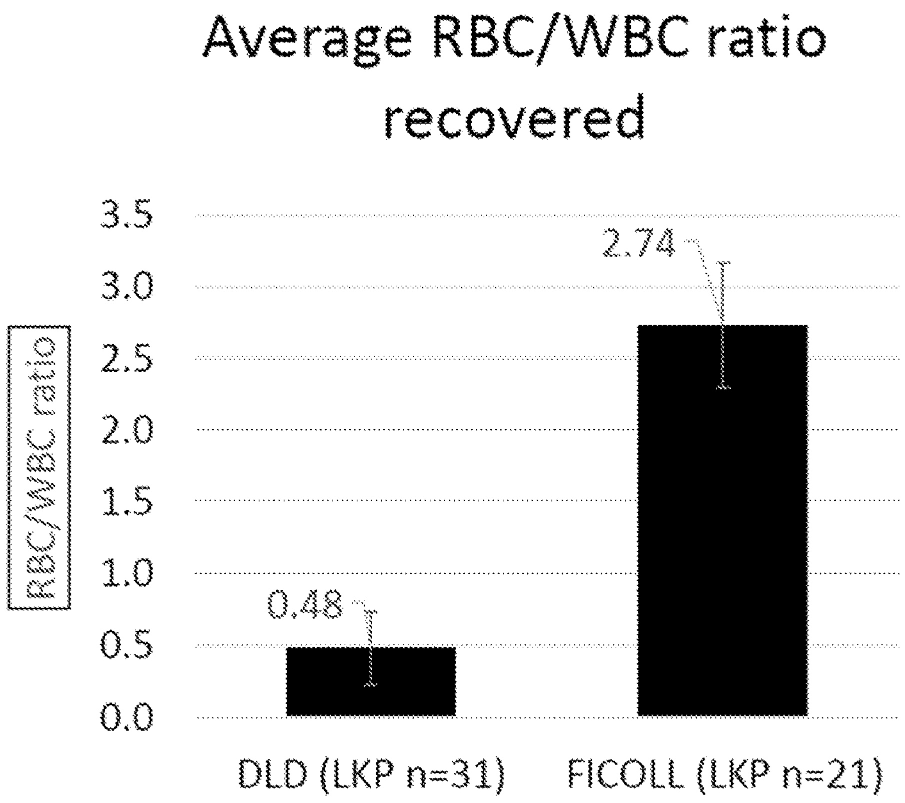
FIG. 11 illustrates that cells enriched according to the systems and methods herein have fewer platelets (A) and red blood cells.
Figure 11:
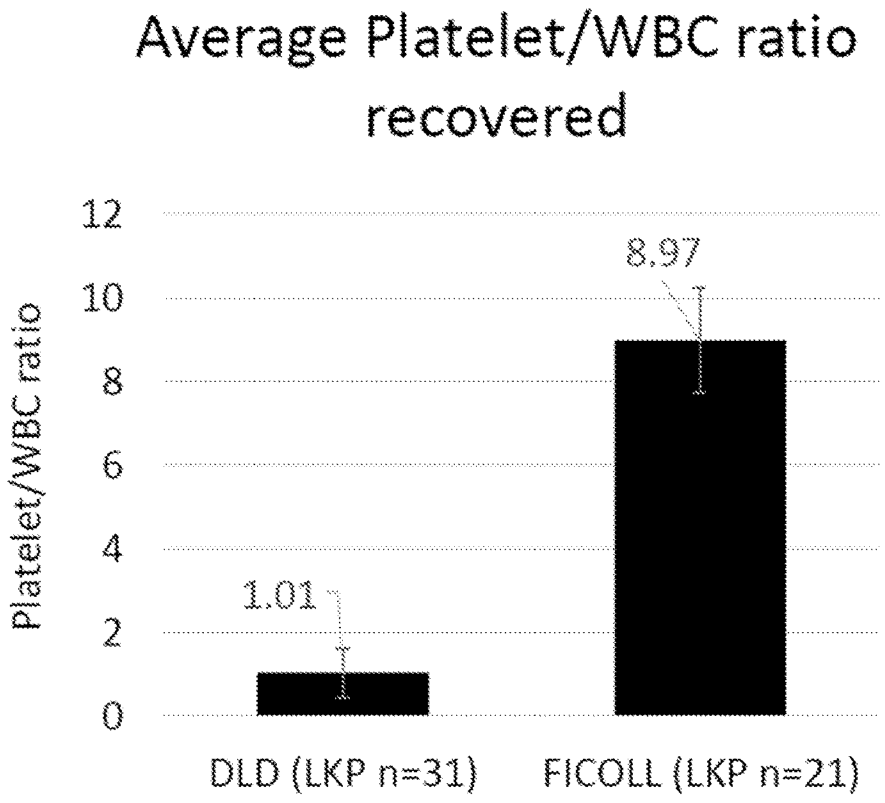

In some cases, the sample may be applied to the device and an enriched target cell product may be obtained by subjecting a blood related product to remove target particles from the sample. In some cases, removing target particles comprises simultaneously depleting red blood cells and platelets. The sample may be applied to the device and an enriched target cell product may be obtained by subjecting a blood related product to depletion of platelets and by maintaining red blood cells. The red blood cells may be maintained at a ratio of red blood cells to target cells less than about 0.2:1, 0.5:1, 0.7:1, 1:1, 2:1, 2.5:1, 3:1, 5:1, 10:1, 25:1, 50:1, 100:1, 150:1, 200:1, 250:1, or 500:1 or greater. See FIG. 11. The platelet cells may be depleted to achieve a ratio of platelet cells to target cells less than about 0.7:1, 1:1, 2:1, 2.5:1, 3:1, 5:1, 8:1, 9:1, 25:1, 50:1, 100:1, 150:1, 200:1, 250:1, or 500:1 or less. See FIG. 11. The target cells may be peripheral blood monocular cells, CD3+ T cells, CD4+ T cells, or CD8+ T cells. Such separations may be achieved by configuring the system to allow enrichment of cells above a critical size of about 1, 2, 3, 4, 5, 6, 7, 8, 9, 10, 11, 12, 13, 14, or 15 microns. In some cases, at least about 50%, 60%, 70%, 80%, 85%, 90%, 95%, 96%, 97%, 98%, or 99% of the red blood cells are removed from the sample. In some cases, at least about 50%, 60%, 70%, 80%, 85%, 90%, 95%, 96%, 97%, 98%, or 99% of the platelets are removed from the sample. In some cases, the product comprises a smaller ratio of red blood cells to leukocytes, platelets to leukocytes, or a combination thereof, as compared to a population of cells obtained by using a density gradient centrifugation method.

The systems and methods described herein allow for greater recovery/less waste of target cell populations, and also for cell populations with contamination by unwanted cell types such as platelets and/or red blood cells. Also, because cells are not packed together under high speed sedimentation, the system promotes cell-cell interactions that may be advantageous, such as lymphocyte-RBC interactions; while reducing interactions that may be deleterious, such as platelet-lymphocyte interactions. The system also reduces lysis of platelets and leukocytes and rosetting of red blood cells, which reduces soluble mediators that may be deleterious for target cell populations (e.g., by promoting activation or differentiation) such as leukocytes, B cells, T cells, naïve T cell, central memory T cells, and NK cells.

The systems and method described herein may recover leukocytes (WBCs) to a purity of 80%, 85%, 90%, 95% or greater. The systems and method described herein may deplete platelets by 75%, 80%, 85%, 90%, 95% or more. The systems and method described herein may deplete red blood cells by 75%, 8%, 85%, 90%, 95% or more. In certain embodiments, the systems and method described herein produce cell populations that possess at least about 1.5-fold, 2-fold, 2.5-fold, 3-fold, or 4-fold, 5-fold, 10-fold, or 20-fold fewer red blood cells, platelets, or a combination thereof when compared to ficoll or other methods. See FIG. 11. Similarly, the methods described herein may outperform ficoll or other methods in producing fewer red blood cells or platelets when the sample is that from a cancer patient. See FIG. 16.

TABLE 1

Measures of recovery and depletion of certain cell types using the DLD system

| Feature | Details |
|---|---|
| Sample processing rate | 300 mL/hr |
| Maximum cell throughput | $30 \times 10^9$ cells/hr |
| Cell size | >4 μm |
| Cell type | leukocytes |
| WBC recovery† | >90% |
| RBC removal** | >95% |
| Platelet removal | >95% |
| Wash efficiency | >3.3 log |

*Average cell throughput is 400 mL/hr for leukopaks up to $100 \times 10^6$ cell/mL resulting in $40 \times 10^9$ cells processed per hour. The DLD System has successfully supported $150 \times 10^6$ cells/mL.

**relative to a whole-blood sample.

†Timed fluid flush enables removal of remaining cells from tubing into product; nominal tubing volume ≤8 mL.

The methods and systems described herein can produce target cell populations that have an equal or greater capacity for expansion in vitro after enrichment. The cell isolated by the methods and systems described herein can lead to decreased doubling time and/or a greater amount of doublings compared to current systems and methods that use density gradient media and centrifugation (e.g., a density gradient method, a density gradient media method, a density gradient centrifugation method, e.g. Ficoll or ficoll e.g., Ficoll®, GE Healthcare) for separation and cell isolation.

Figure 10:
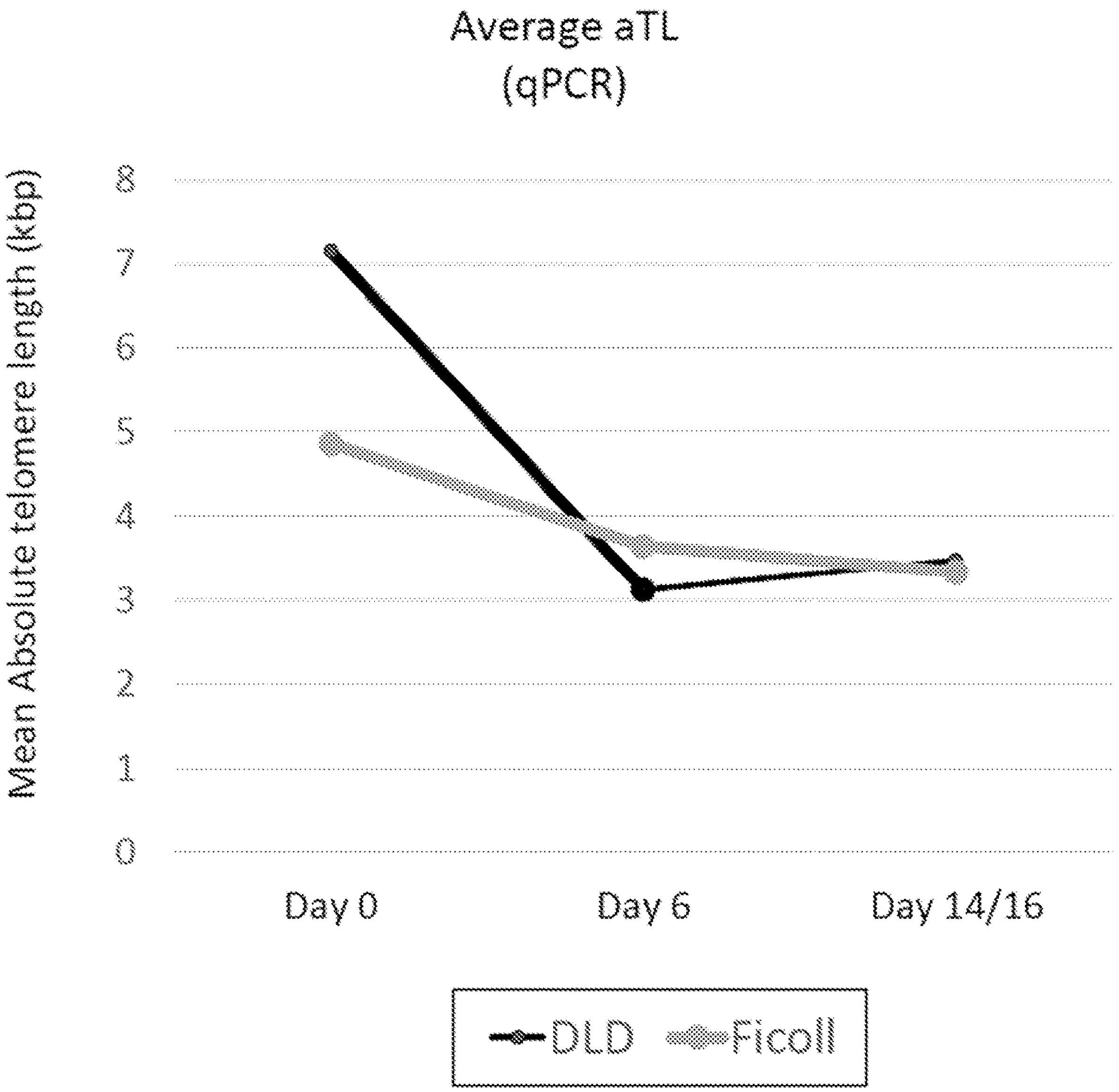
FIG. 10 illustrates that cells enriched according to the systems and methods herein possess longer Telomere length compared to Ficoll, indicating greater expansion capability. Assay was conducted using qPCR analysis for absolute Telomere Length (aTL).

In certain embodiments, the systems and method described herein produce target cell populations that have an increased doubling/expansion capacity compared to density gradient separation. The cells may be able to undergo 1, 2, 3, 4, 5, 6, 7, or more doublings in vitro compared to separation by density gradient centrifugation (e.g., ficoll). In certain embodiments, doubling capacity is indicated by telomere length. In certain embodiments, cells enriched by the systems and methods described herein have an average telomere length equal to or greater than least about 4 or at least about 5 kilobases. In certain embodiments, cells enriched by the systems and methods described herein have an average telomere length equal to or greater than 6 kilobases. In certain embodiments, cells enriched by the systems and methods described herein have an average telomere length equal to or greater than 7 kilobases. See FIG. 10.

Figure 12:
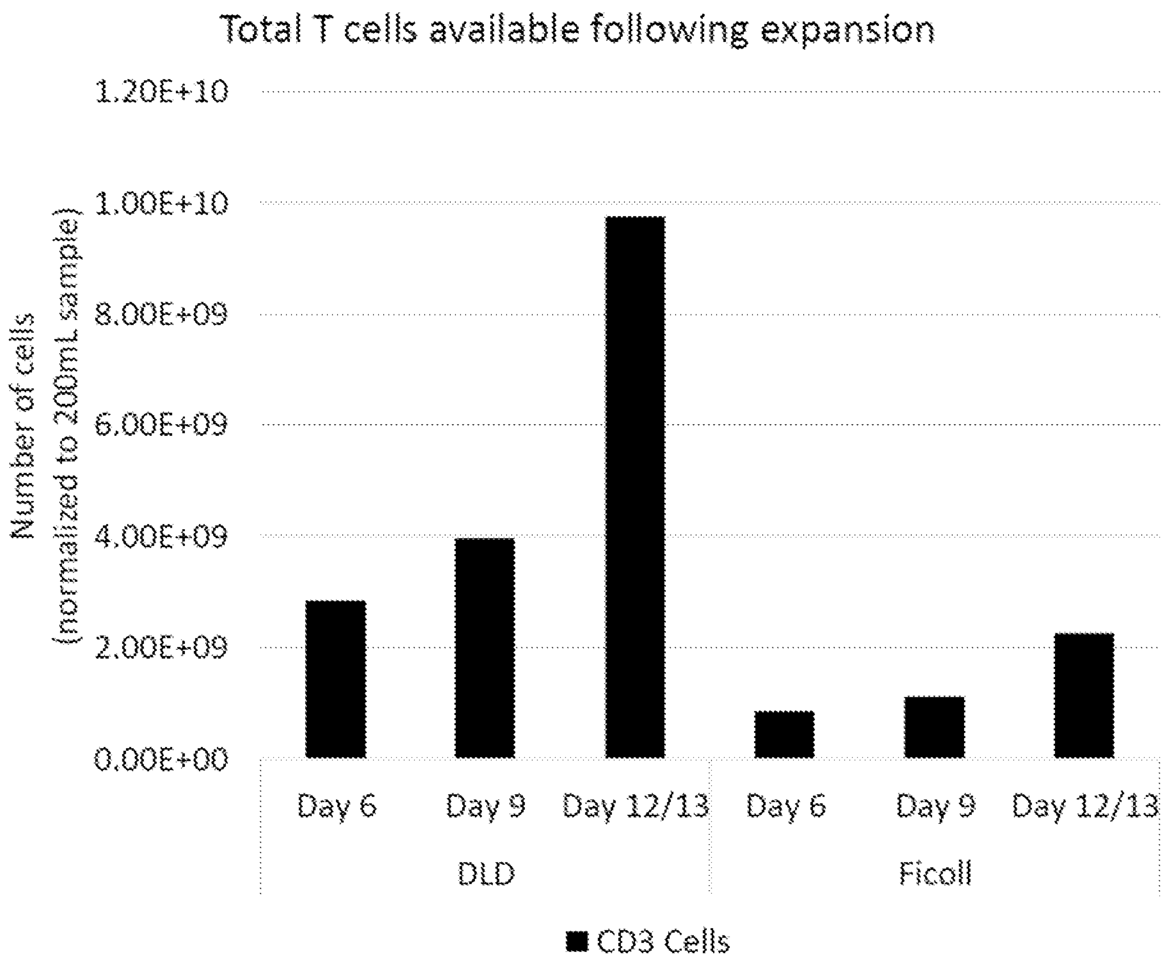
FIG. 12 illustrates that cells enriched according to the systems and methods herein produce more cells after culture when compared to ficoll. Following processing T cells were activated and selected using magnetic CD3/28 beads. Cells were plated at a density of $1\times10^6$/mL in TexMACS media supplemented with 5 ng/mL of both TL-7 and IL-15.

The greater doublings and/or reduced doubling times can produce target cell populations at an earlier time-point compared to other methods, which is useful for downstream therapeutic applications. In certain embodiments, target cell populations can achieve a total number of cells that is at least about $2\times10^9$, about $3\times10^9$, about $4\times10^9$, about $5\times10^9$, about $9\times10^9$, about $1\times10^{10}$, about $5\times10^7$, or about $1\times10^8$ immediately after isolation (e.g., day 0) from a whole-blood sample, apheresis product, or a single leukopak of about 100 mL, 200 mL, 300 mL, 400 mL, or 500 mL. See FIG. 13. In certain embodiments, target cell populations can achieve a total number of cells that is at least about $1\times10^9$, about $5\times10^9$, about $1\times10^{10}$, $2\times10^{10}$, $5\times10^7$, or $1\times10^8$, within about 3, 5, 6, 7, 8, 9, 10, 11, 12, 13, 14 days or less from a whole-blood sample, apheresis product, or a single leukopak of about 100 mL, 200 mL, 300 mL, or 400 mL. See FIG. 12. In certain embodiments, the target cells are peripheral blood mononuclear cells. In certain embodiments, the target cells are T cells. In some cases, the T cells are naïve T cells, unactivated T cells (CD25−), or central memory T cells derived from a leukopak or other apheresis product.

The methods and systems described herein can produce target cell populations that have a greater capacity to be transduced by virus after enrichment. The cell isolated by the methods and systems described herein can lead to greater efficiency of viral transduction compared to current systems and methods that use density gradient media (e.g., ficoll) for separation.

In certain embodiments, the systems and method described herein produce cell populations that have greater efficiency for viral transduction compared to density gradient separation. The cells may be able to be transduced such that the transduction efficiency after separation is at least 60%, 70%, 80%, or 90% or more.

Figure 8:
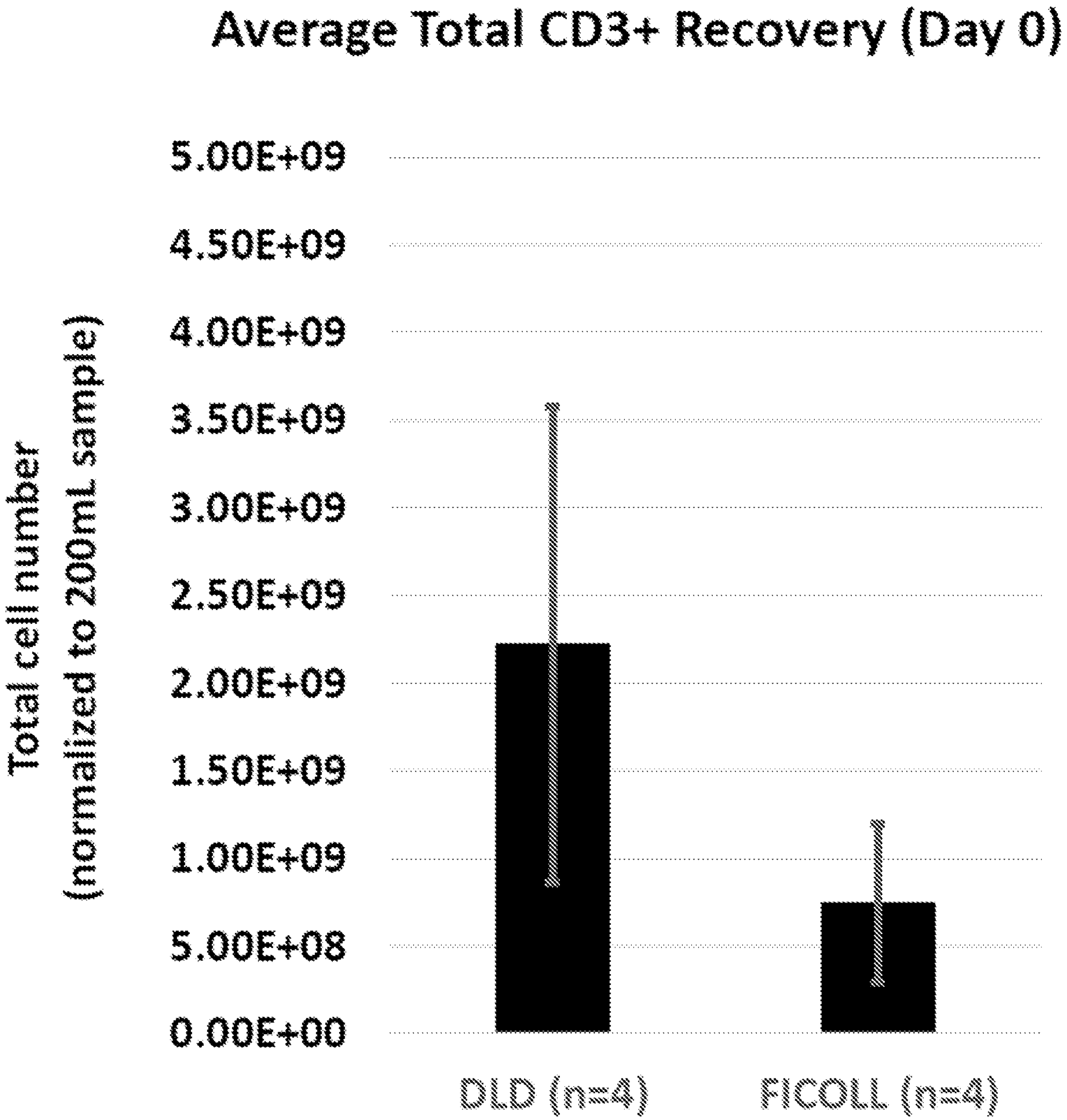
FIG. 8 illustrates improved recovery of CD3+ T cells from leukopaks enriched according to the systems and methods herein compared to Ficoll.

In certain embodiments, the systems and method described herein produce cell populations that possess at least about 1.5-fold, 2-fold, 2.5-fold, 3-fold, or 4-fold, 5-fold, or 6-fold more leukocytes when compared to ficoll or other methods. In some cases, leukocytes comprise CD 3+ cells, CD 45+ cells, CD 4+ cells, CD4+ naïve cells, CD 4+ memory cells, CD 4+ effector cells, CD 8+ cells, CD 8+ naïve cells, CD 8+ effector cells, CD 8+ memory cells, memory cells, effector cells, naïve cells, Temra cells, or any combination thereof. In certain embodiments, the systems and method described herein produce cell populations that possess at least about 1.5-fold, 2-fold, 2.5-fold, 3-fold, or 4-fold, 5-fold, or 6-fold more CD 3+ T cells when compared to ficoll or other methods. See FIG. 8. In certain embodiments, the systems and method described herein produce cell populations that possess at least about 1.5-fold, 2-fold, 2.5-fold, 3-fold, or 4-fold, 5-fold, or 6-fold more CD 45+ T cells when compared to ficoll or other methods. For example, the uses of a DLD method has been shown to produce about 2.5-fold more CD 45+ cells, or white blood cells, than Ficoll methods. See FIG. 13.

Figure 9A:
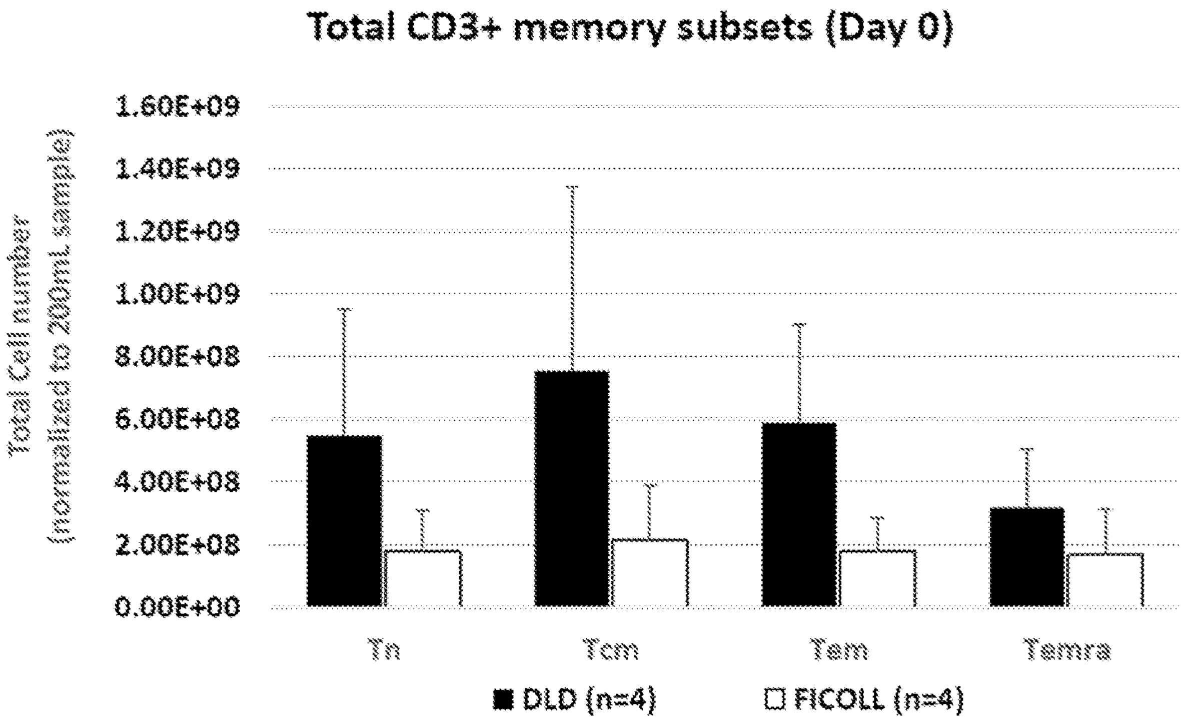
FIG. 9A-9B illustrates improved recovery of certain advantageous cell subsets from leukopaks enriched according to the systems and methods herein compared to Ficoll.

In certain embodiments, the systems and method described herein produce cell populations that possess at least about 2-fold, 3-fold, or 4-fold more central memory T lymphocytes (CD45RO+CD62L+ or CD45RO+CCR7+) when compared to ficoll or other methods. See Table 2 and FIG. 9A.

In certain embodiments, the systems and method described herein produce cell populations that possess at least about 2-fold, 3-fold, or 4-fold more naive T lymphocytes (CD25RA+ or CD25−) when compared to ficoll or other methods. See Table 2.

Figure 9B:
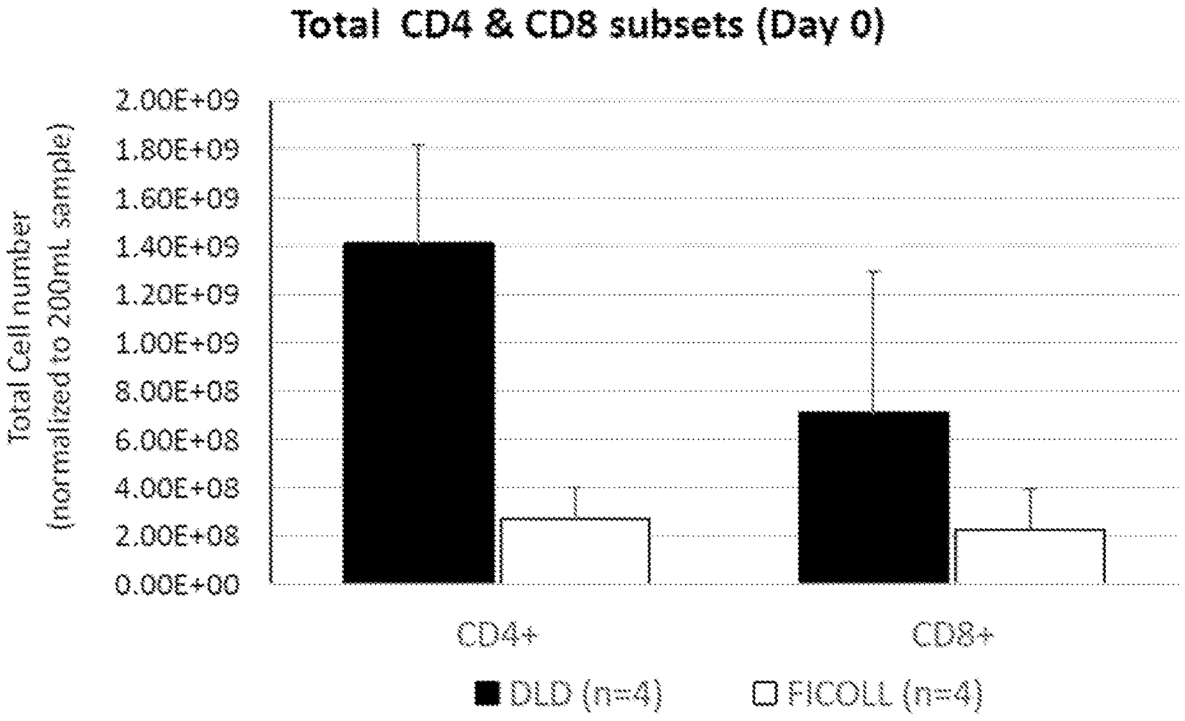

In certain embodiments, the systems and method described herein produce cell populations that possess at least about 1.5-fold, 2-fold, 2.5-fold, 3-fold, or 4-fold, or 5-fold more CD 4+, CD 8+ T, or a combination thereof, lymphocytes when compared to ficoll or other methods. See Table 2 and FIG. 9B. In some cases, the CD 4+ or CD 8+ T lymphocytes are unactivated, naïve, central memory or memory, effector, or Temra subtypes. In some further embodiments, the leukocytes or lymphocytes are derived or obtained from a sample taken from healthy patients. In other examples, they are taken from cancer patients. In some cases, the cancer patients have breast cancer, lymphoma, leukemia, -Hodgkin's lymphoma, colorectal, skin cancer, or other cancer. In some cases, samples taken from a cancer patient have reduced white blood cell counts. In some embodiments, the methods described herein produce cell populations from cancer patients with reduced WBC counts that possess at least about 1.5-fold, 2-fold, 2.5-fold, 3-fold, or 4-fold, 5-fold, or 10-fold more CD 3+, CD 4+, CD 8+, CD 45+, or a combination thereof, lymphocytes or leukocytes when compared to ficoll or other methods. For example, it has been shown that DLD methods are able to produce 5-fold more CD 45+ cells and 2.5-fold more CD 3+ cells than ficoll or other methods when using the same volume from the same cancer patients with reduced WBC counts. See FIG. 15.

TABLE 2

| Deterministic Lateral displacement (DLD)/Ficoll fold Advantage for each identified population | | | | | |
|---|---|---|---|---|---|
| Tn | Tcm | Tem | Temra | CD4+ | CD8+ |
| 3.05 | 3.53 | 3.28 | 1.91 | 5.21 | 3.16 |

Tn = naïve T cells;
Tcm = central memory T cells;
Tem = effector memory T cells

Figure 22:
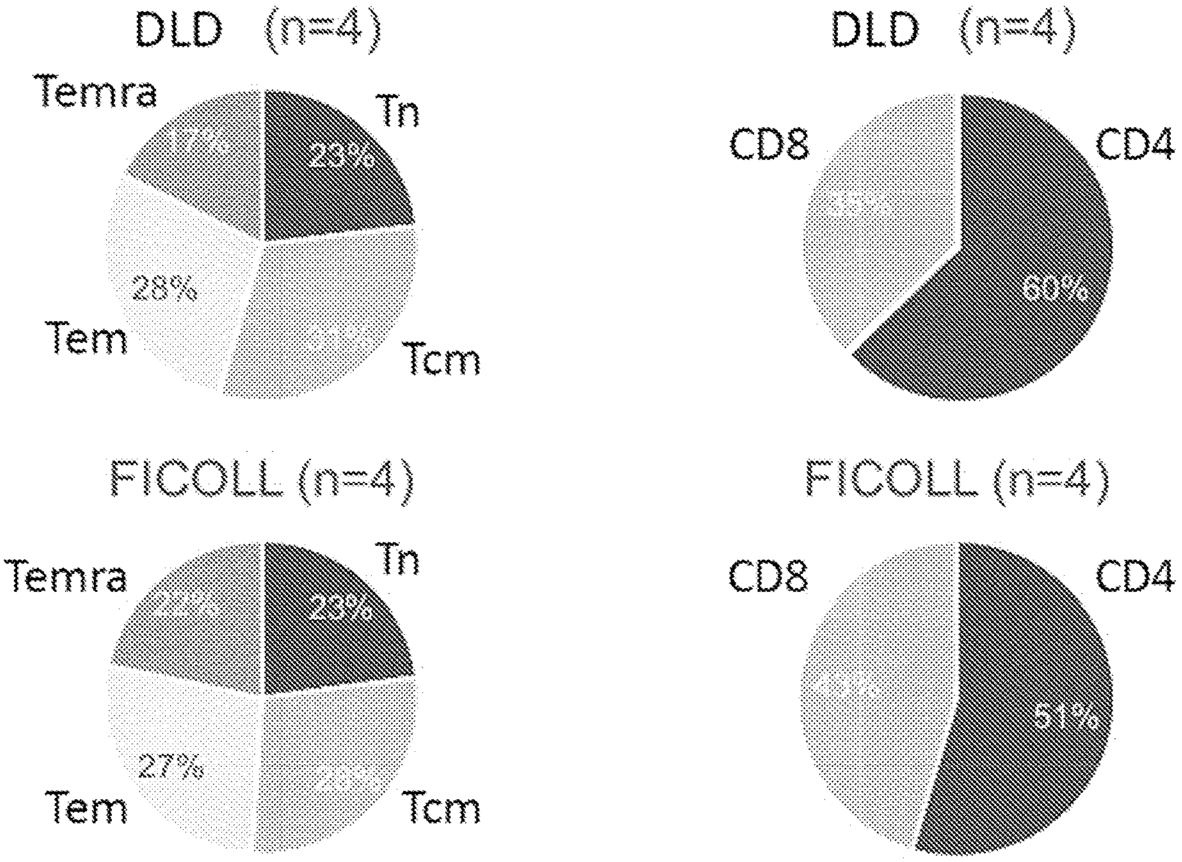
FIG. 22 illustrates that systems and methods herein recover more of the less differentiated naïve and central memory subsets from normal donor leukopaks and result in fewer terminally differentiated cells compared to Ficoll preparations.

In certain embodiments, the systems and method described herein recover a high percentage of naïve, central memory, or CD 4+ T cells. Recovery of naive, central memory, or CD4+ T cells is increased compared to other systems such as density gradient separation. In some embodiments, the methods described herein produce at least about 2-fold, 2.5-fold, 3-fold, 4-fold, 5-fold, or 10-fold more naïve or less differentiated cells than those produced from other systems such as density gradient separation. For example, it has been shown that DLD systems and methods produce at least about 3-fold more naïve and central memory T cells as compared to Ficoll methods. See Table 2. This includes when the sample is taken from healthy donors on the same day the method is performed. In certain embodiments, the systems and method described herein recover at least about 50%, about 60%, about 70%, about 80% about 90%, about 95%, about 97%, about 98%, or about 99% naïve T cells compared to an unenriched sample such as from a whole-blood sample, apheresis product or leukopak of about 100 mL, 200 mL, 300 mL, or 400 mL. In some examples, the methods described herein produce more naïve and central memory T cells relative to effector and Temra cells than cells produced using other methods such as Ficoll. For example, it has been shown that DLD methods produce slightly more naïve and central memory T cells relative to effector and Temra cells than cells produced using other methods such as Ficoll. See FIG. 14. This is also the case when using samples taken from healthy donors. See FIG. 22.

In certain embodiments, the methods described herein produce a population of cells that exhibit an increase in one or more biological properties when compared to a population of cells produced by a density gradient centrifugation method. In certain embodiments, the methods described herein produce a population of cells that exhibit a decrease in one or more biological properties when compared to a population of cells produced by a density gradient centrifugation method. Biological properties include the ability to readily integrate a lentiviral vector, ability to expand in culture, ability to retain T cell memory composition while in cell culture, receptivity to viral transduction, differences in average telomere length, ability to retain a relative population of less differentiated naïve and central memory cells, cytotoxic killing capacity, IFN gamma expression/secretion, GM-CSF expression/secretion, TNF-a expression/secretion, viability, time required to expand in culture to produce a single therapeutic dose equivalent of cells, time required to express a gene delivered by a vector, relative population of effector or Temra cells, IL-1Ra expression/secretion, IL-6 expression/secretion, IL-13 expression/secretion, MCP-1 expression/secretion, PD1 and/or Tim3 expression, cell senescence or exhaustion, potential to trigger cytokine release syndrome, time in culture required before being delivered to a patient. For example, it is shown herein that DLD methods produce cell populations with preferable cytokine expression profiles compared to cells produced using ficoll methods and reduce the potential to trigger cytokine release syndrome. See FIGS. 26-28. In general, DLD methods and the methods described herein exhibit a number of favorable increases or decreases in biological properties for the production, delivery, efficacy, and safety of therapeutic lymphocytes. See FIG. 29.

In some cases, the methods described herein produce a population of cells that exhibits an increased ability to expand in culture, wherein the cells are expanded before or after being genetically modified when compared to a population of cells produced by a density gradient centrifugation method. In some cases, the population of cells exhibits at least about 1.1-fold, 1.5-fold, 2-fold, 3-fold, 4-fold, 5-fold, or 10-fold increase in ability to expand in culture, wherein the cells are expanded before or after being genetically modified when compared to a population of cells produced by a density gradient centrifugation method.

In some cases, the methods described herein produce a population of cells that exhibit an increase in ability to readily integrate a lentiviral vector (i.e. at least some portion of the nucleic acid of the lentivirus is inserted into the cells' genomes or exosomes) when compared to a population of cells produced by a density gradient centrifugation method. In some cases, the population of cells exhibit at least about 5%, 10%, 15%, 25%, 30%, 50%, 100%, 200%, 300%, 400%, or 500% increased ability to readily integrate a lentiviral vector when compared to a population of cells produced by a density gradient centrifugation method. In some examples, it has been shown that the methods described herein produce a population of cells that have a 30% increased ability to readily integrate lentivirus. See FIG. 17.

In some cases, the methods described herein produce a population of cells that exhibit an increase in ability to retain T cell memory composition while in cell culture when compared to a population of cells produced by a density gradient centrifugation method. In some cases, the population of cells retains its relative T cell memory composition for at least about 1, 2, 3, 4, 5, 6, 7, 8, 9, 10, 11, 12, 13, 14, 15, 16, 17, 18, 19, or 20 days longer than a population of cells produced by a density gradient centrifugation method. For example, it has been shown that DLD methods produce cell populations that retain their relative memory T cell populations longer than other methods including ficoll. See FIG. 23.

In some cases, the methods described herein produce a population of cells that exhibit an increase in receptivity to viral transduction when compared to a population of cells produced by a density gradient centrifugation method. In some cases, the population of cells exhibit at least about 5%, 10%, 15%, 25%, 30%, 50%, 100%, 200%, 300%, 400%, or 500% increased receptivity to viral transduction when compared to a population of cells produced by a density gradient centrifugation method. For example, it has been shown that DLD methods produce a population of cells that are about between 20-40% more receptive to viral transduction than cells produced using ficoll or other methods. See FIG. 19.

In some cases, the methods described herein produce a population of cells that exhibit an increase in telomere length when compared to a population of cells produced by a density gradient centrifugation method. In some cases, the population of cells exhibit at least about 5%, 10%, 15%, 25%, 30%, 50%, 100%, 200%, 300%, 400%, or 500% increased telomere length when compared to a population of cells produced by a density gradient centrifugation method.

In some cases, the methods described herein produce a population of cells that exhibit an increase in ability to retain a relative population of less differentiated naïve and central memory cells while in cell culture when compared to a population of cells produced by a density gradient centrifugation method. In some cases, the population of cells retains its relative population of less differentiated naïve and central memory cells while in cell culture for at least about 1, 2, 3, 4, 5, 6, 7, 8, 9, 10, 11, 12, 13, 14, 15, 16, 17, 18, 19, or 20 days longer than a population of cells produced by a density gradient centrifugation method.

In some cases, the methods described herein produce a population of cells that exhibit an increase in functional killing capacity when compared to a population of cells produced by a density gradient centrifugation method. In some cases, the population of cells exhibit at least about 5%, 10%, 15%, 25%, 30%, 50%, 100%, 200%, 300%, 400%, or 500% increased functional killing capacity when compared to a population of cells produced by a density gradient centrifugation method. For example, it has been shown that DLD methods produce cells that have at least 30% greater killing capacity as compared to cells produced using ficoll methods, when seeded at 2 cells per targeted cell for killing. See FIG. 25.

In some cases, the methods described herein produce a population of cells that exhibit an increase in IFN gamma expression when compared to a population of cells produced by a density gradient centrifugation method. In some cases, the population of cells exhibits at least about 1.1-fold, 1.5-fold, 2-fold, 3-fold, 4-fold, 5-fold, or 10-fold increase in IFN gamma expression when compared to a population of cells produced by a density gradient centrifugation method. In some cases, the increase in IFN gamma expression is apparent 0, 3, 6, 9, 13, or 16 days after being produced by the methods and systems described herein.

In some cases, the methods described herein produce a population of cells that exhibit an increase in GM-CSF expression when compared to a population of cells produced by a density gradient centrifugation method. In some cases, the population of cells exhibits at least about 1.1-fold, 1.5-fold, 2-fold, 3-fold, 4-fold, 5-fold, or 10-fold increase in GM-CSF expression when compared to a population of cells produced by a density gradient centrifugation method. In some cases, the increase in GM-CSF expression is apparent 0, 3, 6, 9, 13, or 16 days after being produced by the methods and systems described herein.

In some cases, the methods described herein produce a population of cells that exhibit an increase in TNFa expression when compared to a population of cells produced by a density gradient centrifugation method. In some cases, the population of cells exhibits at least about 5%, 10%, 15%, 25%, 30%, 50%, 100%, 200%, 300%, 400%, or 500% increase in TNFa expression when compared to a population of cells produced by a density gradient centrifugation method. In some cases, the increase in TNFa expression is apparent 0, 3, 6, 9, 13, or 16 days after being produced by the methods and systems described herein.

In some cases, the methods described herein produce a population of cells that exhibit an increase in viability when compared to a population of cells produced by a density gradient centrifugation method. In some cases, the population of cells exhibits at least about 5%, 10%, 15%, 25%, 30%, 50%, 100%, 200%, 300%, 400%, or 500% increase in viability when compared to a population of cells produced by a density gradient centrifugation method.

In some cases, the methods described herein produce a population of cells that exhibit an increase in ability to readily integrate a lentiviral vector when compared to a population of cells produced by a density gradient centrifugation method.

In some cases, the methods described herein produce a population of cells that exhibit a decrease in time required to expand in culture to produce a single therapeutic dose equivalent of cells when compared to a population of cells produced by a density gradient centrifugation method. In some cases, the population of cells require about 1, 2, 3, 4, 5, 6, 7, or 8 fewer days to expand in culture to produce a single therapeutic dose equivalent of cells when compared to a population of cells produced by a density gradient centrifugation method.

Figure 18:
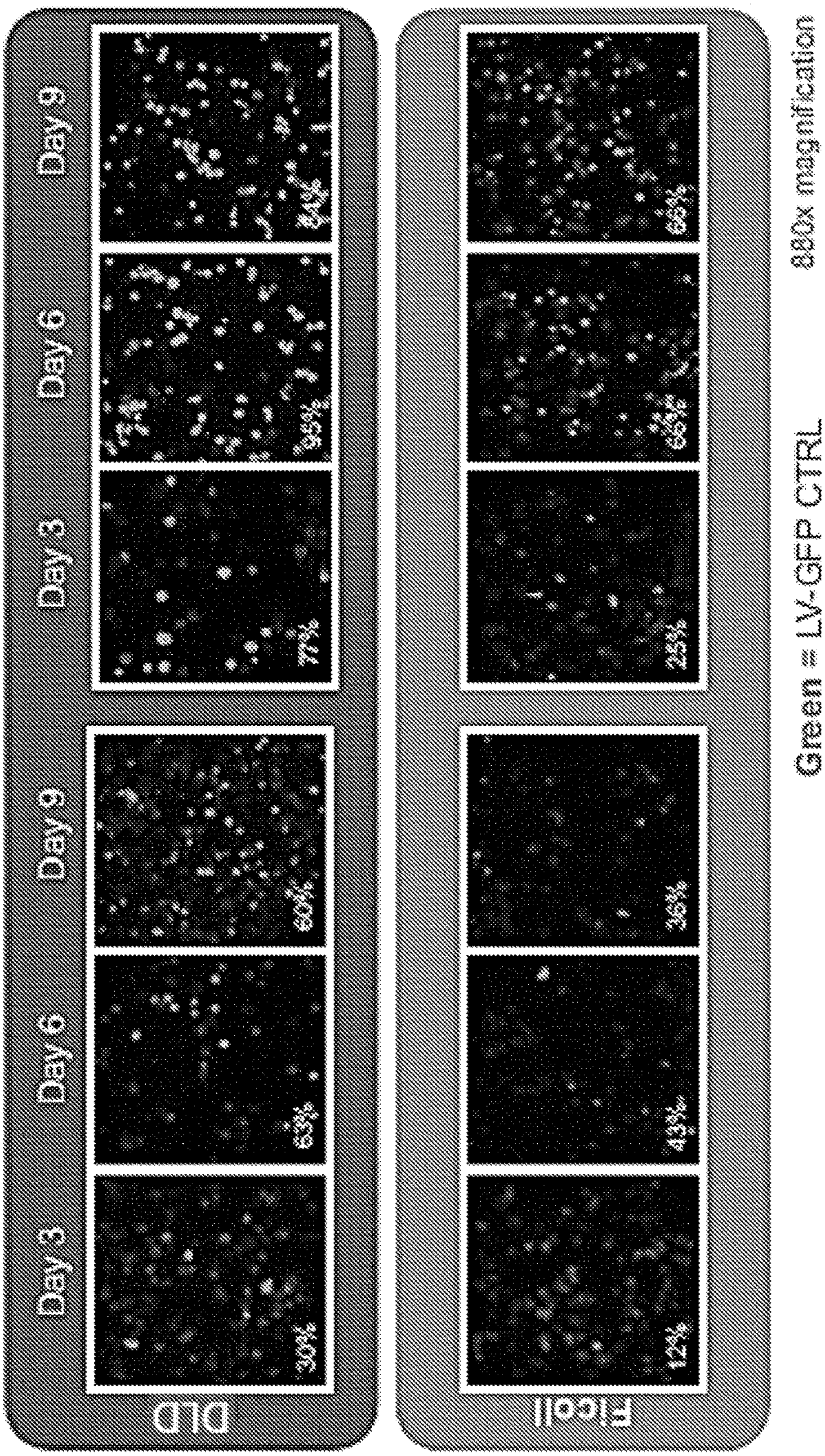
FIG. 18 illustrates that cells enriched according to the systems and methods herein integrate lentivirus more readily and express reporter genes at an earlier timepoint compared to Ficoll preparations.

In some cases, the methods described herein produce a population of cells that exhibit a decrease in time required to express a gene delivered by a vector when compared to a population of cells produced by a density gradient centrifugation method. In some cases, the population of cells require about 1, 2, 3, 4, 5, 6, 7, or 8 fewer days to express a gene delivered by a vector when compared to a population of cells produced by a density gradient centrifugation method. For example, it has been shown that DLD methods produce cell populations that express a gene delivered by a vector faster than ficoll or other methods. See FIG. 18.

Therapeutic dose equivalents may vary depending on the exact type of therapeutic but in some cases may be a at least about $1\times10^7$, $2\times10^7$, $3\times10^7$, $4\times10^7$, $5\times10^7$, $1\times10^8$, $2\times10^8$, $3\times10^8$, $4\times10^8$, $5\times10^8$, $1\times10^9$, $2\times10^9$, $3\times10^9$, $4\times10^9$, or $5\times10^9$ total cells. Therapeutic doses may be about $1\times10^7$, $2\times10^7$, $3\times10^7$, $4\times10^7$, $5\times10^7$, $1\times10^8$, $2\times10^8$, $3\times10^8$, $4\times10^8$, $5\times10^8$, $1\times10^9$, $2\times10^9$, $3\times10^9$, $4\times10^9$, or $5\times10^9$ transfected cells.

Therapeutic dose equivalents may vary depending on the exact type of therapeutic but in some cases may be a at least about $1\times10^7$, $2\times10^7$, $3\times10^7$, $4\times10^7$, $5\times10^7$, $1\times10^8$, $2\times10^8$, $3\times10^8$, $4\times10^8$, $5\times10^8$, $1\times10^9$, $2\times10^9$, $3\times10^9$, $4\times10^9$, or $5\times10^9$ total cells. Therapeutic doses may be about $1\times10^7$, $2\times10^7$, $3\times10^7$, $4\times10^7$, $5\times10^7$, $1\times10^8$, $2\times10^8$, $3\times10^8$, $4\times10^8$, $5\times10^8$, $1\times10^9$, $2\times10^9$, $3\times10^9$, $4\times10^9$, or $5\times10^9$ transfected cells.

In some cases, the methods described herein produce a population of cells that exhibit a decrease in relative population of effector or Temra cells when compared to a population of cells produced by a density gradient centrifugation method. In some cases, the population of cells exhibits at least about 5%, 10%, 15%, 25%, 30%, 40%, 50%, 75%, or 90% decrease in relative population of effector or Temra cells when compared to a population of cells produced by a density gradient centrifugation method. For example, it has been shown that DLD methods produce cell populations with roughly 40% fewer Temra cells than cells produced using ficoll or other methods, after treatment with a high integration lentivirus. See FIG. 21.

In some cases, the methods described herein produce a population of cells that exhibit a decrease in IL-1Ra expression when compared to a population of cells produced by a density gradient centrifugation method. In some cases, the population of cells exhibits at least about 5%, 10%, 15%, 25%, 30%, 40%, 50%, 60%, 75%, or 90% decrease in IL-1Ra expression when compared to a population of cells produced by a density gradient centrifugation method. In some cases, the decrease in IL-1Ra expression is apparent 0, 3, 6, 9, 13, or 16 days after being produced by the methods and systems described herein.

In some cases, the methods described herein produce a population of cells that exhibit a decrease in IL-6 expression when compared to a population of cells produced by a density gradient centrifugation method. In some cases, the population of cells exhibits at least about 5%, 10%, 15%, 25%, 30%, 40%, 50%, 60%, 75%, or 90% decrease in IL-6 expression when compared to a population of cells produced by a density gradient centrifugation method. In some cases, the decrease in IL-6 expression is apparent 0, 3, 6, 9, 13, or 16 days after being produced by the methods and systems described herein.

In some cases, the methods described herein produce a population of cells that exhibit a decrease in IL-13 expression when compared to a population of cells produced by a density gradient centrifugation method. In some cases, the population of cells exhibits at least about 5%, 10%, 15%, 25%, 30%, 40%, 50%, 60%, 75%, or 90% decrease in IL-13 expression when compared to a population of cells produced by a density gradient centrifugation method. In some cases, the decrease in IL-13 expression is apparent 0, 3, 6, 9, 13, or 16 days after being produced by the methods and systems described herein.

In some cases, the methods described herein produce a population of cells that exhibit a decrease in MCP-1 expression when compared to a population of cells produced by a density gradient centrifugation method. In some cases, the population of cells exhibits at least about a 5%, 10%, 15%, 20%, 25%, 30%, 40%, 50%, 60%, 75%, or 90% decrease in MCP-1 expression when compared to a population of cells produced by a density gradient centrifugation method. In some cases, the decrease in MCP-1 expression is apparent 0, 3, 6, 9, 13, or 16 days after being produced by the methods and systems described herein.

In some cases, the methods described herein produce a population of cells that exhibit a decrease in PD1 and Tim3 co-expression when compared to a population of cells produced by a density gradient centrifugation method. In some cases, the population of cells exhibits at least about a 5%, 10%, 15%, 20%, 25%, 30%, 40%, 50%, 60%, 75%, or 90% decrease in PD1 and Tim3 co-expression when compared to a population of cells produced by a density gradient centrifugation method. In some cases, the decrease in PD1 and Tim3 co-expression is apparent 0, 3, 6, 9, 13, or 16 days after being produced by the methods and systems described herein.

In some cases, the methods described herein produce a population of cells that exhibit a decrease in cell senescence or exhaustion when compared to a population of cells produced by a density gradient centrifugation method. In some cases, the population of cells exhibits at least about a 5%, 10%, 15%, 20%, 25%, 30%, 40%, 50%, 60%, 75%, or 90% decrease in cell senescence or exhaustion when compared to a population of cells produced by a density gradient centrifugation method. For example, it has been shown that DLD methods produce cells that show about 50% less PD1 and Tim3 co-expression compared to cells produced from ficoll, suggesting they have lower senescence and exhaustion than cells produced using ficoll. See FIG. 24.

In some cases, the methods described herein produce a population of cells that exhibit a decrease in propensity to trigger cytokine release syndrome when compared to a population of cells produced by a density gradient centrifugation method. In some cases, the population of cells exhibits at least about 5%, 10%, 15%, 20%, 25%, 30%, 40%, 50%, 60%, 75%, or 90% decrease in cell propensity to trigger cytokine release syndrome when compared to a population of cells produced by a density gradient centrifugation method.

In some cases, the methods described herein produce a population of cells that exhibit a decrease in time in culture required before being delivered to a patient when compared to a population of cells produced by a density gradient centrifugation method. In some cases, the population of cells require about 1, 2, 3, 4, 5, 6, 7, or 8 fewer days in culture required before being delivered to a patient when compared to a population of cells produced by a density gradient centrifugation method.

In some cases, the exhibited increase or decrease of one or more biological properties when compared to a population of cells produced by a density gradient centrifugation method is apparent 0, 3, 6, 9, 13, or 16 days after being produced by the methods and systems described herein.

In some cases, the methods described herein produce a population of cells that exhibit a decrease in time required to expand in culture to produce a single therapeutic dose equivalent of cells when compared to a population of cells produced by a density gradient centrifugation method.

In some cases, the methods described herein produce a population of cells that exhibit a decrease in time required to expand in culture to produce a single therapeutic dose equivalent of cells when compared to a population of cells produced by a density gradient centrifugation method.

User Interface

FIGS. 5A-5H illustrate a graphical user interface (GUI) that can be used in methods and systems described herein. The GUI can comprise a control panel and a visual representation of the processing system. The processing system may comprise a particle separation unit, a cassette to which one or more microfluidic cartridges are releasably coupled and supported, and a plurality of components configured to be a part of the particle separation unit, cassette, and/or microfluidic cartridges. The GUI can be configured to receive user input, for example, to enter preliminary data before a separating process begins, or to adjust the one or more of the plurality of components while a separating process is in progress. The GUI may comprise a variety of run protocols which a user can select from in order to achieve a desired target particle separation. The GUI may comprise a calibration protocol which allows the user to check or adjust the calibration of the mass sensors. For calibration adjustments, the GUI may prompt the user to sequentially place a plurality of calibration weights comprising distinct fixed mass values on each mass sensor. The sequence of weights may be from low mass to high mass, high mass to low mass, or may be randomized. There may be at least 3, 4, 5, 6, 7, 8, 9, or 10 calibration weight values in the sequence of weights. For each calibration weight, the user may be prompted to place a specific weight value on the mass sensor to be calibrated and to confirm that the weight is on the sensor. The user may be allowed to enter custom calibration weight value using an input device, for example to change the default calibration masses used to that of an available calibration weight.

For example, the user may be sequentially prompted to place a 100 g calibration weight on the mass sensor to be calibrated. The user may then confirm that the weight has been placed on the mass sensor, which prompts the system to store the 100 g calibration value and the GUI may then repeat the process by prompting the user to replace the 100 g calibration weight with a 200 g calibration weight followed by the other calibration weights of the sequence. If the user does not have a particular calibration weight, they may choose an option on the GUI to alter the calibration points using a custom calibration value corresponding to a different calibration weight with a similar mass to the missing weight. For example, if the user is missing a 400 g calibration weight required by the default calibration sequence, but has a 500 g calibration weight, they may enter a custom calibration value of 500 g into the GUI to proceed with the calibration. The processing system may validate the new calibration weight by ensuring that the new calibration falls within an expected drift range before allowing the user to replace the previous calibration. For example, a new calibration may fall outside of an expected drift range if the new calibration slope differs from a factory calibration slope by at least 5%, 10%, 15%, 20%, or 25%. If the processing system is unable to validate the new calibration due to the slope falling outside the expected drift range the user may be prompted to repeat the calibration procedure. After a series of at least 2, 3, 4, or 5 successive failed calibrations, a service warning may be displayed which prompts the user to seek repairs to the mass sensor.

Figure 5A:
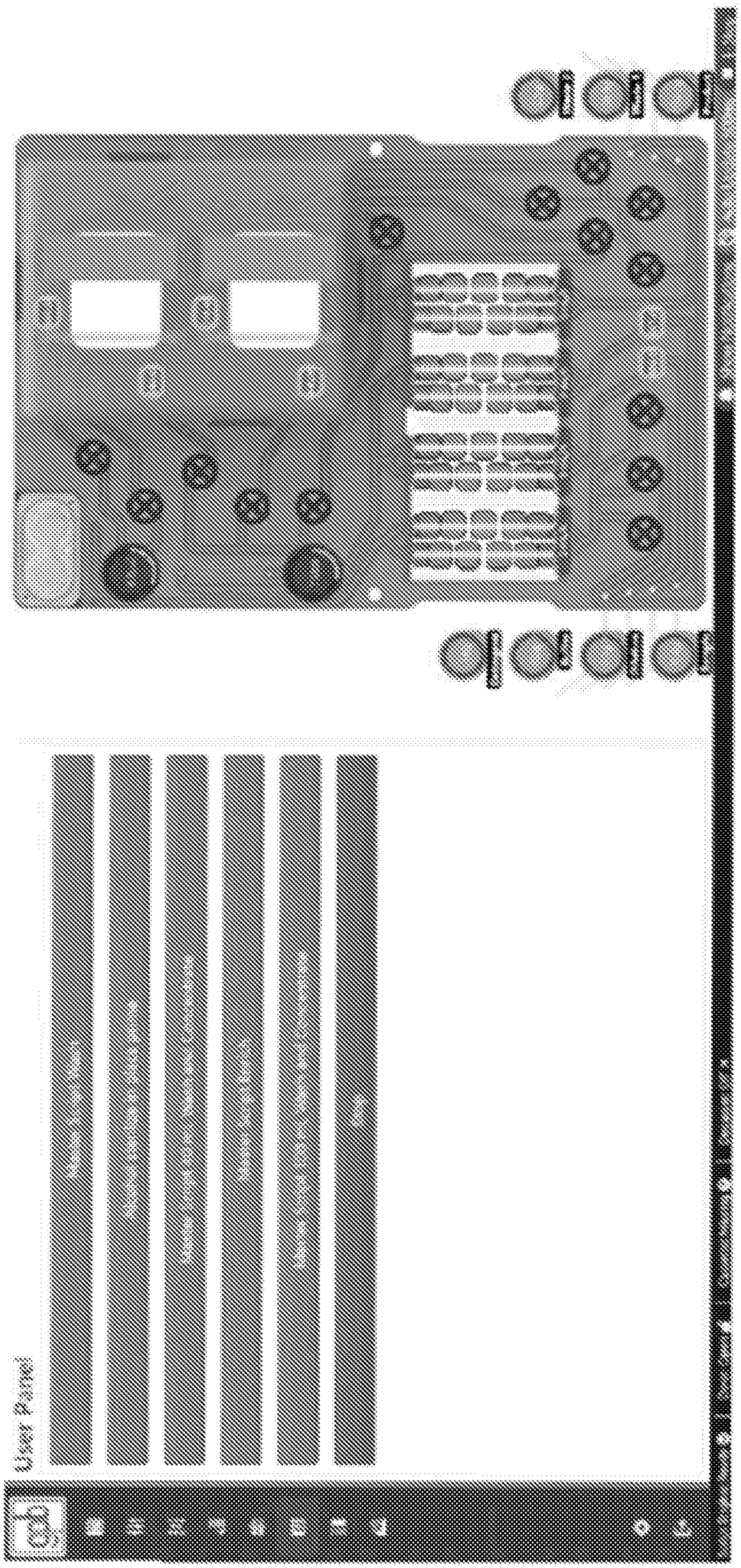
FIGS. 5A-5H illustrate a graphical user interface of a system in accordance with some embodiments.
Figure 5B:
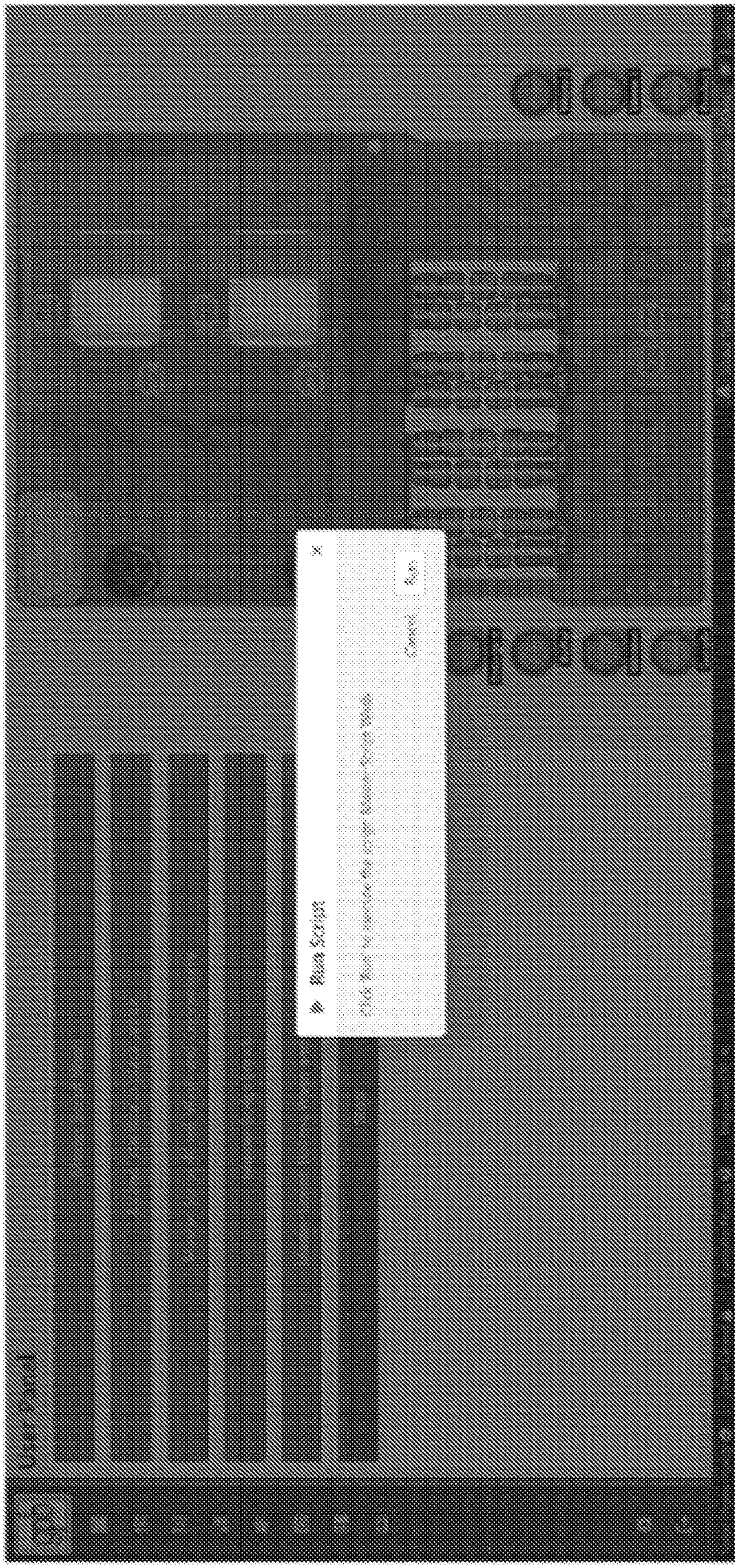
Figure 5C:
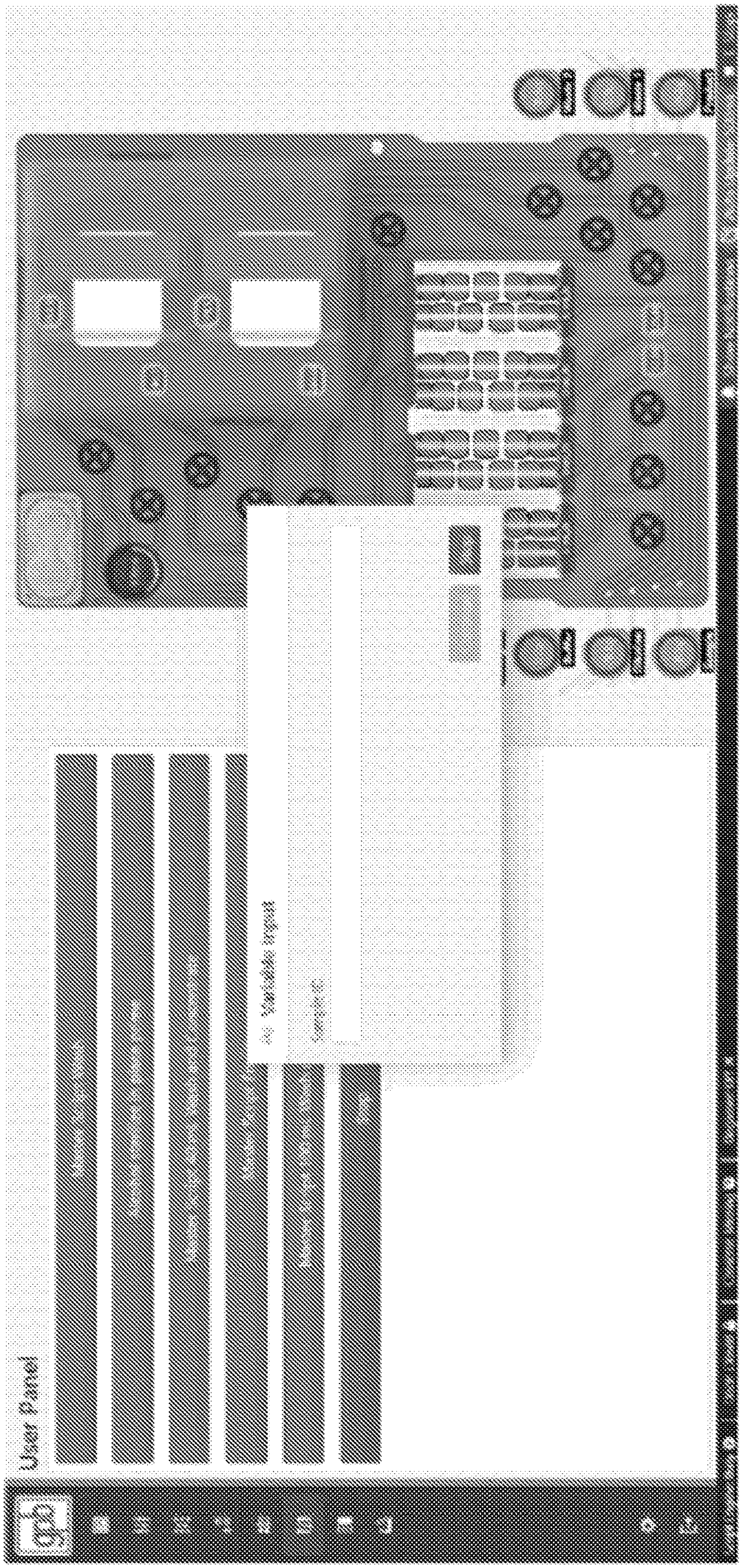
Figure 5D:
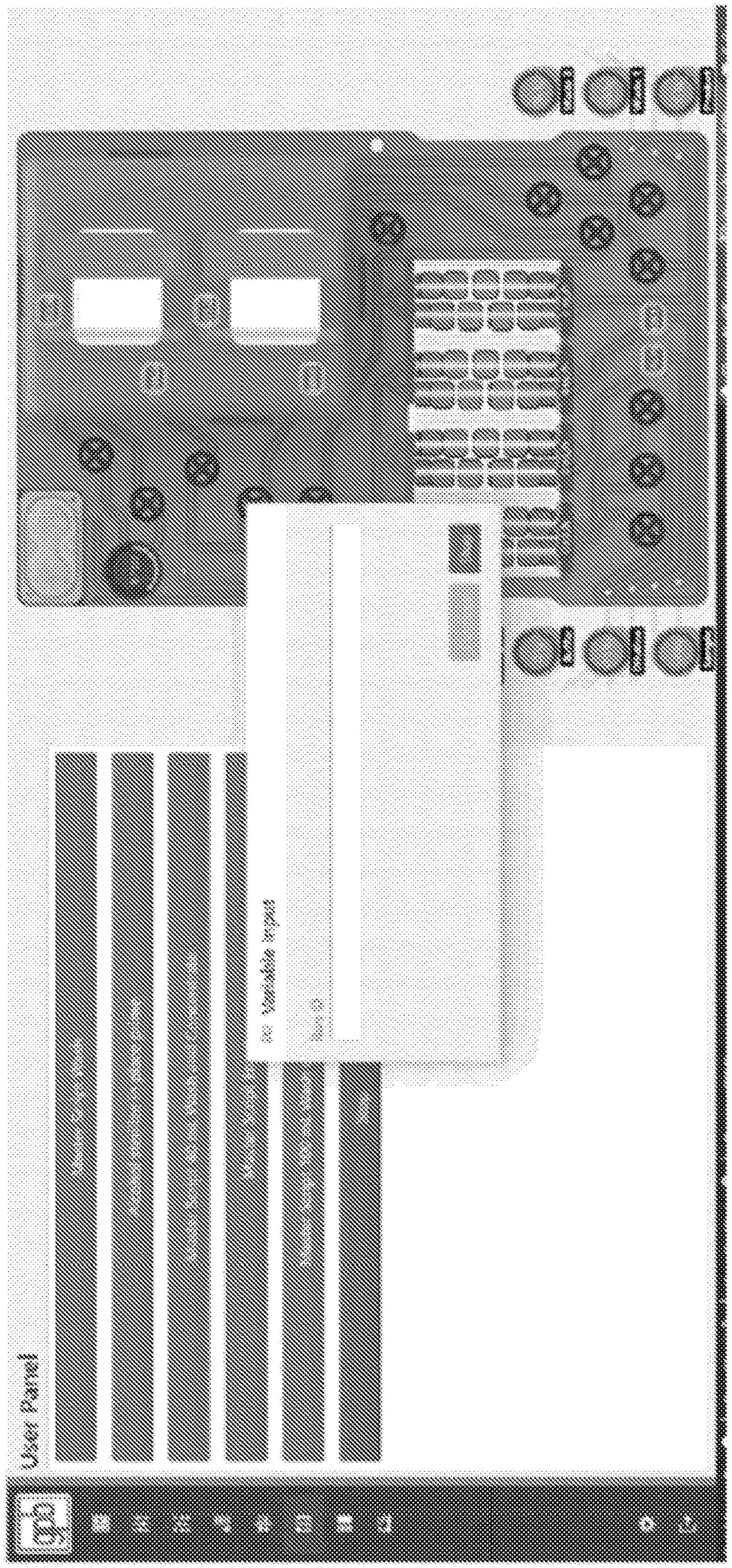
Figure 5E:
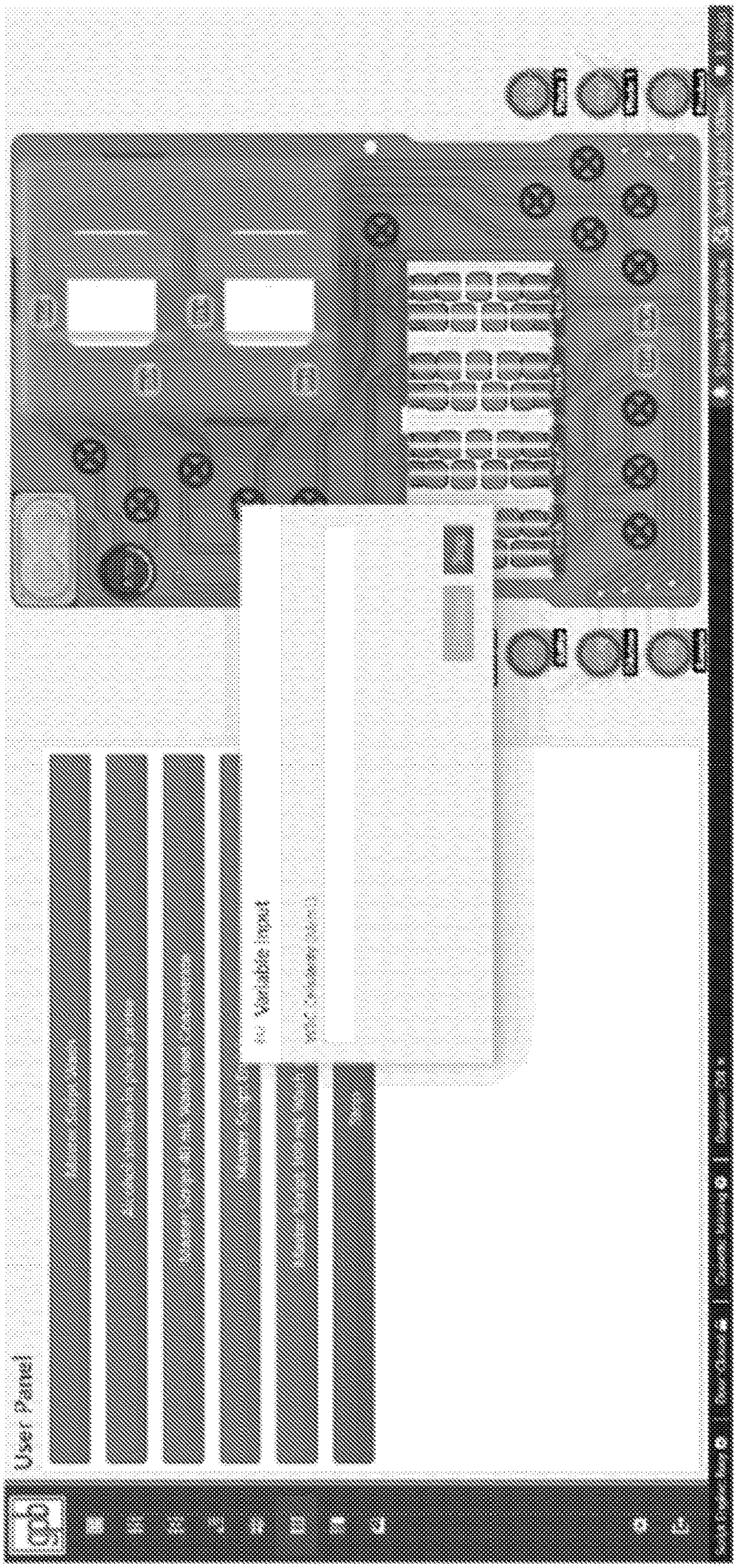
Figure 5F:
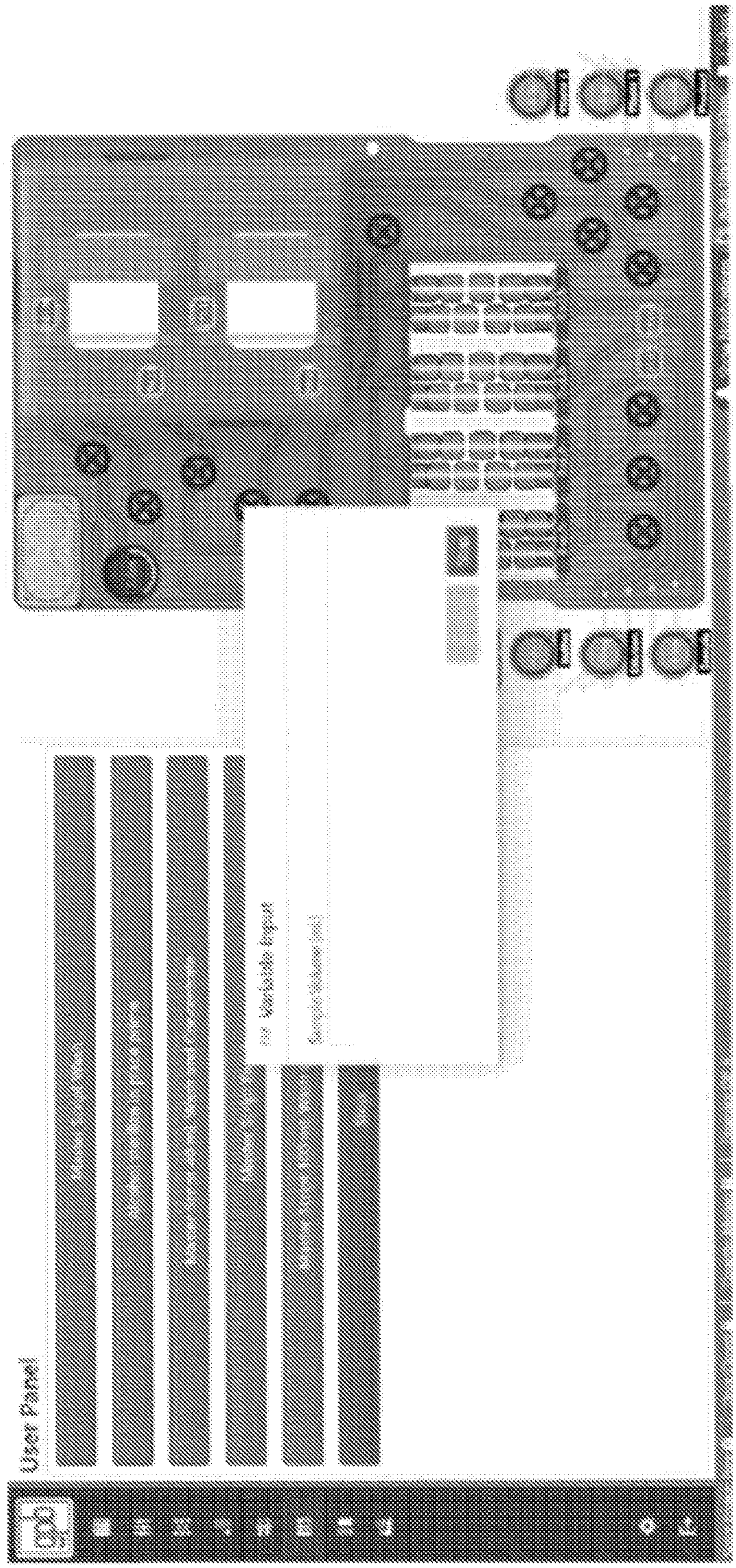

As illustrated in FIG. 5A, a control panel may be included on a left side of the GUI and the visual representation of the processing system may be included on a right side of the GUI. The control panel may include several options for a user to choose from, including scripted run options that a user can choose to achieve a desired target particle separation. The visual representation of the system can comprise visual depictions of each of the components in the processing system. For example, a visual representation can be provided for one or more of a degassing unit, bubble sensor, pressure sensor, pump, valve, pathway, flow sensor, and for each individual tubing entering into and exiting the cassette. Each of these components can be given its own color, helping a user to distinguish which visual representations correspond to which components. A user can click on each individual representation to see what a certain component is reading, or to manually adjust certain components. The system can display the readings from the components in real-time allowing a user to see the status of a separation process as it progresses. The user can view a status of and manually control an operation any of the components in real-time as a separation process is in progress.

The particle separation unit may also be configured to comprise a plurality of lights that can change colors depending on what mode the particle separation unit is in. For example, the lights may be white before a separation process has begun and can change to yellow to indicate that user input is required before a separation process can begin. The lights can also, for example, turn to red while a separation process is in progress, and change to green once the process has completed. The lights may also be turned on or off repeatedly or may be gradually dimmed or intensified to indicate the status to the user. For example, a blue light may slowly fade from dim to bright to indicate that a separation is proceeding normally, while a rapidly flashing red light may indicate that an error condition has occurred.

FIGS. 5B-5F illustrate a variety of notifications/commands that can pop up on the GUI to a user. The commands can include a request for information in relation to a variety of inputs that the system needs before a separation process can begin. For example, the system can ask a user to input a sample ID, a run ID, the cellularity of a sample (for example, in number of cells/mL), and a sample volume in an inlet sample bag. The notifications can be shown to a user to notify them of the status of the system during a separation process. For example, a notification can be shown to a user to notify them that the system is running in accordance with a run protocol that was selected before the separation process began. A notification can also be shown to a user to notify them that the system is experiencing one or more deviations from the run protocol selected by the user. The notification can indicate to a user where the one or more deviations are occurring in the system and can provide a user with one or more options to correct the deviations and bring the system back in line with the run protocol. Alternatively, the system can automatically make the necessary changes itself to bring the system back in line with the run protocol. For example, a pathway can be redirected to avoid entering the microfluidic devices if a bubble sensor has detected air bubbles in the fluid in the pathway. Additionally, the speed of one or more pumps can be increased or decreased depending on if the fluid in a pathway is detected to have high/low pressure, or if a higher/lower flow rate is desired to bring the system back in line with the run protocol. Also, a reading for a mass amount in each of the inlet or outlet solution bags can change as the mass sensors in each hanger detect the loss or gain of fluidic content. As such, a system can run completely autonomously throughout an entire separation process, or the system can also receive user input as a user sees fit.

In addition, or alternatively, to the notifications, the status of the separation process can also be visualized to the user by implementing graphical changes to the visual representation of the system. For example, a graphical change can include switching the color of a visual representation of a valve of the system to indicate to a user that the valve has switched from an "on" to an "off" position, or from "off" to an "on" position. The graphical change can also include changing a textual region next to a visual representation of a valve that changes from "on" to "off" or from "off" to "on" as a valve opens or closes. A graphical change can also comprise a textual region next to a visual representation of the one or more inlet streams, outlet streams, or pathways in the cassette to indicate a flow rate of fluid passing through. The textual region can change as the flow rate changes through these regions.

Figure 5G:
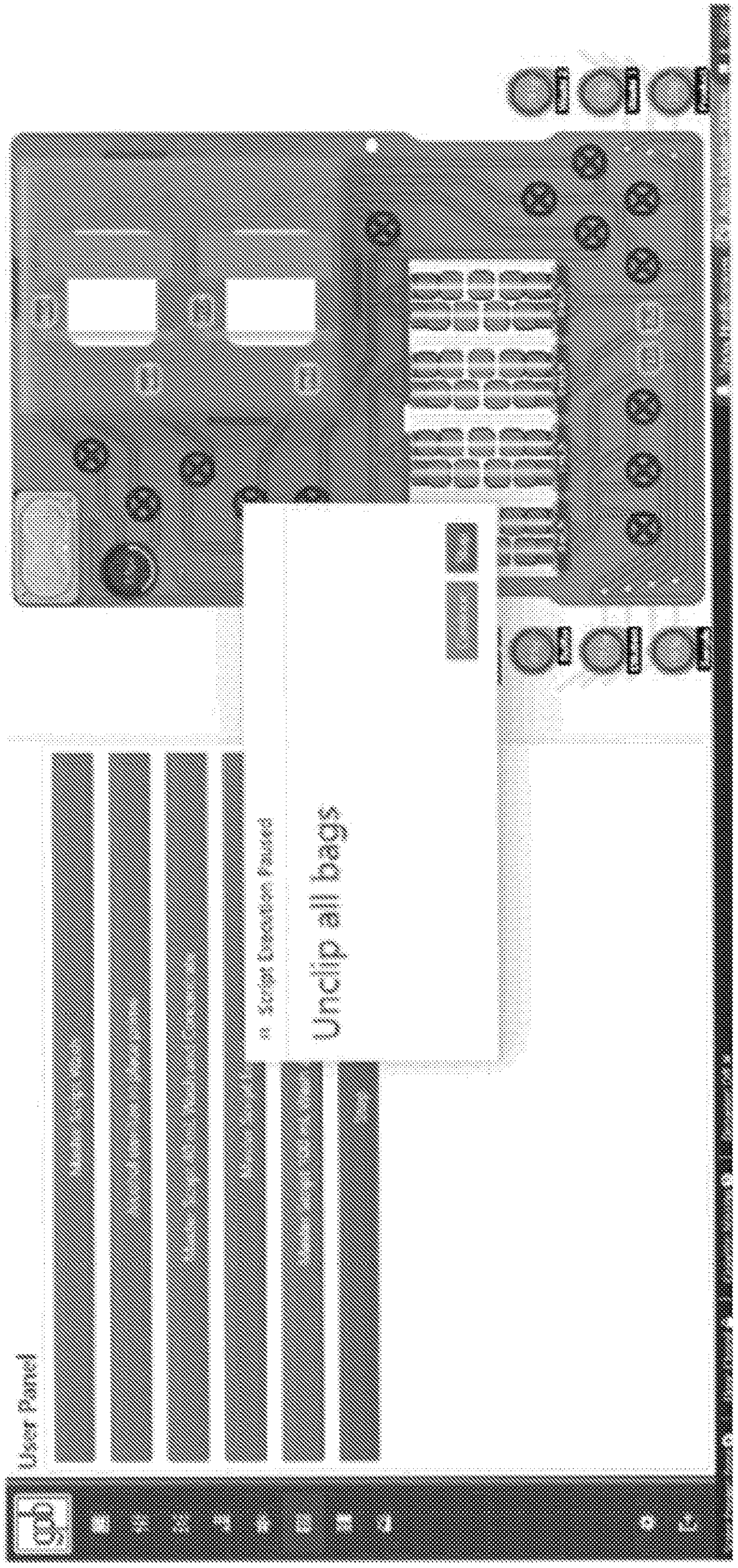
Figure 5H:
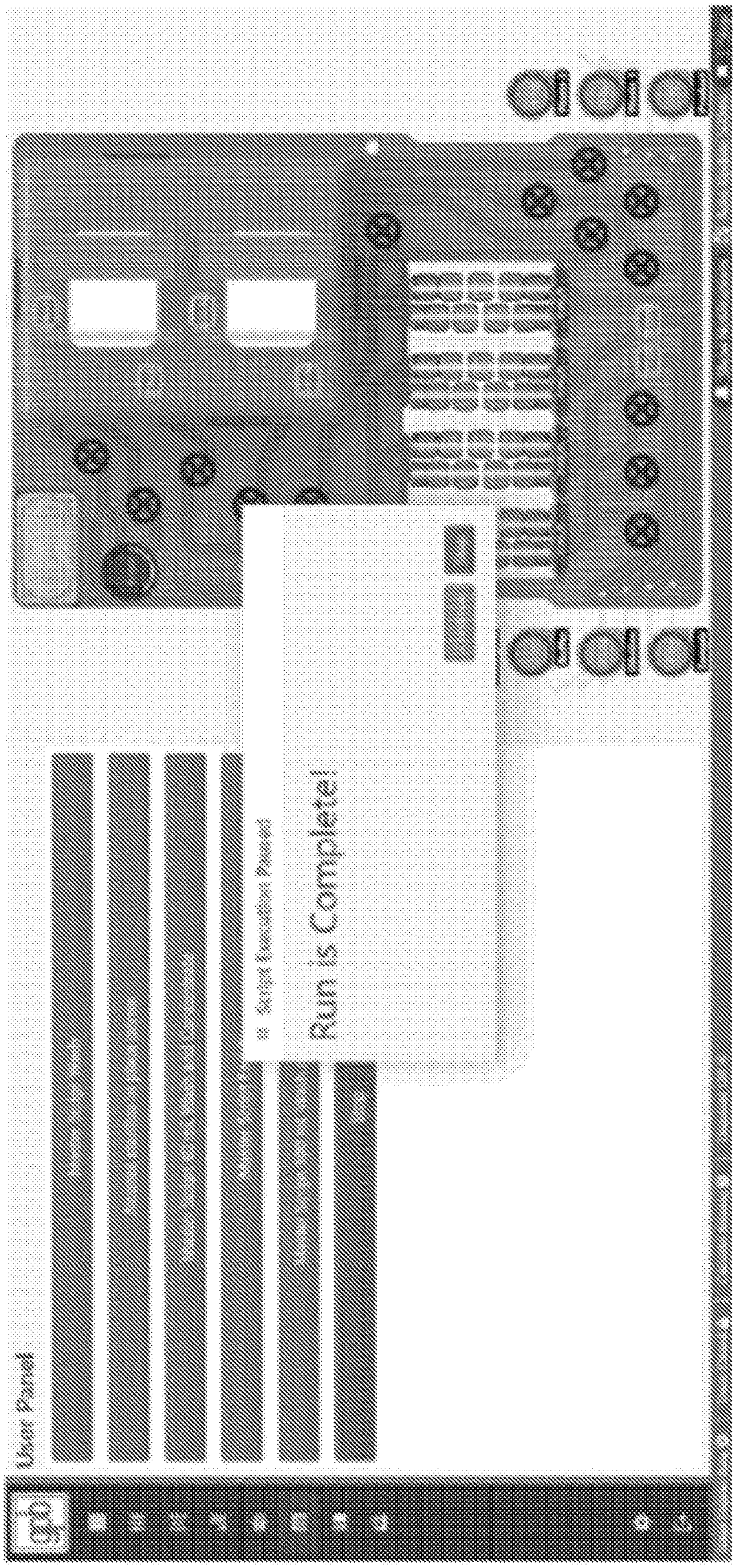

As illustrated in FIGS. 5G and 511, the system can also provide notifications for when a separation process has been completed. When a run is complete, the system can also generate a report that provides a user with a summary of the metrics of the components of the system during the separation process. An example of a system generated run report for a separation of leukocytes from red blood cells and platelets with a wash of the leukocytes into a new buffer media is seen in FIG. 51. In the example report, information is divided into system information, general information, results and estimates pertaining to the particular run, and performance metrics, which track sensor data as a function of time over the course of the run. The system and general information sections contain information about the run, the device (such as the serial number SN), the protocol used, the sample, the organization running the device, the device location, the user identity, timing information, the version of the software used and the run status (e.g. complete, aborted, or other specific error conditions).

The results and estimations section contains the input volume of the sample (in this case 130 mL), an estimate of the weight of the processed sample, the final product weight, and the actual run duration. In this case, the performance metrics section contains time course data readouts from pressure sensor 1, pressure sensor 2, the product bag scale (mass sensor) and the sample bag scale. For example, the performance metrics of the run report of FIG. 5I shows three color codes for the time course data displayed. The yellow trace (from 0 to 20 minutes on all graphs) shows the priming phase, when solutions are being loaded into the system, and the system is primed to clear any air bubbles. The red traces (from >20 minutes to approximately 53 minutes on all graphs) show the enrichment phase, when sample is being converted into enriched product by the DLD array, causing a corresponding increase in pressure on both pressure sensors. Also seen during the red trace is the increase in mass of the product bag over the course of the run and the depletion of mass in the sample as sample is converted to an enriched product. The slope of these graphs indicate the flow rate into the product bag and the flow rate out of the sample bag, respectively. The blue trace (from approximately 53 minutes to the end time point of all graphs) indicates the shut down phase, after the target product mass has been reached.

Figure 5J:
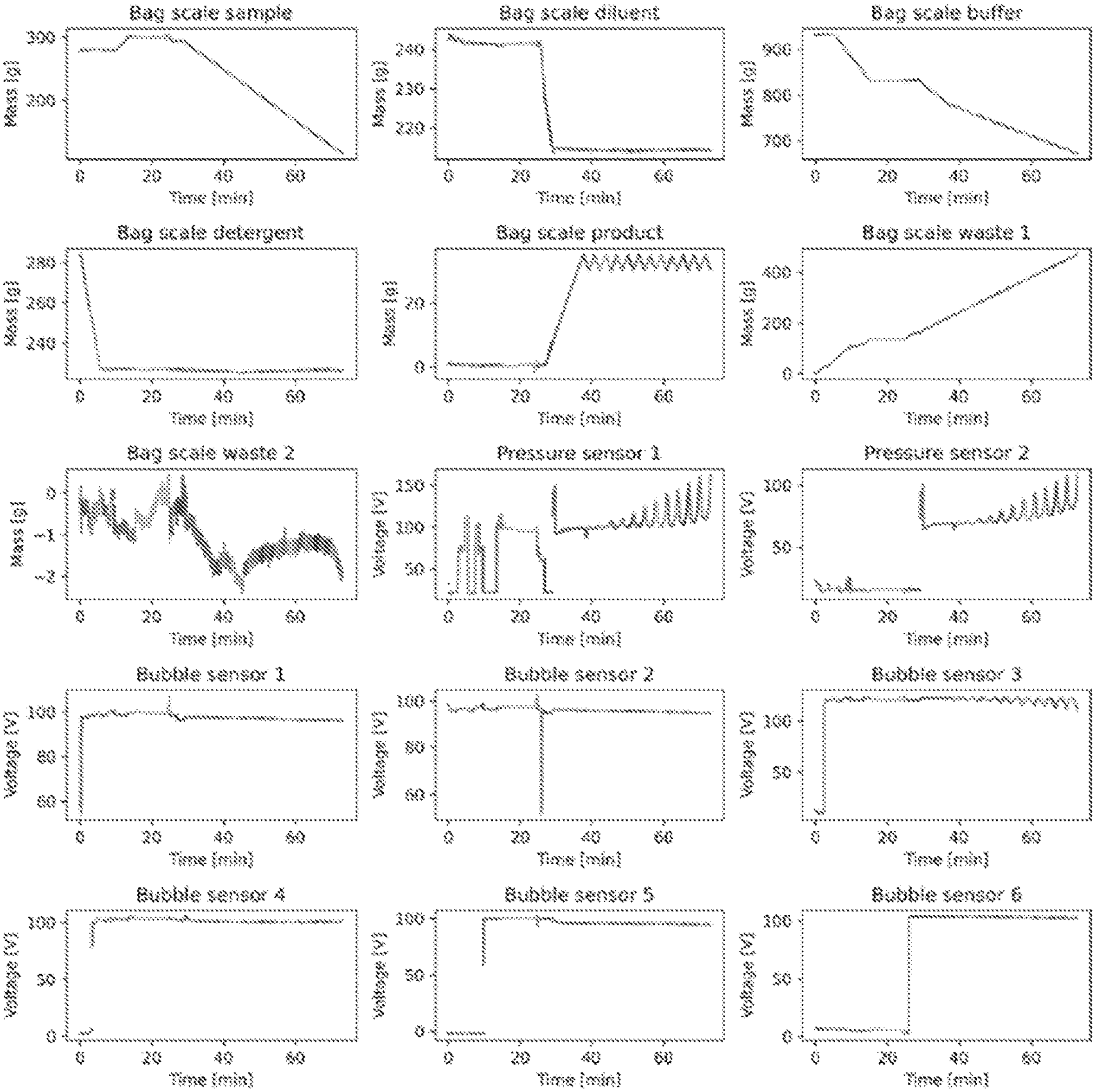

Other parameters that can be included in the performance metrics are the time course data series from the diluent bag scale, the buffer bag scale, the first and/or second waste bag scales, and/or any of bubble sensors 1-6 and combinations thereof. Example graphs of each of these parameters are shown in FIG. 5J. The example run in FIG. 5J shows an example of recirculation after a target product quantity has been obtained. The mass sensor data indicates the quantity of solution in each bag corresponding to the individual mass sensor, while the slope of these data indicates the mass flow rate into or out of the bags. The pressure sensor data is used to monitor the pressure experienced by target particles or cells as they travel from the sample bag to the product bag through the DLD. The pressure data is monitored and real time to make sure that pressure does not exceed a maximum pressure threshold that target cells or particles can tolerate without damage. The pressure data may also correspond to, or be used to estimate, the viscosity and/or cellularity of the product. This data summary can allow a user to examine a separation process and determine where changes can or should be made in order to achieve a different desired result. In some embodiments, the system can respond to the pressure data and adjust the separation in real-time or near real-time during the separation, for example by adjusting flow rates. The summary may be exported over a network connection or saved to a USB drive connected to a USB port on the system.

Figure 5K:
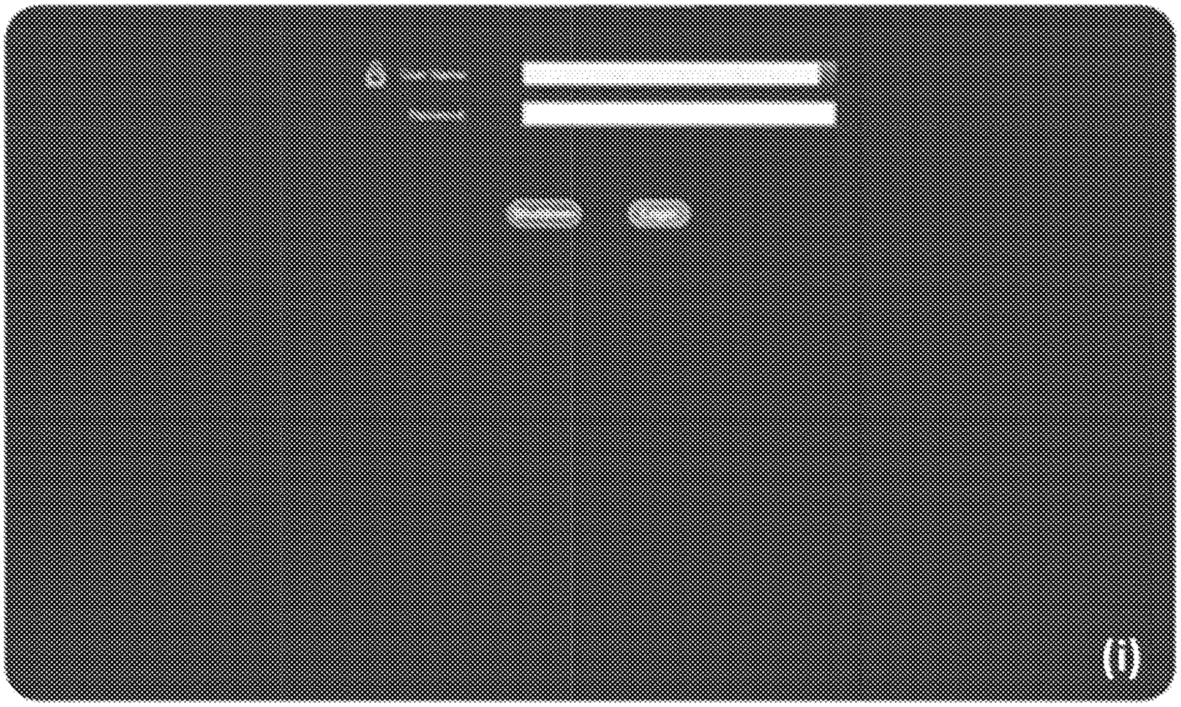
FIGS. 5K-5S illustrate an example interaction of a user with a graphical user interface of a system in accordance with some embodiments.
Figure 5K:
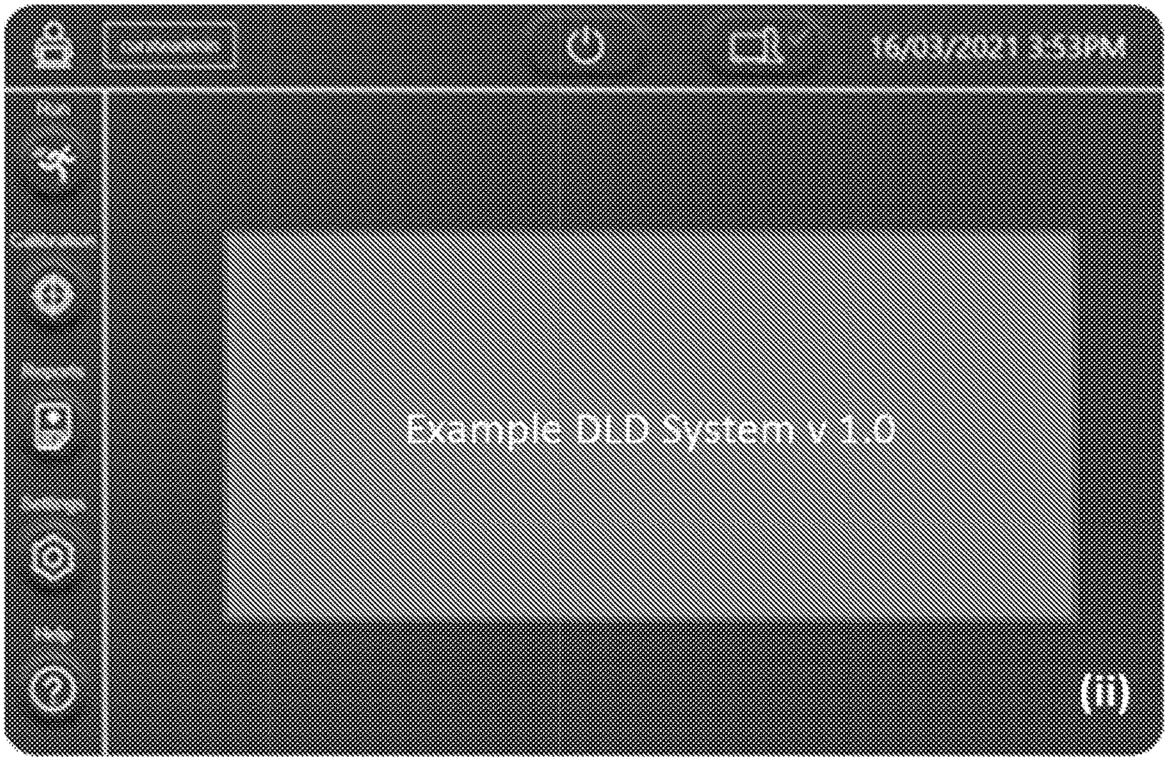
Figure 5L:
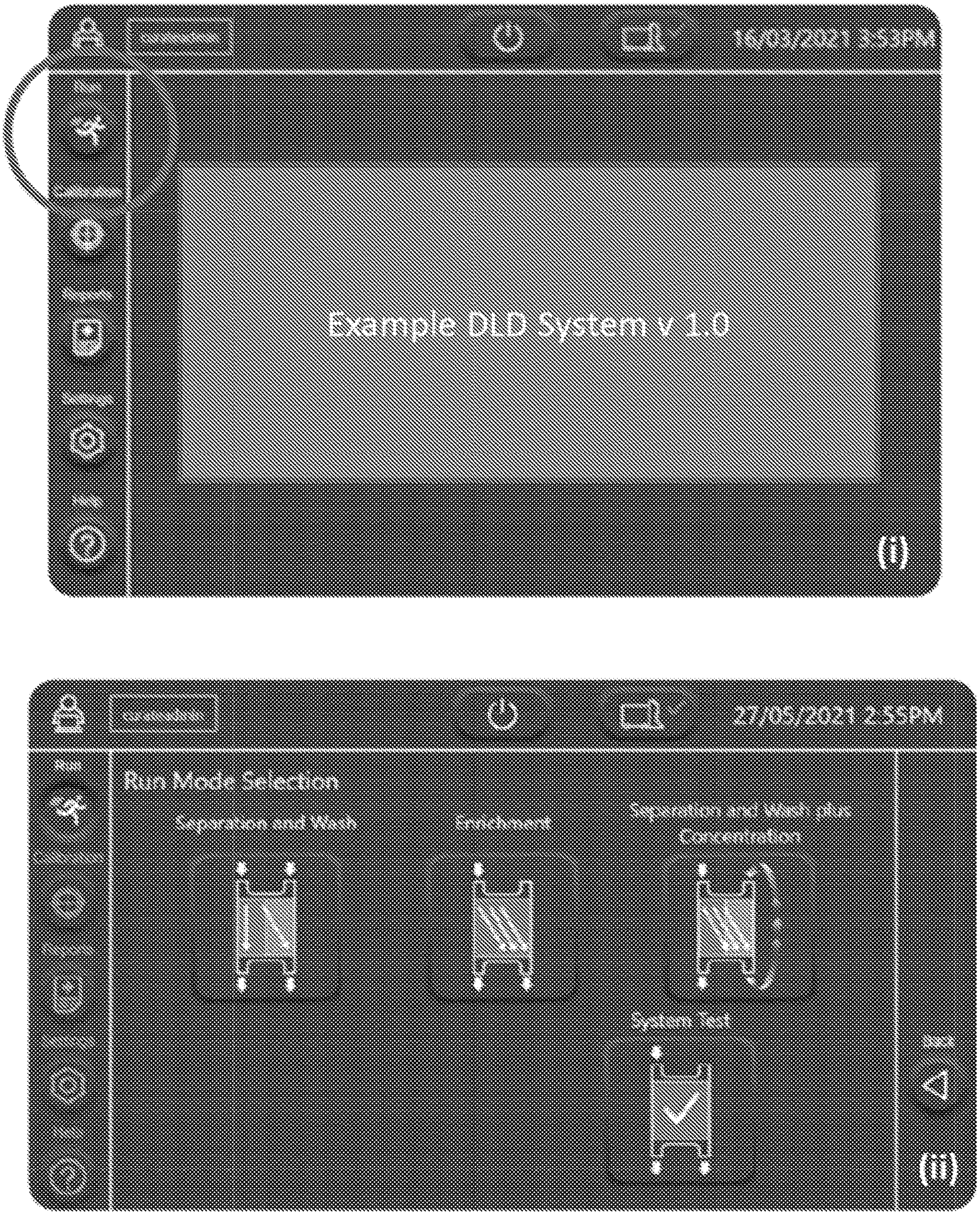
Figure 5M:
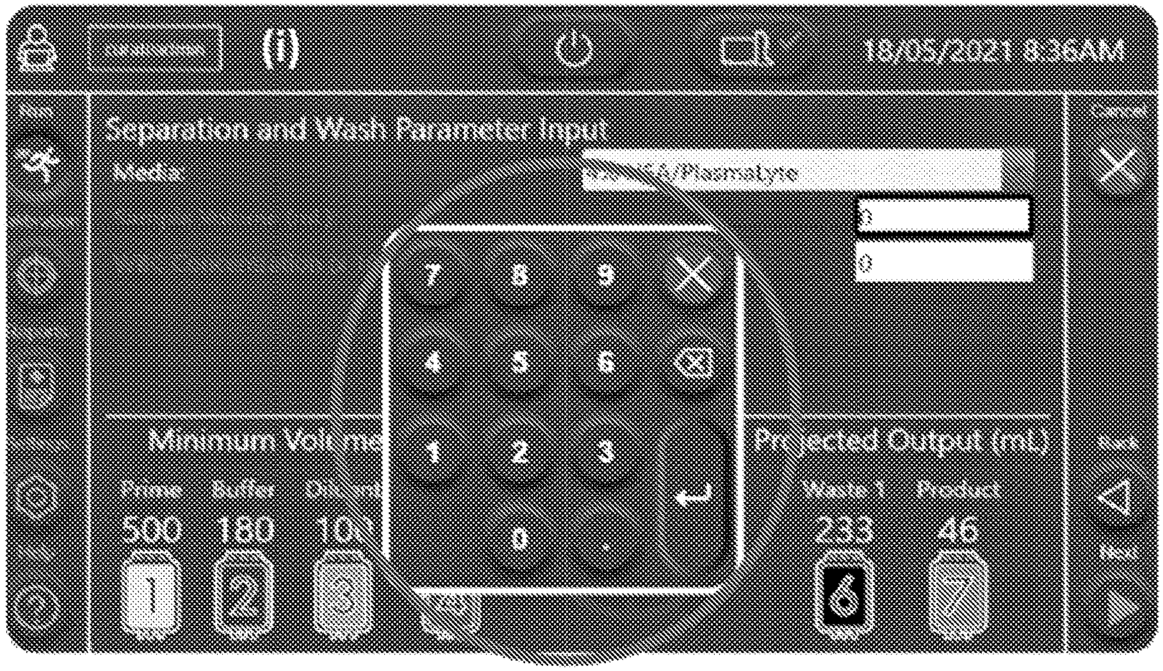
Figure 5M:
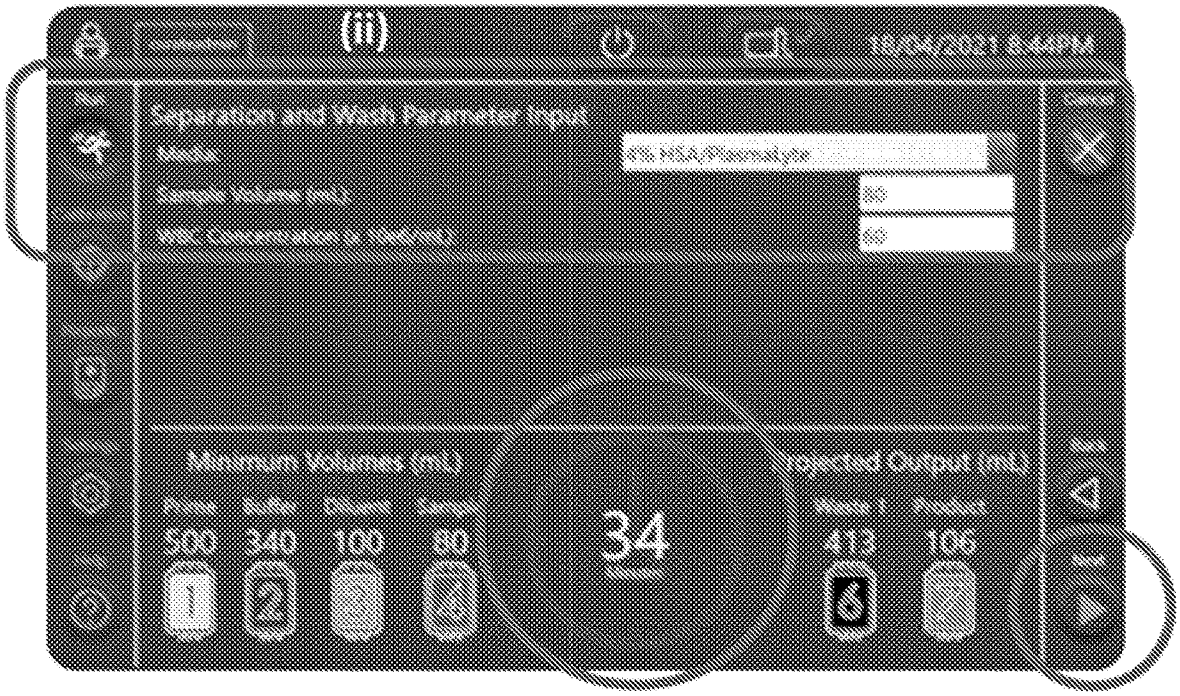
Figure 5N:
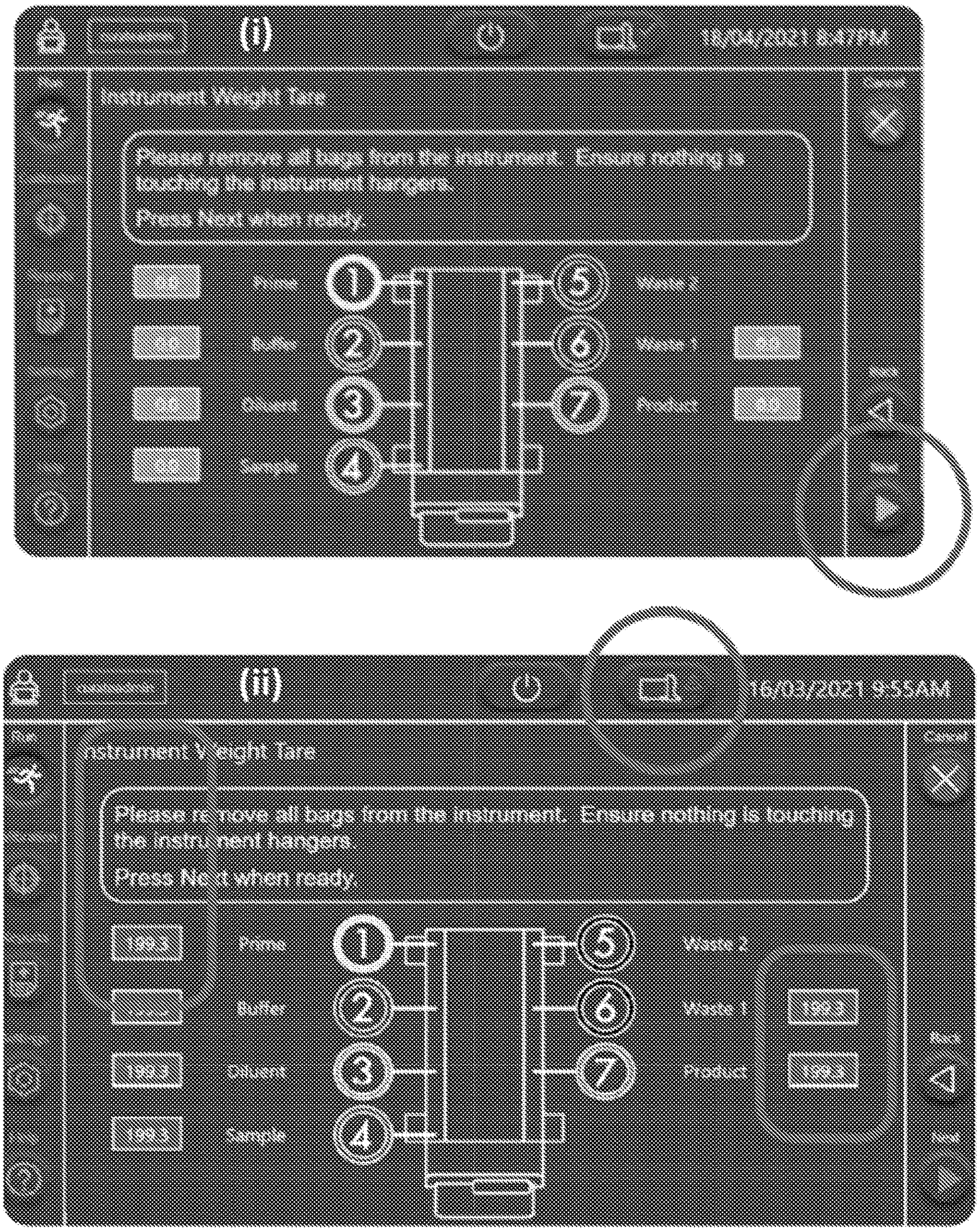

FIGS. 5K-5S illustrate an example embodiment of a user interaction with a GUI, according to some embodiments described herein. In FIG. 5K (i) a user is prompted by a primary touch screen display to enter their login credentials. Once the user is authenticated the primary touch screen display presents them with a default splash screen similar to the example shown in FIG. 5K (ii). If the user selects the run button as in FIG. 5L (i) they are presented with a plurality of run mode options from which they may select as show in FIG. 5L (ii). Once the user selects a mode, they may be prompted to enter a plurality of run parameter values using an onscreen keypad, as in the example of FIG. 5M (i), or another input device. Once all necessary run parameters are entered the user may proceed with the run. Before they proceed, the system may calculate necessary reagent quantities, projected outputs, and estimated run time which are displayed to the user as shown in FIG. 5M (ii). Once the user instructs the system to proceed with the run, the GUI may prompt the user to tare the mass sensors by removing all bags or weights from the mass sensors as shown in FIG. 5N (i).

Figure 5O:
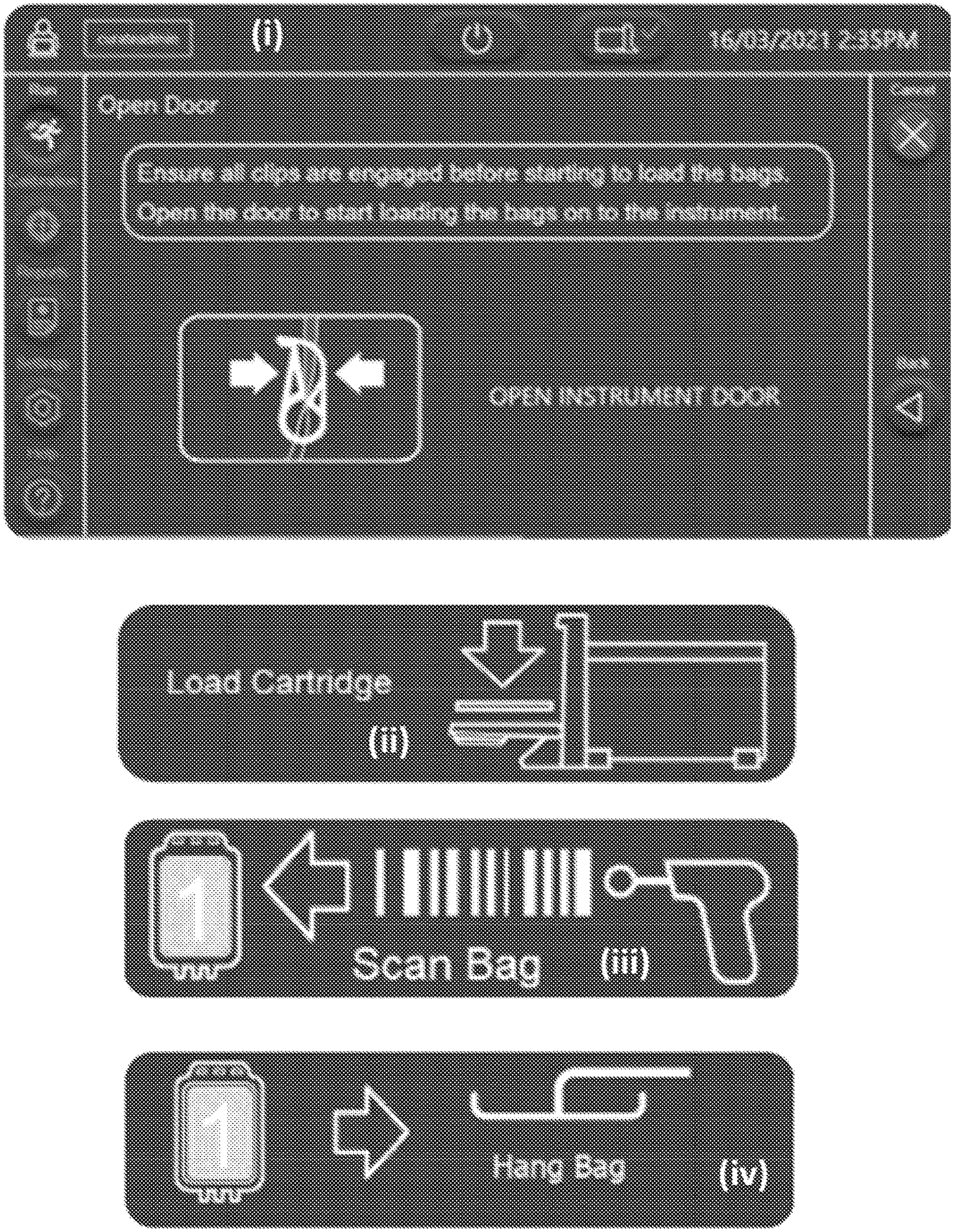

If, as in FIG. 5N (i), the mass sensors all read zero, the tare is validated and the user is allowed to proceed, whereas if the sensors are detecting nonzero masses, as in FIG. 5N (ii), an error message is displayed and the user is not allowed to proceed until the weights are removed from the mass sensors (in the event of a user error) or the sensors are serviced or recalibrated (in the case of a hardware or software error). Once the user is able to proceed, the GUI may provide instructions on loading the cassette, the sample, the reagents, the waste bags, and on priming the system. For example, the GUI may prompt the user to ensure all bag clips are closed, as in FIG. 5O (i). The GUI may then use a secondary status display to instruct the user to load the cartridge, as seen in FIG. 5O (ii), followed by prompting the user to scan a barcode of and load each color-coded bag onto the corresponding bag hanger, as shown for the yellow coded priming solution in FIG. 5O (ii-iv).

Figure 5P:
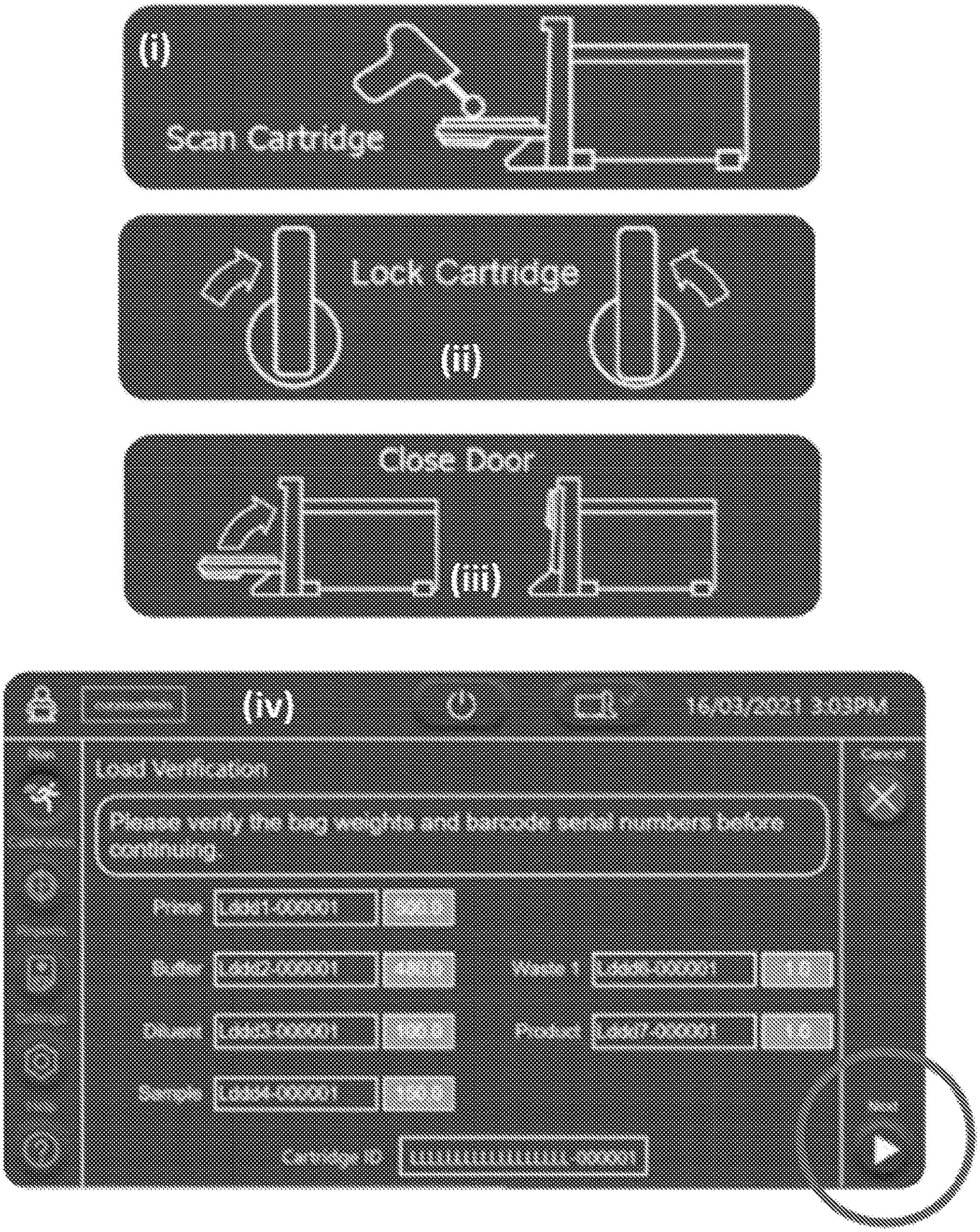
Figure 5Q:
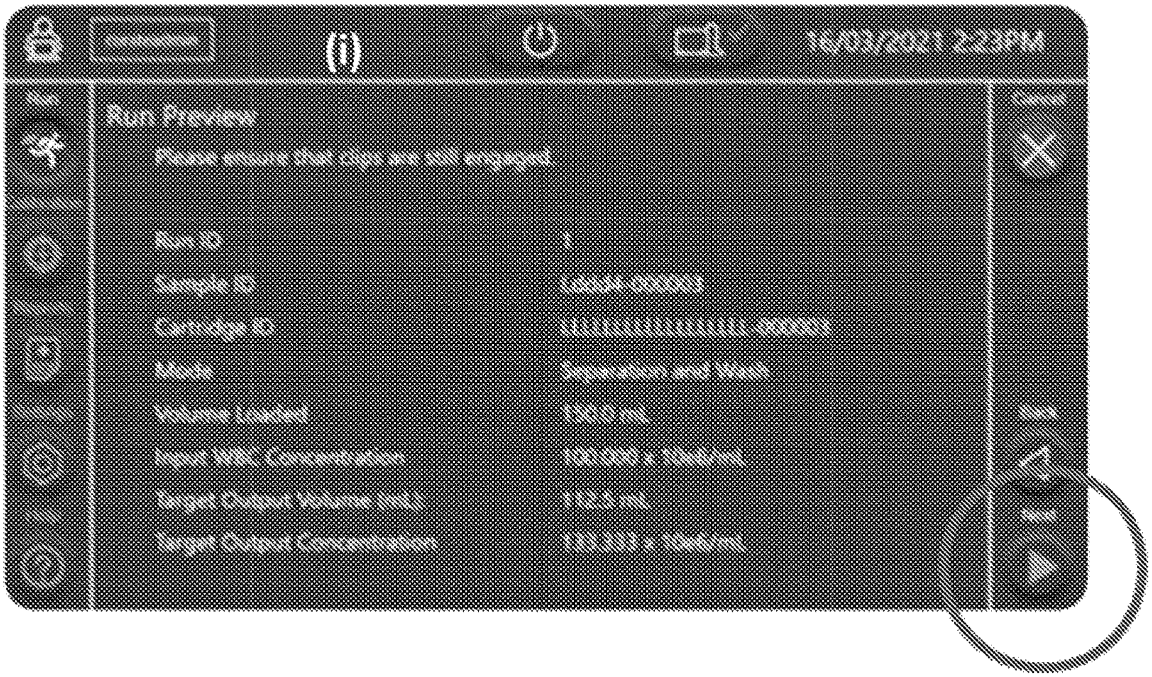
Figure 5Q:
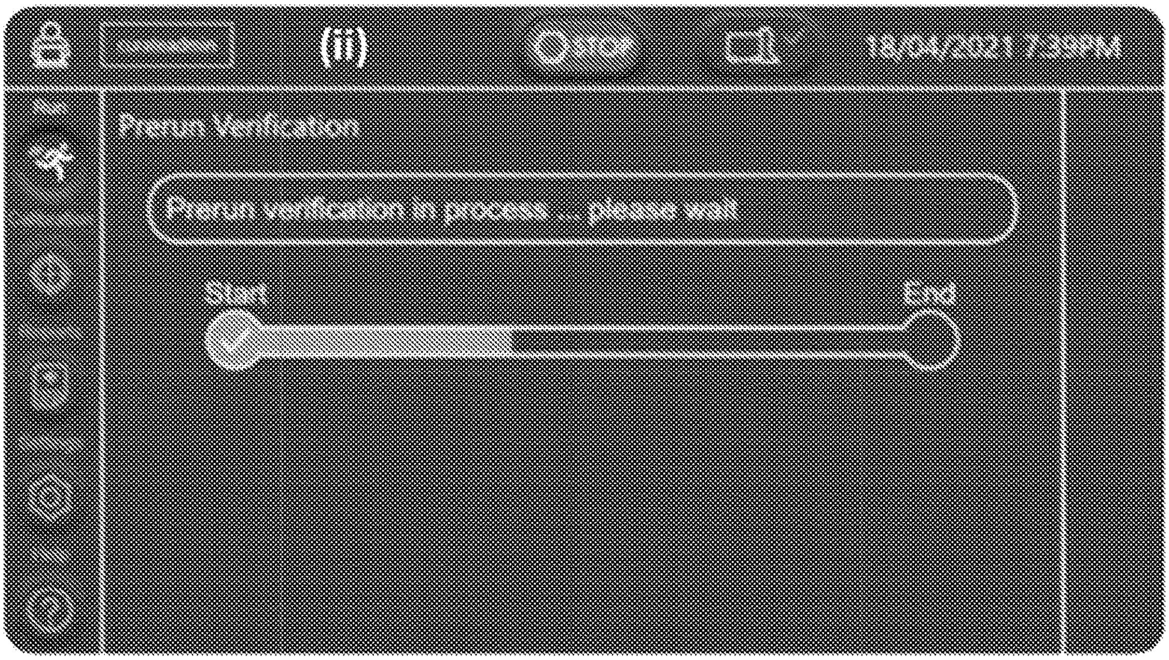
Figure 5R:
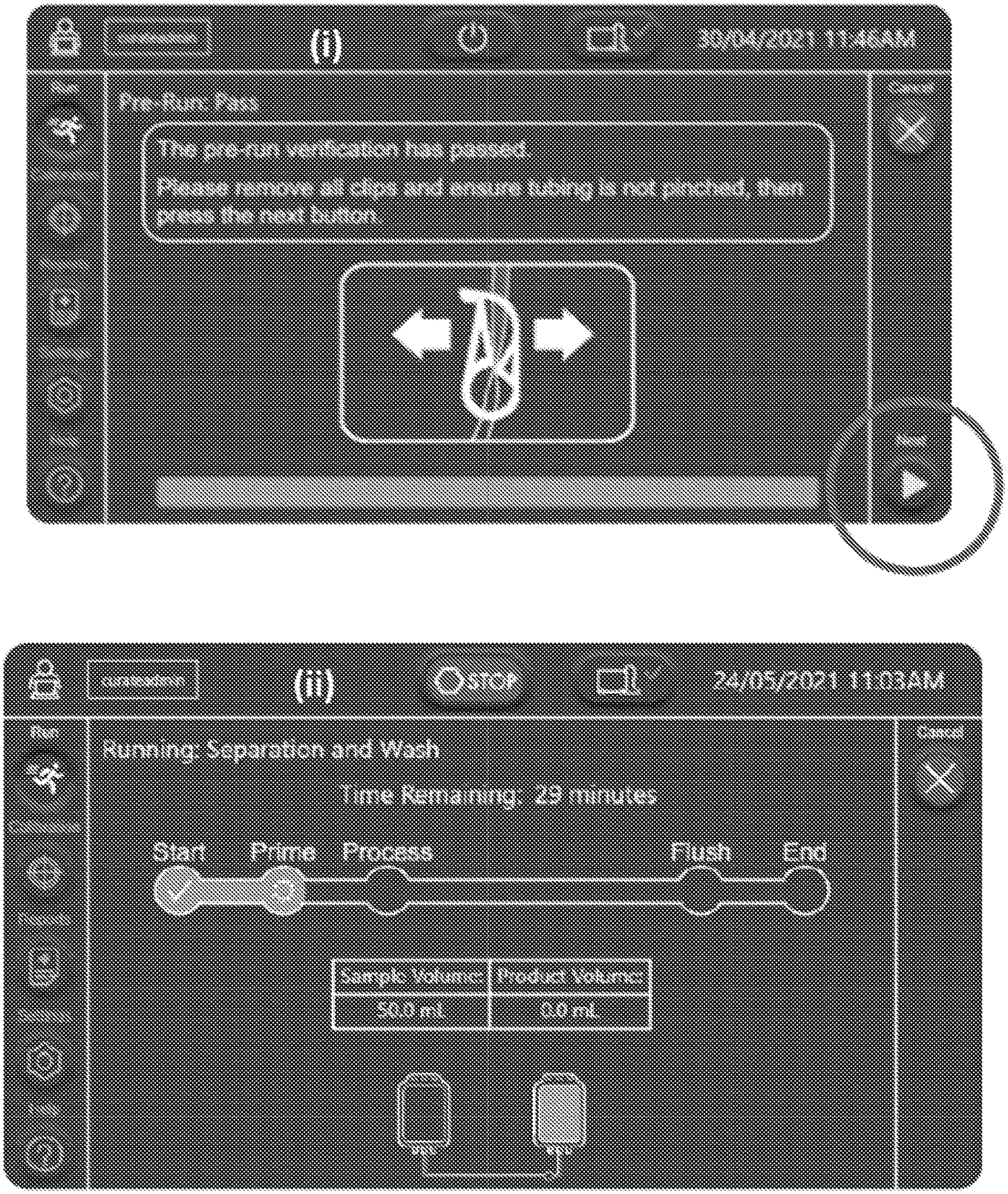
Figure 5S:
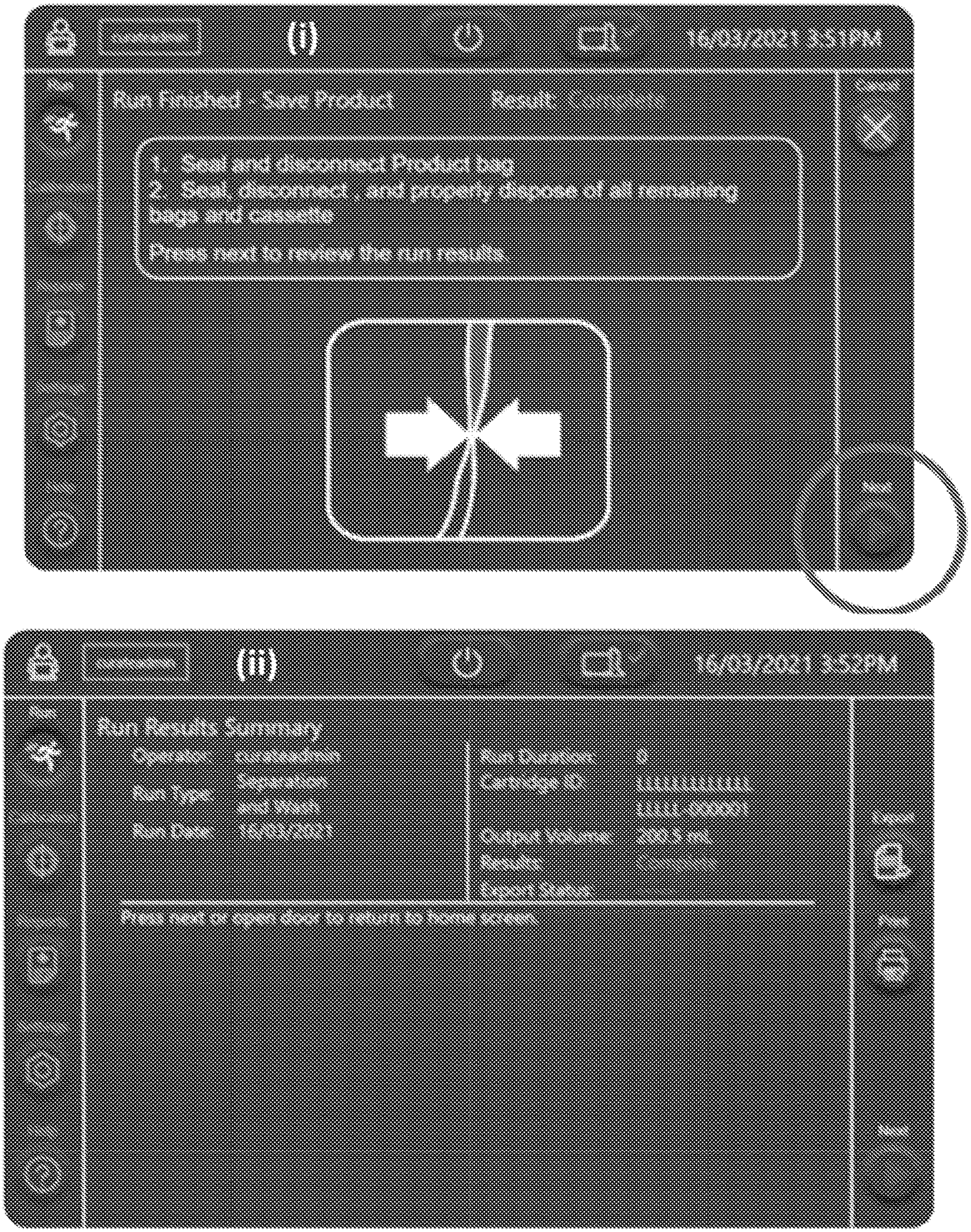

Once all necessary bags are loaded, the GUI may use the secondary status display to prompt the user to scan a barcode of the cartridge, to lock the cartridge in place, and close the instrument door as shown in FIG. 5P (i-iii). The GUI may then display to the user on the main screen, data encoded by each of the scanned barcodes which may comprise the serial numbers of each loaded bag and the serial number of the cartridge, and may further display the loaded masses of each bag, as demonstrated in the example in FIG. 5P (iv). The GUI may then display a preview of the run parameters, as in FIG. 5Q (i), giving the user a last chance to go back and reconfigure before starting a run procedure. When the user proceeds, the system may verify that sensors and other system components are operating properly and that the correct amount of necessary reagents were loaded. During this progress a progress bar for the prerun verification may be displayed by the GUI as demonstrated in FIG. 5Q (ii). When the verification has passed all system tests, the user may be instructed to remove all the bag clips as demonstrated in FIG. 5R (i), before they proceed to start the run. When the run is started, progress may be tracked on either or both of the main and secondary status displays. An example of a main screen status readout is shown in FIG. 5R (ii). Once the run has completed, the GUI may prompt the user to seal off the bag clips and retrieve the product bag as demonstrated in FIG. 5S (i). Once the user has done this, the GUI may prompt the user, as in FIG. 5S (ii), to either print or export a run report, for example a report as previously described herein.

Figure 6:
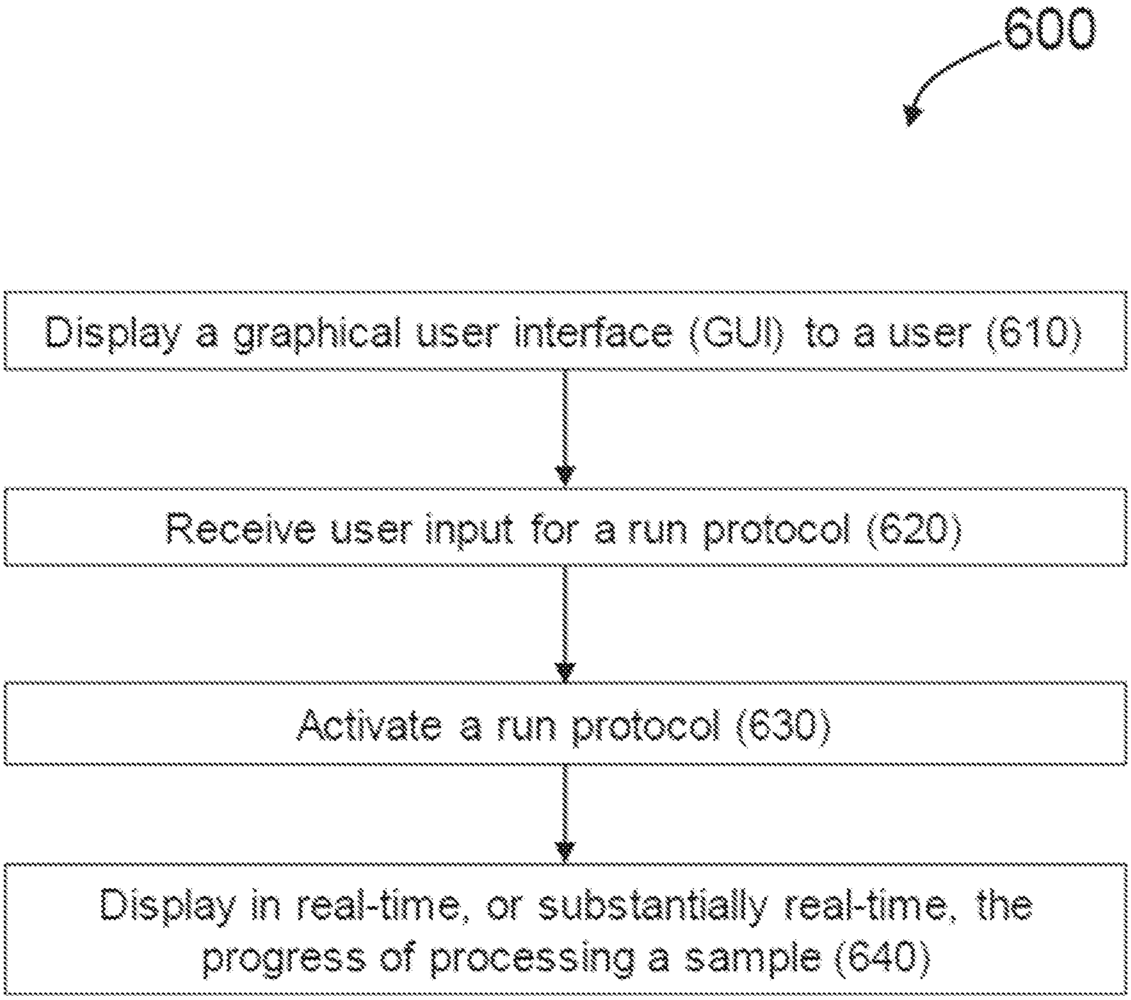
FIG. 6 illustrates a sample process that can be performed using a system in accordance with some embodiments.

FIG. 6 illustrates a process 600 that can be followed during a separation process. The process 600 may begin at step 610, wherein the system displays a GUI to a user. The GUI can comprise a control panel and a visual representation of the processing system. The processing system may comprise a particle separation unit, a cassette to which one or more microfluidic cartridges are releasably coupled and supported, and a plurality of components configured to be a part of the particle separation unit, cassette, and/or microfluidic cartridges.

Figure 3G:
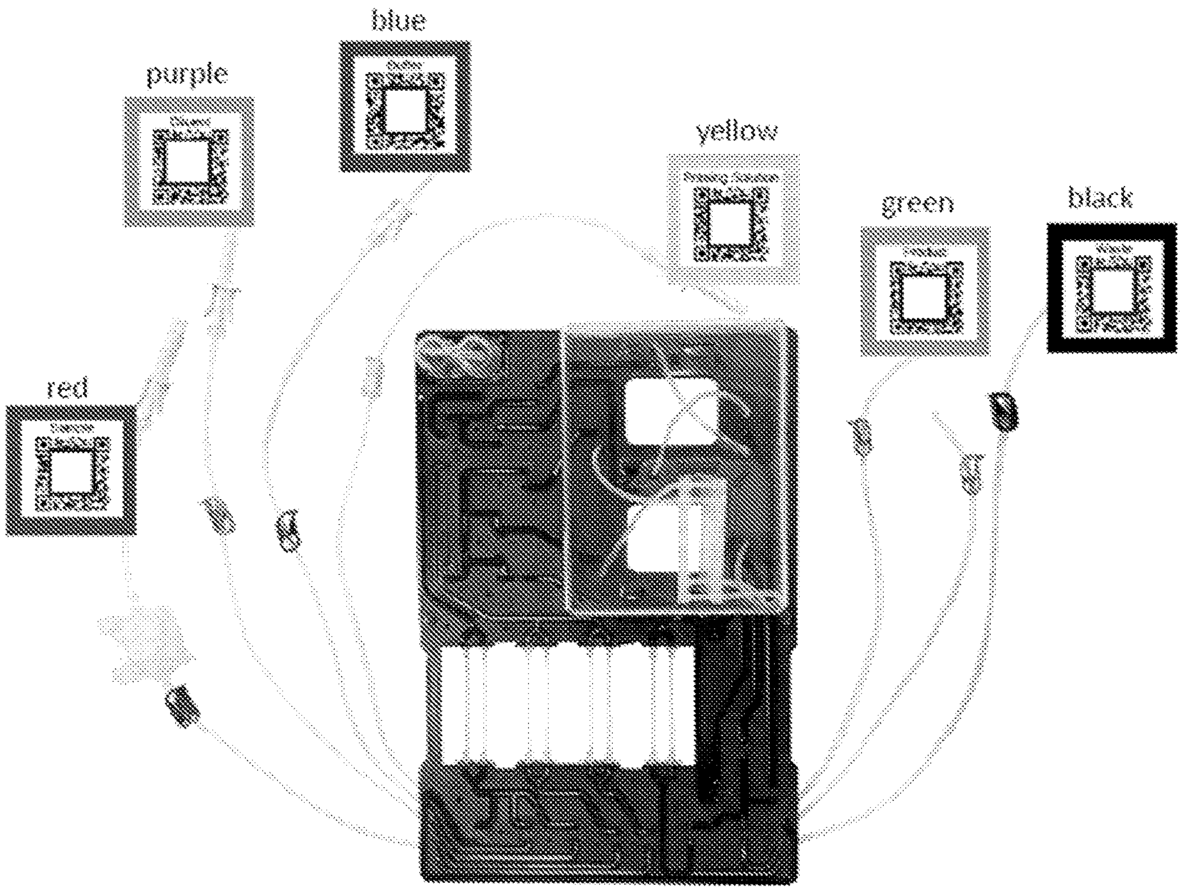
FIG. 3G illustrates an example of color coded connections of sample, diluent, buffer, priming solution, product, and waste bags to a cassette in accordance with some embodiments.

At step 620, the system may receive user input for a run protocol to be used in the separation process. The user input may be received through the GUI. The GUI may comprise a variety of run protocols which a user can select from in order to achieve a desired target particle separation. The GUI can also be configured to receive user input, for example, to enter preliminary data before a separating process begins, or to adjust the one or more of the plurality of components while a separating process is in progress. The GUI may calculate one or more predictions, based on the user input, of the volume of reagents needed to complete the separation, and of the volumes and concentrations of product and waste that will be produced by the run, and may further prompt the user to load at least the minimum predicted required volumes. The GUI may sequentially prompt the user to scan a barcode of a sample, reagent, or waste bag using a barcode scanner and to place the bag on a designated bag hook. The designated hook may be indicated to the user by a color code. For example, a red marking or light on a hook for the product bag may correspond to a red tag on the corresponding product bag. When a barcode on the red-tagged product bag is scanned, the GUI may prompt the user to load the product bag onto the red-marked bag hook (e.g. through a visual representation, by illuminating a red light on or near the bag hook, or other visible indication). Once the bag is loaded, the system may detect its presence as a weight on the mass sensor corresponding to the loaded bag hook. The user may be similarly prompted by the GUI to load a priming solution bag, which may be color coded yellow, a buffer bag, which may be color coded blue, and/or a waste bag which may be color coded in black. For each bag loaded, the system may verify that the correct weight was loaded onto the hooks before prompting the user to load the next bag. In some embodiments, the bags may be color coded and connected to the cassette as described in FIG. 3G, wherein the sample bag is coded red, the diluent bag is coded purple, the buffer bag is coded blue, the priming solution bag is coded yellow, the product bag is coded green, and the waste bag is coded black.

At step 630, the system can activate a run protocol 630. The run protocol can be based on the user input received at step 620.

At step 640, the system may display in real-time, or substantially in real time the progress of processing a sample. For example, a control panel may be included on a left side of the GUI and the visual representation of the processing system may be included on a right side of the GUI. The control panel may include several options for a user to choose from, including scripted run protocols that a user can choose to achieve a desired target particle separation. The visual representation of the system can comprise visual depictions of each of the components in the processing system. For example, a visual representation can be provided for one or more of a degassing unit, bubble sensors, pressure sensors, pumps, valves, pathways, flow sensors, and for each individual tubing entering into and exiting the cassette. Each of these components can be given its own color, helping a user to distinguish which visual representations correspond to which components. A user can click on each individual representation to see what a certain component is reading, or to manually adjust certain components. The system can display the readings from the components in real-time allowing a user to see the status of a separation process as it progresses. The user can manually adjust any of the components in real-time as a separation process is in progress.

Step 640 may also comprise displaying a variety of notifications/commands that can pop up on the GUI to a user. The commands can include a request for information in relation to a variety of inputs that the system needs before a separation process can begin. For example, the system can ask a user to input user authentication credentials, a sample ID, a run ID, the cellularity of a sample (for example, in number of cells/mL), and a sample volume in an inlet sample bag. The request for information for example, may be implemented as a series of prompts where a user is asked to scan a barcode of a sample bag, which inputs the sample ID, and run ID. The notifications can be shown to a user to notify them of the status of the system during a separation process. For example, a notification can be shown to a user to notify them that the system is running in accordance with a run protocol that was selected before the separation process began. A notification can also be shown to a user to notify them that the system is experiencing one or more deviations from the run protocol selected by the user. The notification can indicate to a user where the one or more deviations are occurring in the system and can provide a user with one or more options to correct the deviations and bring the system back in line with the run protocol. Alternatively, the system can automatically make the necessary changes itself to bring the system back in line with the run protocol. For example, a pathway can be redirected to avoid entering the microfluidic devices if a bubble sensor has detected air bubbles in the fluid in the pathway. Additionally, the speed of one or more pumps can be increased or decreased depending on if the fluid in a pathway is detected to have high/low pressure, or if a higher/lower flow rate is desired to bring the system back in line with the run protocol. As such, a system can run completely autonomously throughout an entire separation process, or the system can also receive user input as a user sees fit.

In addition, or alternatively, to the notifications, the status of the separation process can also be visualized to the user by implementing graphical changes at step 640 to the visual representation of the system. For example, a graphical change can include switching the color of a visual representation of a valve of the system to indicate to a user that the valve has switched from an on to an off position, or from off to an on position. The graphical change can also include changing a textual region next to a visual representation of a valve that changes from "on" to "off" or from "off" to "on" as a valve opens or closes. A graphical change can also comprise a textual region next to a visual representation of the one or more inlet streams, outlet streams, or pathways in the cassette to indicate a flow rate of fluid passing through. The textual region can change as the flow rate changes through these regions.

The system can additionally provide notifications at step 640 for when a separation process has been completed. When a run is complete, the system can also generate a report that provides a user with a summary of the metrics of the components of the system during the separation process. This data summary can allow a user to examine a separation process and determine where changes can or should be made in order to achieve a different desired result.

Digital Processing Device

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple° Mac OS X Server®, Oracle® Solaris, Windows Server°, and Novell° NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian OS, Apple iOS®, Research In Motion® BlackBerry OS®, Google® Android®, Microsoft® Windows Phone® OS, Microsoft® Windows Mobile® OS, Linux", and Palm® WebOS. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony PS3@, Sony® PS4@ Microsoft® Xbox 360@, Microsoft Xbox One, Nintendo® Wii®, Nintendo® Wii U, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein. In other embodiments, the digital processing device includes a plurality of displays to send visual information to a user. In some embodiments, the plurality of displays comprises a status display which sends visual status information to a user and a control display which sends visual control information to a user.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. For example, the input device can comprise a barcode scanner. In some embodiments, the input device may comprise a haptic feedback device. In further embodiments, the input device is a Kinect, Leap Motion, or the like. In still further embodiments, the input device is a combination of devices such as those disclosed herein.

Figure 7:
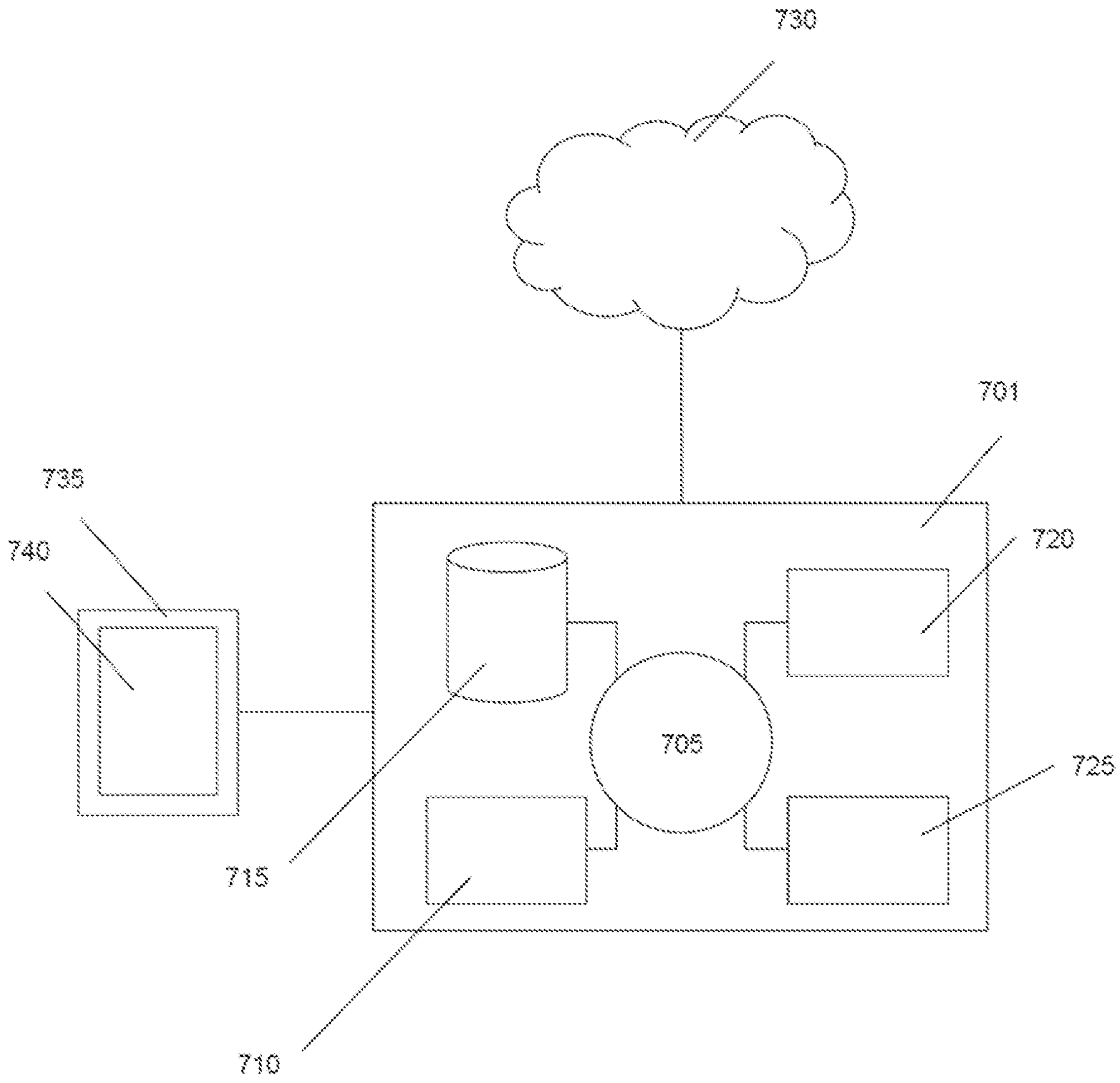
FIG. 7 illustrates an exemplary digital processing device programmed or otherwise configured to regulate various aspects of the target particle separation in accordance with some embodiments.

Referring to FIG. 7, in a particular embodiment, an exemplary digital processing device 701 is programmed or otherwise configured to operate a particle separation system. The device 701 can regulate various aspects of the target particle separation of the present disclosure, such as, for example, performing processing steps. In this embodiment, the digital processing device 701 includes a central processing unit (CPU, also "processor" and "computer processor" herein) 705, which can be a single core or multi core processor, or a plurality of processors for parallel processing. The digital processing device 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The digital processing device 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the device 701, can implement a peer-to-peer network, which may enable devices coupled to the device 701 to behave as a client or a server.

Continuing to refer to FIG. 7, the CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and write back. The CPU 705 can be part of a circuit, such as an integrated circuit. One or more other components of the device 701 can be included in the circuit. In some cases, the circuit is an application specific integrated circuit (ASIC) or a field programmable gate array (FPGA).

Continuing to refer to FIG. 7, the storage unit 715 can store files, such as drivers, libraries and saved programs. The storage unit 715 can store user data, e.g., user preferences and user programs. The digital processing device 701 in some cases can include one or more additional data storage units that are external, such as located on a remote server that is in communication through an intranet or the Internet.

Continuing to refer to FIG. 7, the digital processing device 701 can communicate with one or more remote computer systems through the network 730. For instance, the device 701 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple iPhone, Android-enabled device, Blackberry®), or personal digital assistants.

Methods as described herein can be implemented by way of machine (e.g., computer processor) executable code stored on an electronic storage location of the digital processing device 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight. In some embodiments, a web application is written to some extent in a server-side coding language such as Active Server Pages (ASP), ColdFusion®, Perl, Java™, JavaServer Pages (JSP), Hypertext Preprocessor (PUP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C-Hk, C4, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple' App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PUP, Python™, and VB NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft" Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm° WebOS° Browser, Mozilla° Firefox° for mobile, Microsoft® Internet Explorer° Mobile, Amazon Kindle Basic Web, Nokia Browser, Opera Software® Opera Mobile, and Sony PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML, databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

Figure 13:
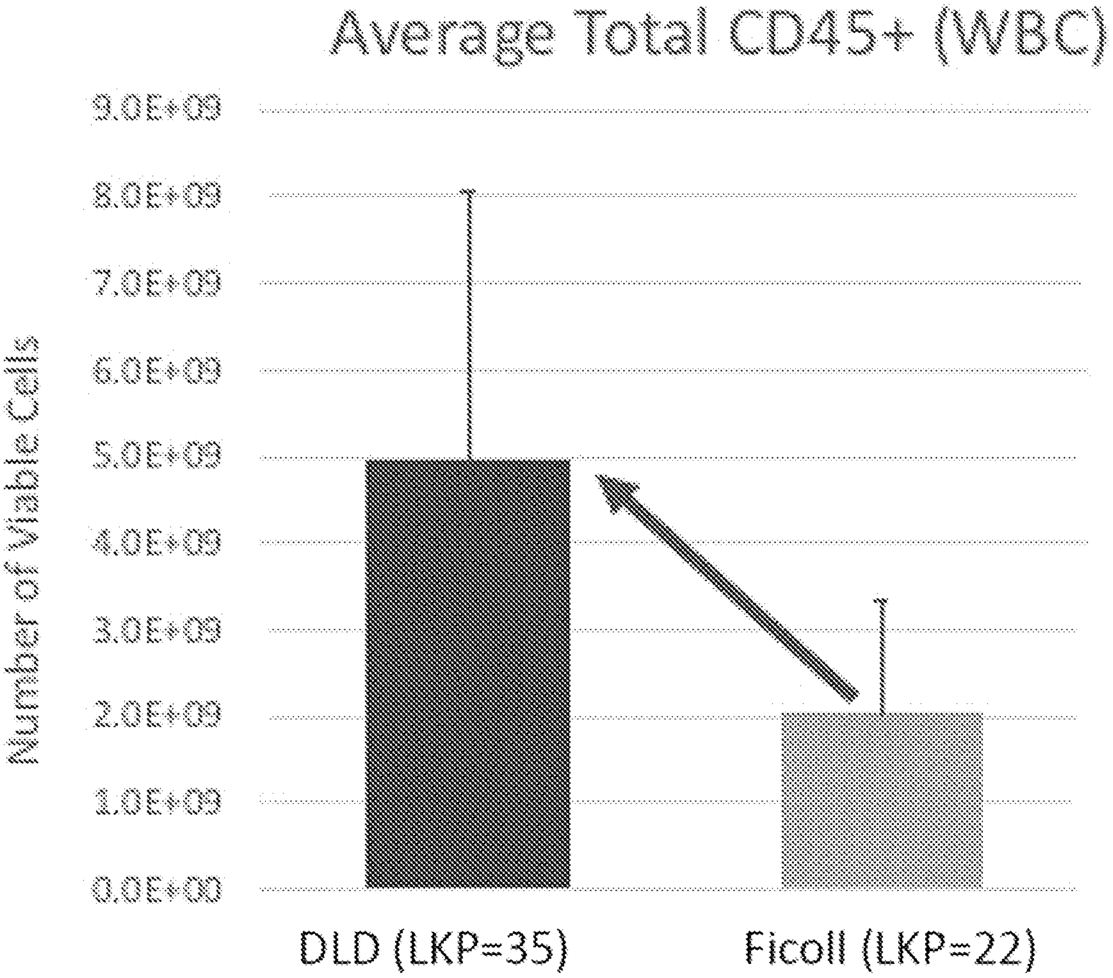
FIG. 13 illustrates improved recovery of all white blood cells (WBC)/CD 45+ cells from leukopaks enriched according to the systems and methods herein compared to Ficoll.
Figure 15:
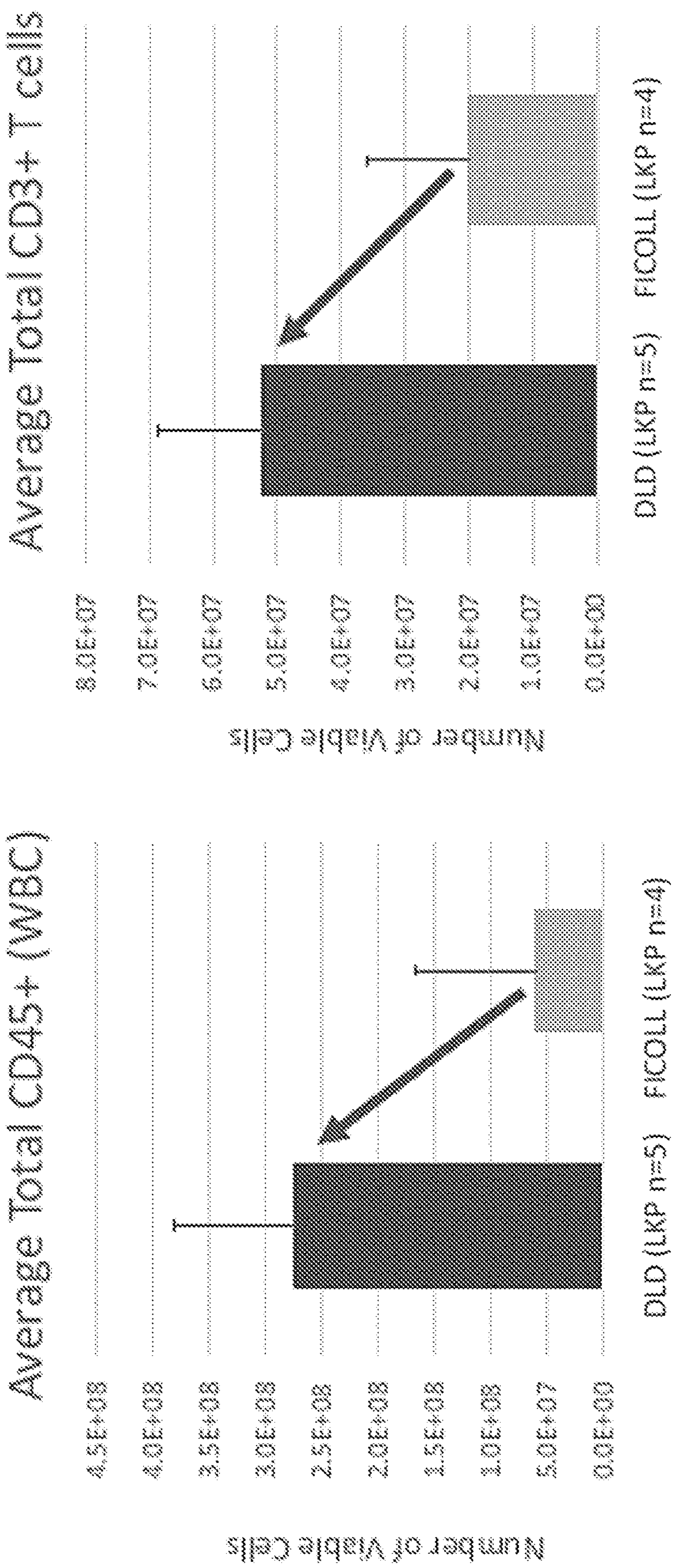
FIG. 15 illustrates improved recovery of all white blood cells (WBC)/CD 45+ cells and CD 3+ T cells from lower WBC count patient leukopaks enriched according to the systems and methods herein compared to Ficoll.
Figure 16:
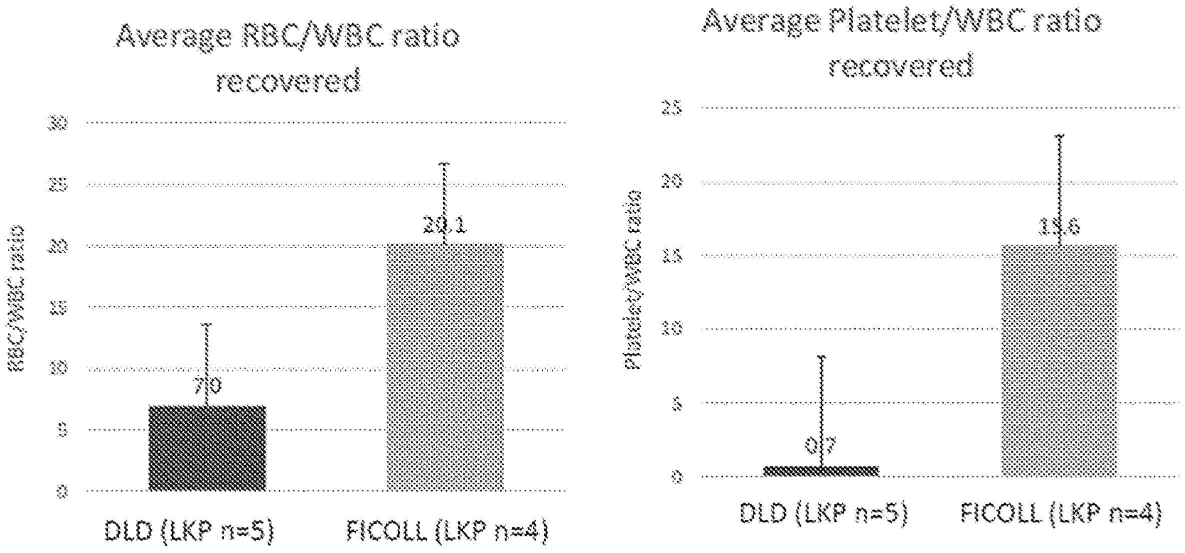
FIG. 16 illustrates that cells enriched according to the systems and methods herein from cancer patient leukopaks have fewer platelets and red blood cells compared to Ficoll.

Example 1-Greater Numbers of CD45+ Cells and CD3+ Cells are Recovered on Day 0 after DLD Isolation Compared to Density Gradient Separation The performance of the DLD system compared to density gradient centrifugation separation (e.g., Ficoll®, GE Healthcare) with respect to total numbers of leukocytes and T cells was investigated. Compared to Ficoll, leukopaks enriched using the DLD system showed an increased amount of total viable (DARQ7−) CD 45+ cells (a pan leukocyte marker), as determined by flow cytometry. As illustrated in FIG. 13 when normalized to 1 200 mL input, an average of $5\times10^9$ CD45+ cells would be isolated from leukocytes compared to $2\times10^9$ for cells isolated using Ficoll, a 2.5-fold increase. As illustrated in FIG. 15, there is also an increase in viable total CD45+ and CD3+ cells (a pan-T cell marker) obtained using the DLD system compared to ficoll when processing lower WBC count patient samples. This advantage is critical for obtaining lymphocytes from NHL, lymphoma, AML, breast cancer, colorectal cancer, or other cancer patients. Likewise, the increased lymphocyte and T cell recovery achievements of DLD can be expressed in terms of WBC ratios to cells that are desired to be depleted from input samples as a measure of debulking efficiency. As illustrated in FIG. 16, DLD products result in lower ratios of both RBC/WBC and PLT/WBC. The determination was done by flow cytometry using CD41 as a marker for platelets, CD235a for red blood cells and CD45 for white blood cells. The DLD protocol results in a white blood cell population with significantly less RBC's (red blood cells) and PLT's (platelets).

Figure 14:
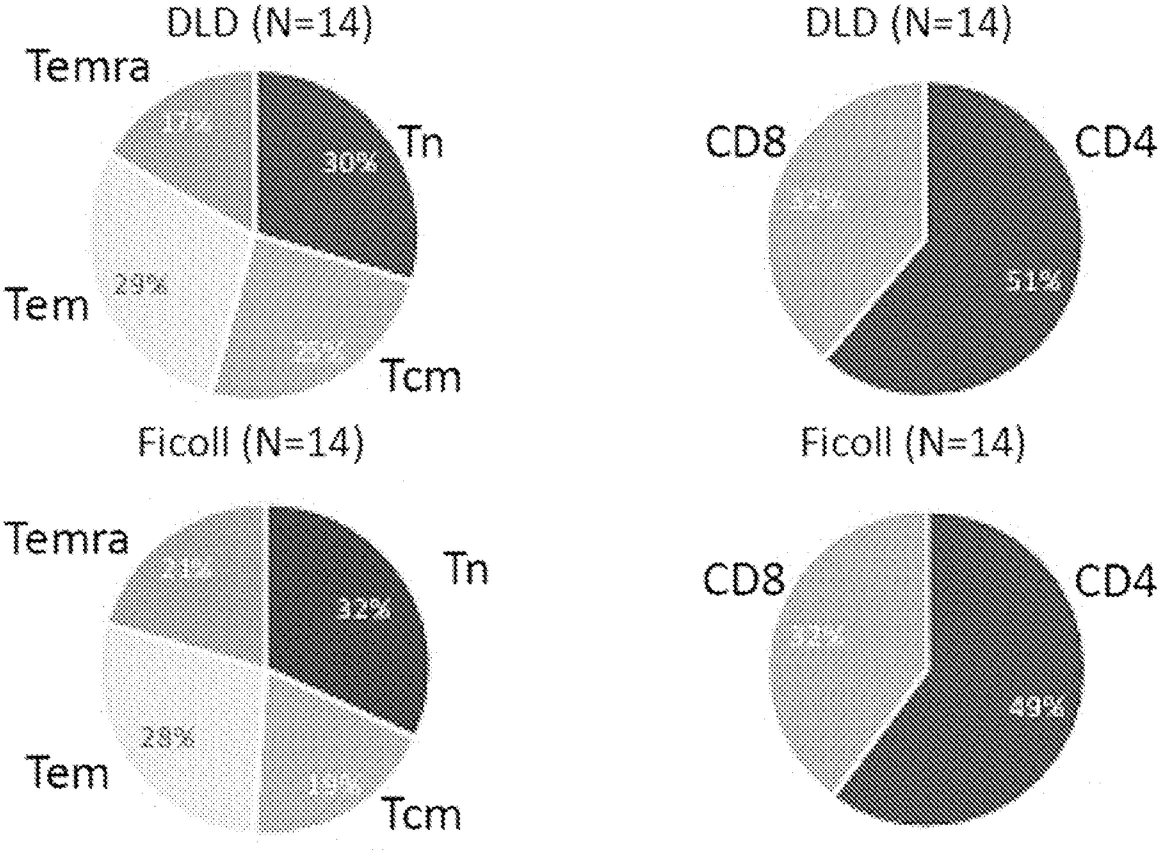
FIG. 14 illustrates that systems and methods herein recover more of the CD4 less differentiated naïve and central memory subsets from leukopaks, at the start of the cell therapy manufacturing at day 0, versus Ficoll.

Example—2 Greater Numbers of Beneficial T Cell Subtypes and Lowered Numbers of Undesired or Deleterious T Cell Subtypes are Recovered on Day 0 after Isolation Compared to Density Gradient Separation The efficacy and safety of T cell therapies depend on the T cell subtypes used in the manufacture of the therapy. Therefore, the T cell subtypes isolated using the DLD system were compared to ficoll purification, which is a common method of isolating T cells from blood and leukapheresis samples. Compared to Ficoll, leukopaks enriched using the DLD system showed a higher percent composition of T central memory cells and less fully differentiated T effector cells. As illustrated in FIG. 14, CD4+ and CD8+ T cell populations were isolated using DLD and Ficoll methods. On average, the DLD method isolated populations were comprised of 30% T naïve cells (CD3+/CD45RA+/CCR7+), 25% T central memory cells (CD3+/CD45RA−/CCR7+), 29% T effector memory cells (CD3+/CD45RA+/CCR7−), and 17% T emra cells (effector memory differentiated) (CD3+/CD45+/CCR7−). On average, Ficoll separated populations were comprised of 32% T naïve cells (CD3+/CD45RA+/CCR7+), 19% T central memory cells (CD3+/CD45RA−/CCR7+), 28% T effector memory cells (CD3+/CD45RA+/CCR7−), and 21% T emra cells (effector memory differentiated) (CD3+/CD45+/CCR7−).

Figure 17:
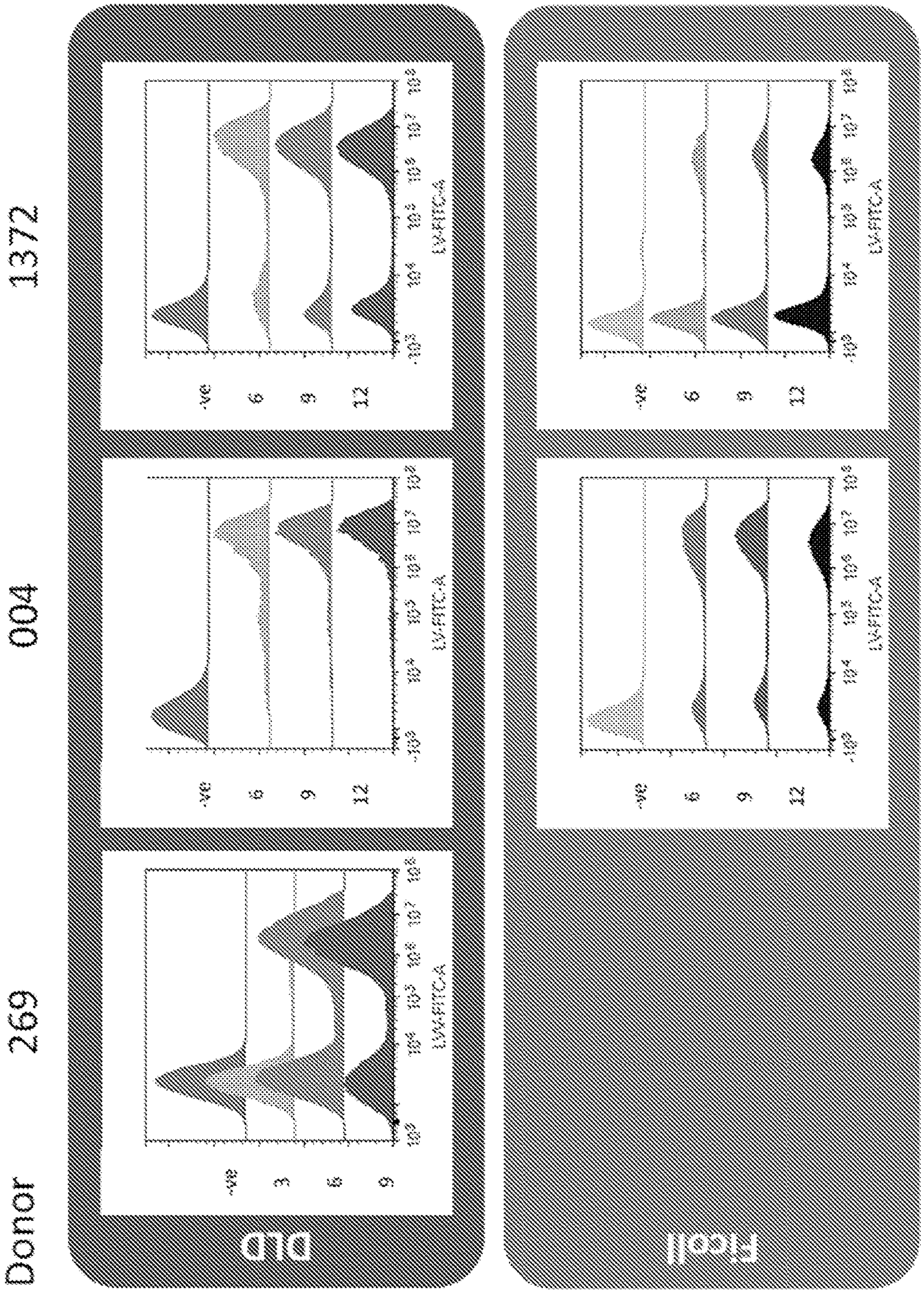
FIG. 17 illustrates that cells enriched according to the systems and methods herein integrate lentivirus more readily compared to Ficoll preparations.
Figure 19:
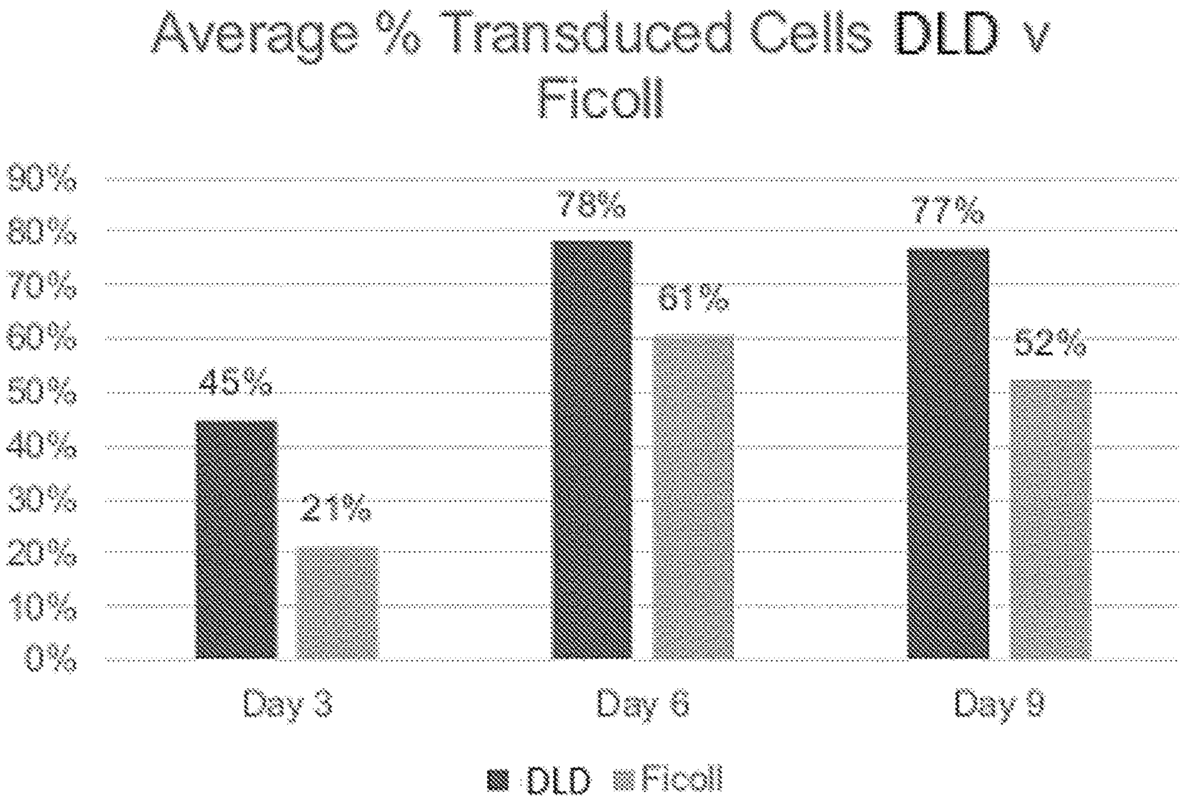
FIG. 19 illustrates that cells enriched according to the systems and methods herein are more receptive to viral transduction compared to Ficoll preparations.

Example 3—T Cell Populations Isolated by DLD are More Receptive to Lentiviral Transduction, are More Efficiently Transduced by Lentivirus, Express Lentiviral Delivered Genes Faster, and Retain More Beneficial T Cell Subtypes as Compared to Density Gradient Separation The timely administration, efficacy, and safety of T cell therapies depend on how amenable isolated T cells are to genetic engineering and subsequent expansion, along with how quickly and efficiently they can express heterologous genetic material. Therefore, the T cell responses to lentiviral transduction, using T cells isolated using the DLD system, were compared to those obtained from ficoll purification. Leukopacks from three different donors were processed, had T cells isolated/activated with CD3/CD28 beads, and were transduced with GFP-Lentivirus. Cell were then expanded in cell culture with TL-7/TL-15 over the course of 9 days. As illustrated in FIG. 17, Cells were analyzed by flow cytometry at the corresponding days, to monitor the uptake and integration of the GFP-Lentivirus and compared to non-transduced cells at 0, 3, 6, 9, and 12 days, showing that DLD-prepared cell populations more readily integrate lentivirus, including at Day 6 which showed a 30% increase in number of integrated cells as compared to Ficoll-prepared cells. FIG. 19 shows the average % of transduced cells in the DLD and Ficoll prepared cell populations, showing that DLD populations are more amenable to lentiviral transduction, in some cases, by 20-100%.

These findings were confirmed using a 9-day time course of immunofluorescence microscopy. T cells from DLD and Ficoll procedures, from the same donor, were isolated/activated and transduced with GFP-Lentivirus and expanded in cell culture. At the indicated times, the cells were examined by microscopy to monitor the GFP-Lentivirus uptake and expression of GFP, showing that DLD cells are more easily transduced than Ficoll cells, as indicated by greater GFP signal in DLD-derived cell populations illustrated in FIG. 18. Thus, cells prepared by DLD and the system are able to be more easily transduced as compared to other systems methods. (see FIGS. 17-19). DLD produced cells are consistently more easily transduced, about 87.5% showing significant improvement versus Ficoll. The average improvement at day 3 was ~2 fold, and at day 6, 9 a 30% advantage was retained. At all times the DLD produced cells averaged a higher transduction level.

Figure 20:
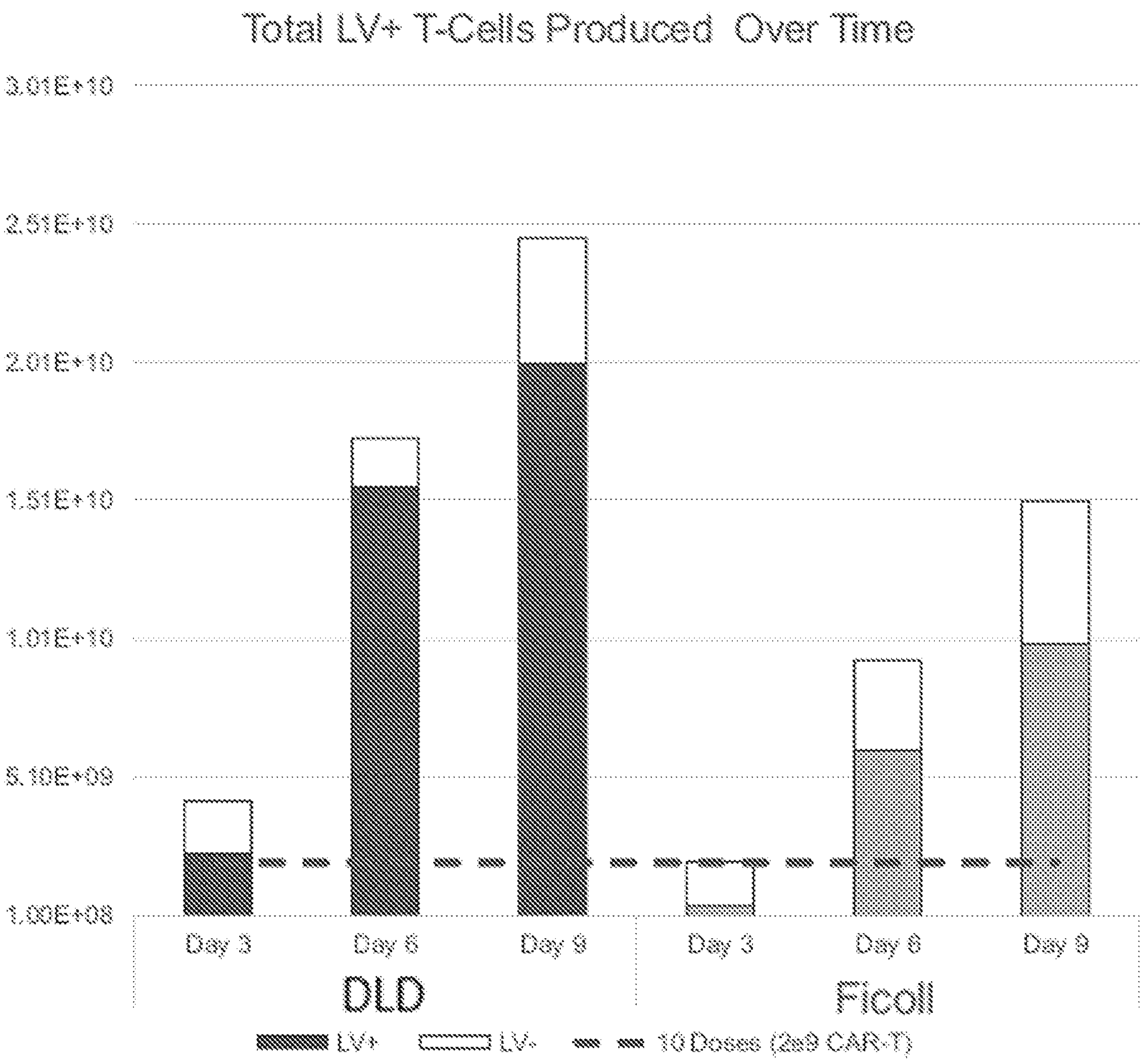
FIG. 20 illustrates that cells enriched according to the systems and methods herein, lentiviral transduced, and expanded, produce more dose equivalents of therapeutic leukocytes at an earlier time point compared to Ficoll preparations.

These findings are especially salient in translating these separation processes to clinical applications. Greater lentiviral transduction efficiency leads to reduced times to dosing i.e. obtaining sufficient numbers of cells for a dose or multiple doses of therapeutic cells. As illustrated in FIG. 20, DLD methods can produce enough lentiviral transduced cells equivalent to 10 doses of therapeutic cells after 3 days in culture and more total doses than Ficoll over a period of 9 days, normalized to an initial input of 200 mL of leukopack material. In some cases, the DLD-prepared cell populations yielded twice as many transduced cells over a period of 9 days.

Figure 21:
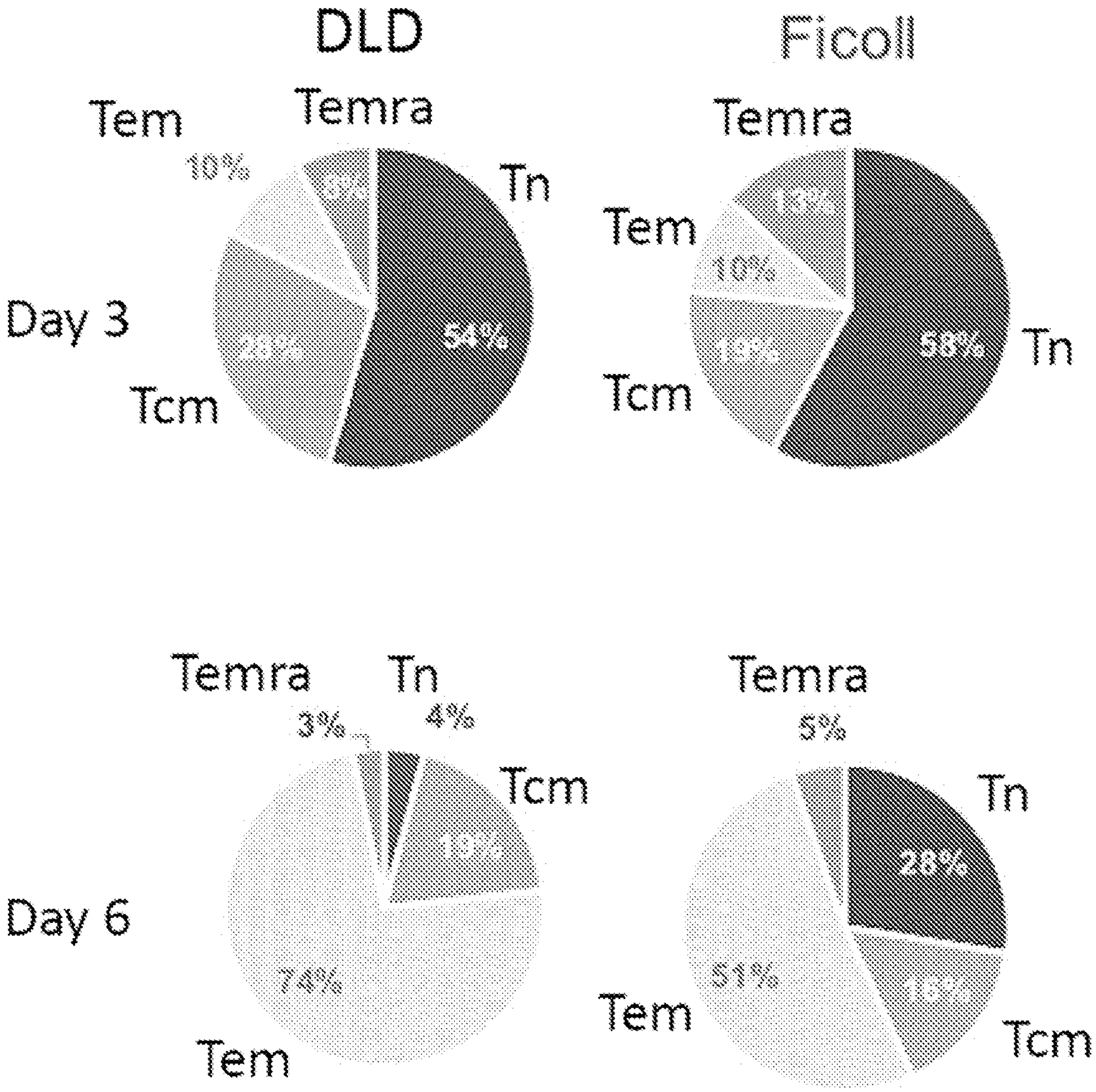
FIG. 21 illustrates that cell populations enriched according to the systems and methods herein, and treated with high integration lentivirus, have fewer terminally differentiated cells compared to Ficoll preparations.

In addition to the number of total cells produced after separation and lentiviral transduction, it is crucial that therapeutic cell doses comprise effectively activated T cell types, such as T central memory and T effector memory cells. The T cell subsets composition of GFP-Lv+ cells at day 3 and day 6 after activation were compared between DLD and Ficoll-prepared cell populations. Determination of T cell subtypes was done by flow cytometry within the GFP-Lv+ T cells, as illustrated in FIG. 21. At Day 6, DLD methods result in a population of T cells comprising 4% T naïve (CD3+/CD45RA+/CCR7+), 19% T central memory (CD3+/CD45RA−/CCR7+), 74% T effector memory (CD3+/CD45RA+/CCR7−), and 3% T emra (CD3+/CD45+/CCR7−). At Day 6, Ficoll methods result in a population of T cells comprising 28% T naïve (CD3+/CD45RA+/CCR7+), 16% T central memory (CD3+/CD45RA−/CCR7+), 51% T effector memory (CD3+/CD45RA+/CCR7−), and 5% T emra (CD3+/CD45+/CCR7−).

Figure 23:
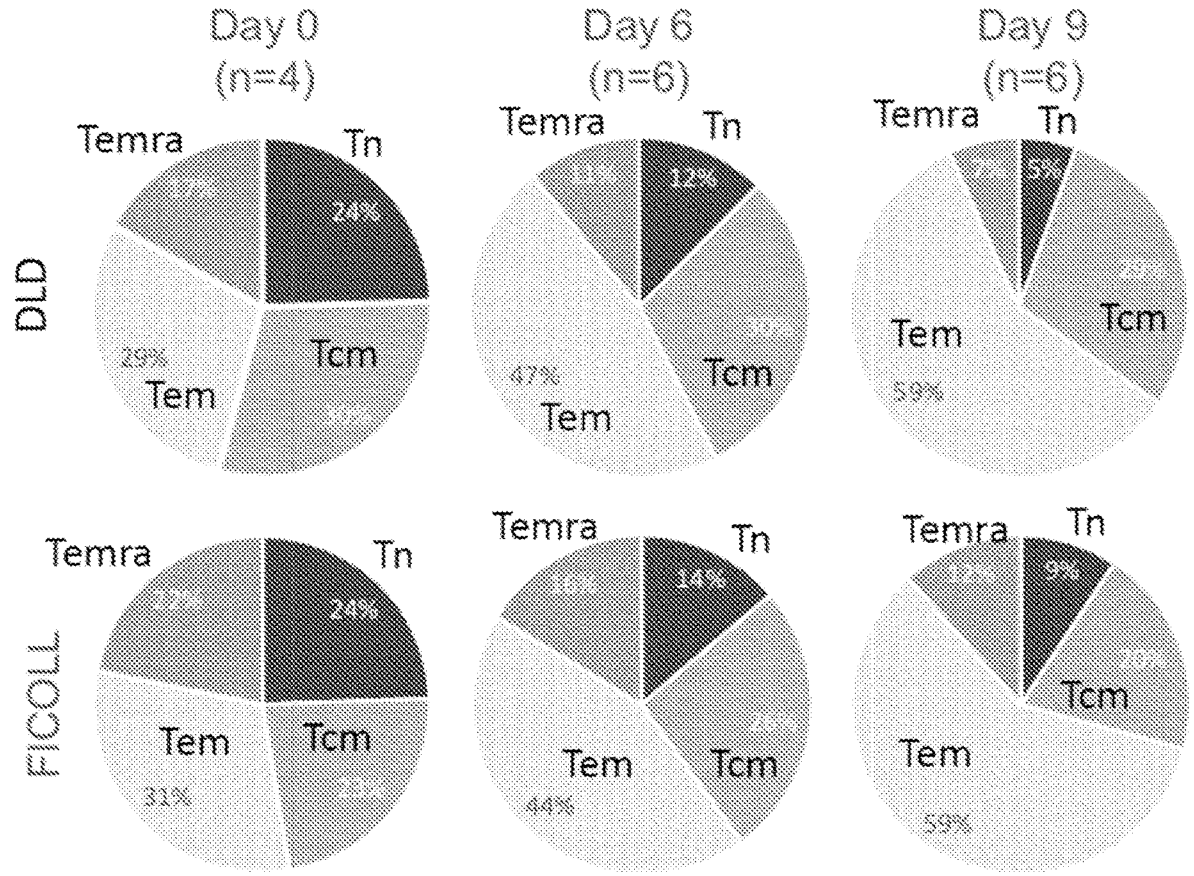
FIG. 23 illustrates that viable CD 3+ memory cell populations enriched according to the systems and methods herein, and treated with high integration lentivirus, retain relative populations of T memory cells compared to Ficoll preparations.

Thus, DLD cells have a larger pool of T cm resulting in a more robust conversion to T em cells as compared to Ficoll GFP=Lv+ T cells. These findings were confirmed with additional experiments comparing cell population T Cell compositions from DLD and Ficoll-prepared compositions (from healthy donors) prior to lentiviral transduction (FIG. 22) and at 3, 6, and 9 days post transduction in culture (FIG. 23). Day 0 (pre-transduction) DLD cells showed a higher number of CD4+ cells and less differentiated T cm cells than Ficoll cells as determined by flow cytometry. Progression of the T cell subtypes with GFP-Lv is illustrated in FIG. 23. Viable CD3+ cells from DLD protocol showed a bias towards Tcm, over time as compared to the cells from the Ficoll protocol. GFP-Lv+ and T cell subsets were determined by flow cytometry. For example, on Day 9, DLD methods result in a population of T cells comprising 5% T naïve (CD3+/CD45RA+/CCR7+), 29% T central memory (CD3+/CD45RA−/CCR7+), 59% T effector memory (CD3+/CD45RA+/CCR7−), and 7% T emra (CD3+/CD45+/CCR7−). At Day 9, Ficoll methods result in a population of T cells comprising 9% T naïve (CD3+/CD45RA+/CCR7+), 20% T central memory (CD3+/CD45RA−/CCR7+), 59% T effector memory (CD3+/CD45RA+/CCR7-), and 12% T emra (CD3+/CD45+/CCR7−).

Example 4—T Cell Populations Isolated by DLD have Lower Expression of Cell Senescence and Exhaustion Markers after Activation, Lentiviral Transduction, and Expansion as Compared to T Cell Populations Prepared with Ficoll Methods Efficacy and manufacture of therapeutic cells relies partially on having populations of viable and expanding cells i.e. not senescent or exhausted T cells. Activated, transduced and expanded T cells were examined for senescence (CD57+/KLRG1+) and exhaustion (CD57/KLRG1+/PD1+/Tim3+) at day 13 and expressed as a ratio of Ficoll/DLD. Ficoll cells transduced with the full CAR19 signaling domain had a more pronounced expression senescence and exhaustion markers (CD57+/KLRG1+ and CD57−/KLRG1+ with PD1 and Tim3 co-expression) than DLD cells, as illustrated in FIG. 24, whereas there was very little difference in cells transduced with the controls of NO CAR or inactive CAR (CAR19-Sig domain).

Figure 25:
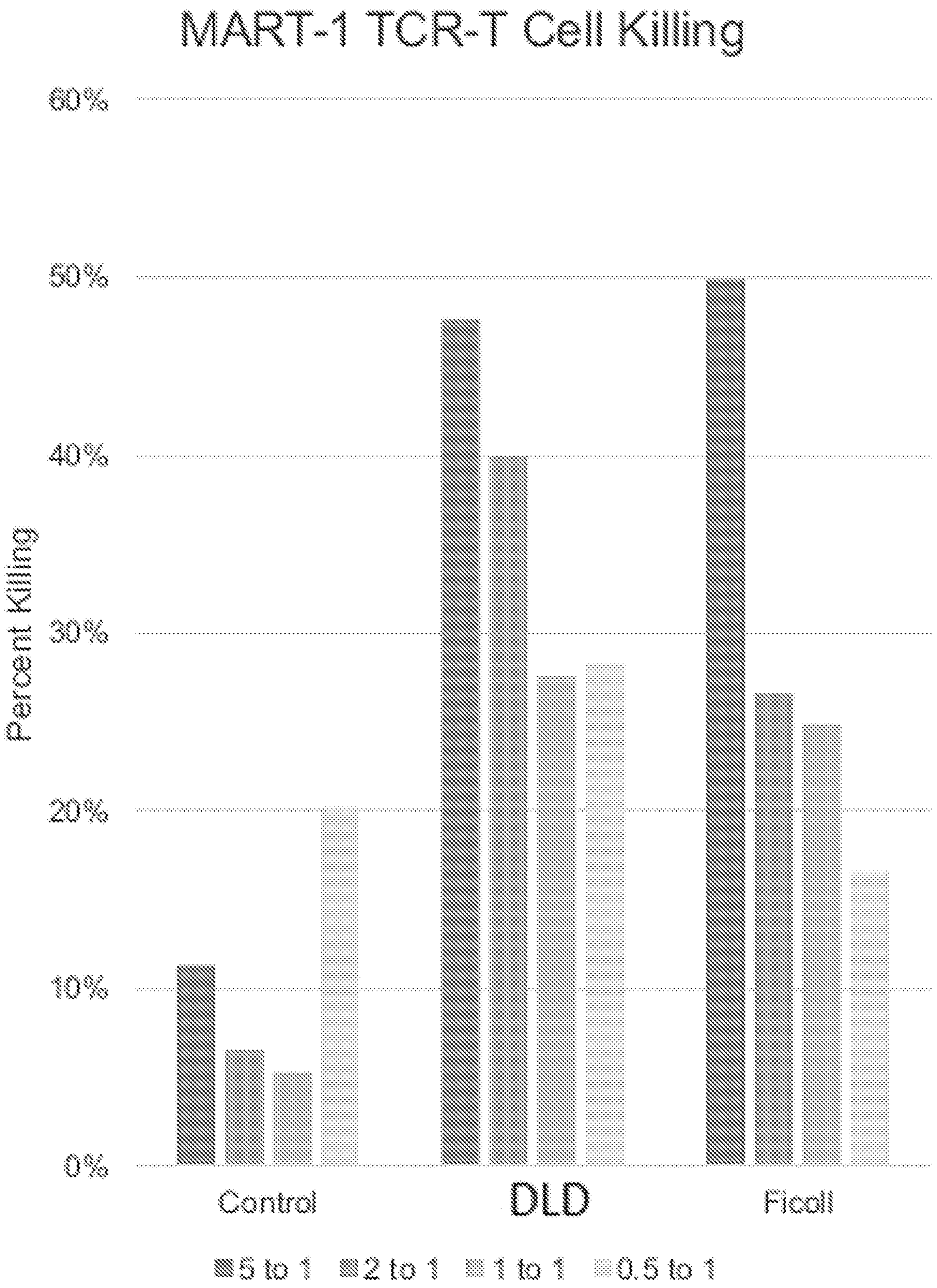
FIG. 25 illustrates that cell populations enriched according to the systems and methods herein have normal or increased killing capacity compared to Ficoll preparations.

Example 5—T Cell Populations Isolated by DLD have Comparable or Increased Killing Capacity as Compared to Those Prepared Using Ficoll Methods Efficacy of therapeutic T cell preparations relies on those cells being effective at killing cells comprising a targeted peptide sequence. T cells from DLD or Ficoll were isolated, activated and transduced with a TCRT lentivirus specific for the MART-1 antigen. At day 6 cells were collected and co-cultured with T2 target cells (Luc+) bearing the MART-1 peptide at different ratios. Upon incubation the T2 cell mortality was examined by the loss of chemiluminescence in the co-culture. Both DLD and Ficoll cells were capable of killing their target cells in a dose-dependent manner. As illustrated in FIG. 25, cells prepared using DLD methods exhibited higher killing capacities at 2:1, 1:1, and 0.5:1 T cells to target cell ratios than those prepared using Ficoll, a 30% increase in killing in some cases.

Example 6—T Cell Populations Isolated by DLD have Higher Desirable Cytokine Expression and Lower Undesirable Cytokine Expression as Compared to T Cell Populations Isolated by Ficoll Therapeutic T cell preparation safety relies partly on isolating cells that will result in more cell killing activity as opposed to inflammatory responses in order to avoid adverse effects to patients. As such, it is desirable that T cell populations prepared using various isolation methods express more cell-killing cytokines and have low inflammatory response cytokine expression. As such, cytokine expression was compared between T cell populations isolated using DLD and Ficoll methods.

Figure 26:
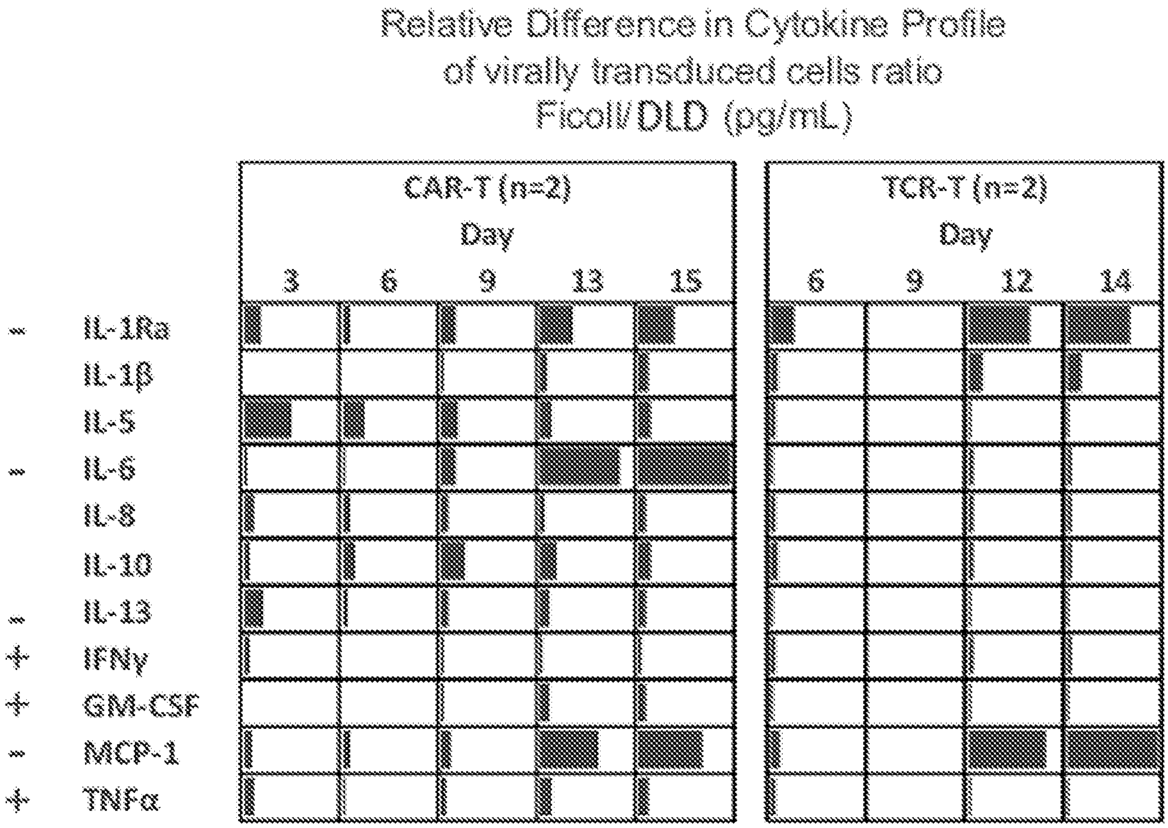
FIG. 26 illustrates that cell populations enriched according to the systems and methods herein have a more favorable cytokine expression during expansion and thus a more favorable safety profile compared to Ficoll preparations.
Figure 27:
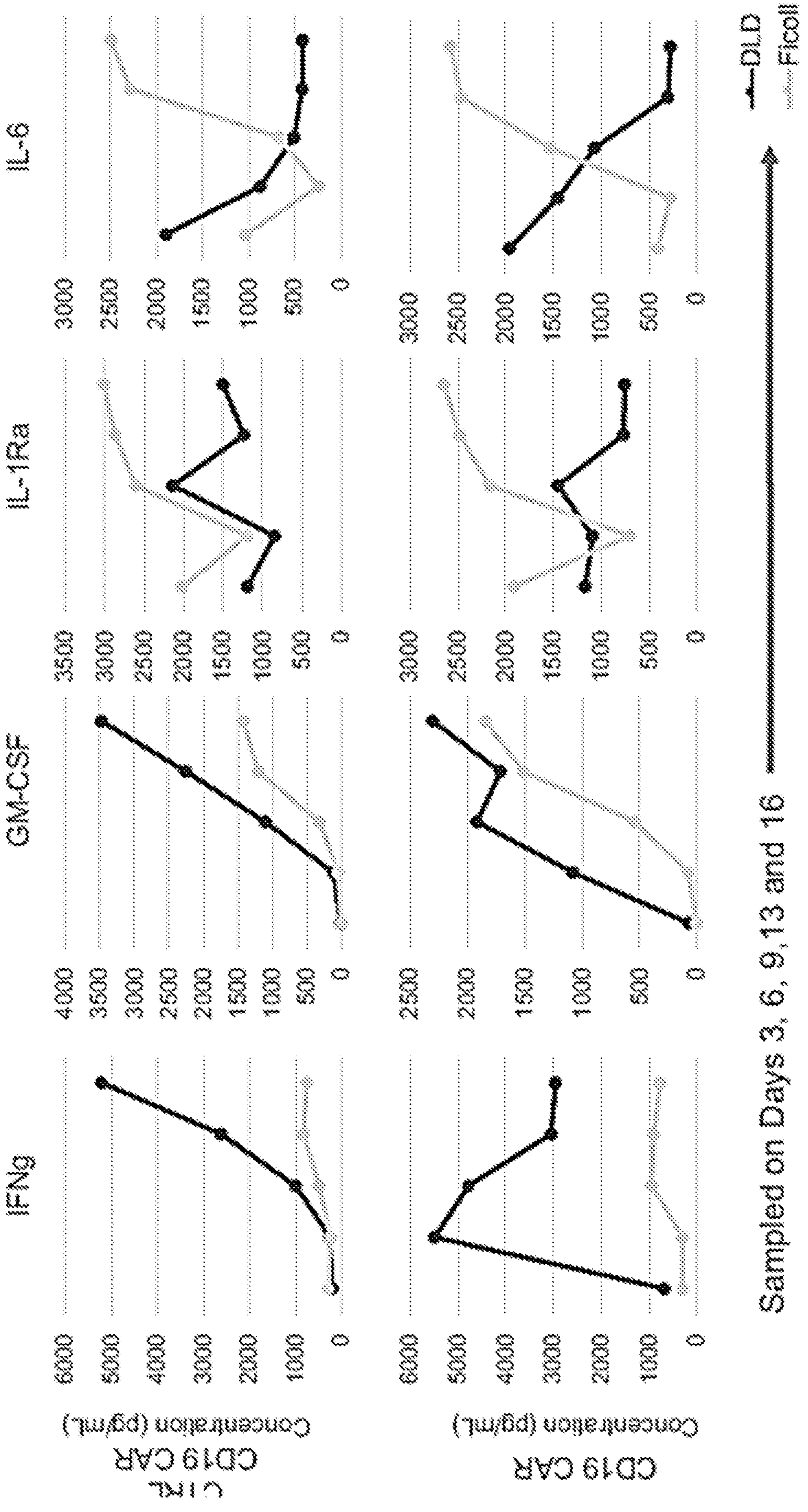
FIG. 27 illustrates that cell populations enriched according to the systems and methods herein have a more favorable cytokine expression during expansion and thus a more favorable safety profile compared to Ficoll preparations, as demonstrated with cytokine release with CD19 CAR-T constructs (+/− functional CD28 signaling domain).
Figure 28:
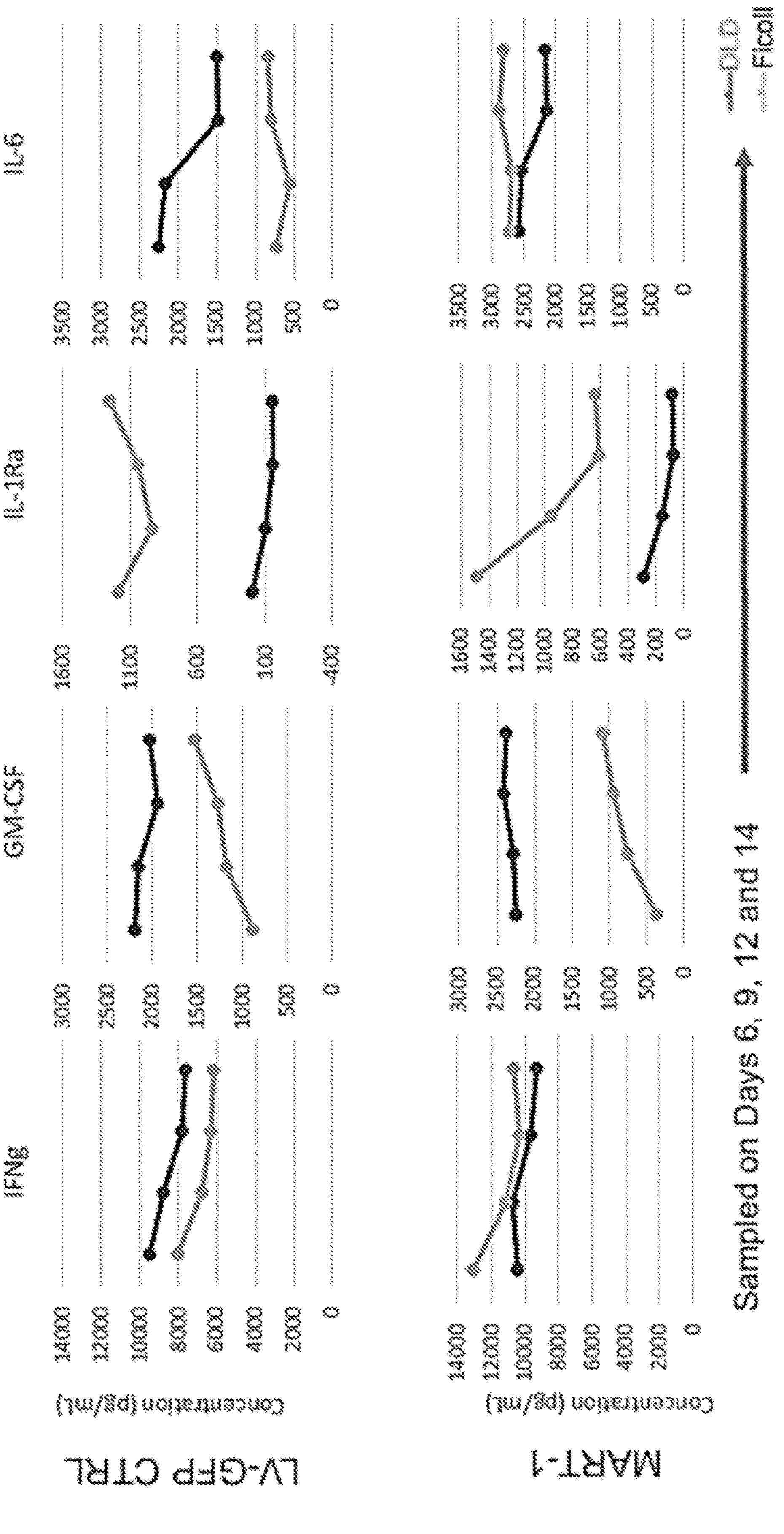
FIG. 28 illustrates that cell populations enriched according to the systems and methods herein have a more favorable cytokine expression during expansion and thus a more favorable safety profile compared to Ficoll preparations, as demonstrated with cytokine release with TCR-T constructs and lentiviral-GFP controls.

Supernatants from DLD and Ficoll cells were collected at days 0, 6 and 13 after T cell isolation/activation, expansion (IL7/IL-15), and lentiviral transduction (CAR-T-CD19 or TCRT-MART-1). 15 different cytokines were analyzed by a Luminex multiplex assay for all of the supernatants. The results are expressed as the ratio of Ficoll/DLD (pg/ml), as illustrated in FIG. 26. Time course cytokine expression for IFNg, GM-CSF, IL-1Ra, and IL-6 in CAR-T-CD19 transduced cells is illustrated in FIG. 27. Time course cytokine expression for IFNg, GM-CSF, IL-1Ra, and IL-6 in TCRT-MART-1 transduced cells is illustrated in FIG. 28. Ficoll cells secreted more IL-6, MCP-1 and IL-1Ra involved in the inflammatory response, whereas DLD cells expressed more IFNg and GM-CSF, typical markers of cell killing activity. Thus, DLD-prepared T cell populations exhibit a more favorable cytokine expression profile.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

EXAMPLE EMBODIMENTS

1. A system for generating a product enriched in one or more target particles, comprising:

a cassette comprising (i) one or more cartridge ports, (ii) at least one inlet for receiving a sample, (iii) at least one outlet for outputting the product, and (iv) at least one recirculating pathway; and one or more microfluidic cartridges operably coupled to the one or more cartridge ports to establish fluidic communication with the cassette, such that the one or more microfluidic cartridges are used to separate the one or more target particles from the sample, the at least one recirculating pathway is used to recirculate the one or more target particles through the cassette to concentrate the one or more target particles into a predefined volume of media or to a predefined concentration, and the one or more microfluidic cartridges and the at least one recirculating pathway are operated in parallel to optimize a run time for generating the product.

2. The system of embodiment 1, wherein the one or more microfluidic cartridges and the at least one recirculating pathway are operated independently of each other.

3. The system of embodiment 1, wherein the one or more microfluidic cartridges are configured to separate the one or more target particles from the sample without affecting a recirculation process by the at least one recirculating pathway.

4. The system of embodiment 1, wherein the at least one recirculating pathway is configured to recirculate the one or more target particles through the cassette without affecting a separation process by the one or more microfluidic cartridges.

5. The system of embodiment 2, wherein the one or more microfluidic cartridges and the at least one recirculating pathway are individually controllable in real-time to achieve a desired concentration of the one or more target particles in the product.

6. The system of embodiment 1, wherein the at least one recirculating pathway extends between the at least one inlet and the at least one outlet.

7. The system of embodiment 1, wherein the at least one recirculating pathway is configured to recirculate the one or more target particles in a clockwise direction on the cassette.

8. The system of embodiment 1, wherein the at least one recirculating pathway is configured to recirculate the one or more target particles in a counter-clockwise direction on the cassette.

9. The system of embodiment 1, wherein the cassette further comprises a plurality of pathways for directing the sample into and out of the one or more microfluidic cartridges.

10. The system of embodiment 9, wherein the at least one recirculating pathway is provided separate from the plurality of pathways.

11. The system of embodiment 9, wherein the at least one recirculating pathway is adjoined or connected to one or more of the plurality of pathways.

12. A system for generating a product enriched in one or more target particles, comprising:

a cassette to which the one or more microfluidic cartridges are releasably coupled and supported, the cassette comprising a plurality of fluidic channels extending longitudinally and spaced apart on the cassette; and a plurality of pumps peristaltically coupled to the plurality of fluidic channels to control flow of fluidic content through the plurality of fluidic channels downstream to the one or more microfluidic cartridges for separation of one or more target particles from the sample, without any moving parts from the pumps directly contacting the fluidic content during its flow.

13. The system of embodiment 12, wherein the plurality of fluidic channels comprises flexible tubing.

14. The system of embodiment 12, wherein each of the plurality of pumps comprises a set of pump heads that are peristaltically coupled to each subset of the plurality of fluidic channels.

15. The system of embodiment 14, wherein the set of pump heads in each pump comprises two or more pump heads.

16. The system of embodiment 15, wherein the two or more pump heads comprises two or more sets of rollers.

17. The system of embodiment 16, wherein each subset of the plurality of fluidic channels comprises two or more fluidic channels.

18. The system of embodiment 12, wherein the fluidic content comprises the sample, a media solution, a diluent, and waste that is generated by the one or more microfluidic cartridges after the one or more target particles have been separated from the sample.

19. The system of embodiment 18, wherein the fluidic content further comprises a priming solution.

20. The system of embodiment 18, wherein the fluidic content further comprises a recirculated solution comprising a concentrated amount of the one or more target particles.

21. The system of embodiment 18, wherein the plurality of pumps comprises a first pump for controlling a flow of the sample, a second pump for controlling a flow of the media solution, a third pump for controlling a flow of the diluent, and a fourth pump for controlling a flow of the waste.

22. The system of embodiment 18, wherein the plurality of pumps are individually controllable to modulate relative flowrates between the sample, the media solution, the diluent, and the waste.

23. The system of embodiment 14, wherein the set of pump heads in each pump are configured to actuate out-of-phase relative to each other.

24. The system of embodiment 23, wherein the set of pump heads in each pump actuate out-of-phase by less than or equal to about 180 degrees.

25. The system of embodiment 14, wherein the set of pump heads in each pump have a fixed motion relative to each other.

26. The system of embodiment 25, wherein the fixed motion comprises the set of pump heads in each pump moving at a same rate and in a same direction relative to each other.

27. The system of embodiment 14, wherein, for each pump and each subset of fluidic channels, the fluidic content transported by the set of pump heads is combined together at an outlet of each subset of fluidic channels into a single fluid path.

28. The system of embodiment 14, wherein a pulsatility of each pump is reduced by moving the set of pump heads out of phase.

29. The system of embodiment 22, wherein the plurality of pumps are individually controllable to (a) control a ratio of an amount of the waste relative to an amount of the sample, (b) control a ratio of an amount of the sample relative to an amount of the diluent, or (c) adjust a dilution factor.

30. The system of embodiment 12, wherein the plurality of pumps are individually controllable to be in phase or out of phase relative to each other.

31. The system of embodiment 12, wherein the plurality of pumps are individually controllable to achieve a same flow rate, different flow rates, a same flow direction, or different flow directions.

32. The system of embodiment 12, wherein the plurality of pumps are individually controllable to adjust the flow of the fluidic content in real-time as the one or more microfluidic cartridges are separating out the one or more target particles from the sample.

33. The system of embodiment 12, wherein the plurality of pumps are individually controllable to enable a desired concentration of the one or more target particles in the product.

34. The system of embodiment 12, wherein the plurality of pumps comprises peristaltic pumps.

35. A system for generating a product enriched in one or more target particles, comprising:
- one or more microfluidic cartridges that are configured to separate the one or more target particles from a sample;
- one or more sensors for detecting a presence of air bubbles in the sample or another solution;
- one or more controllable valves; and
- a cassette to which the one or more microfluidic cartridges are releasably coupled and supported, the cassette comprising one or more bypass channels downstream of the one or more controllable valves for diverting a portion of the sample or the another solution having the air bubbles away from the one or more microfluidic cartridges, based on a detection of the presence of the air bubbles by the one or more sensors.

36. The system of embodiment 35, wherein the one or more sensors are used for detecting the presence of the air bubbles prior to circulating the sample into the one or more microfluidic cartridges.

37. The system of embodiment 35, wherein the system is configured to generate one or more alerts upon the one or more sensors detecting the presence of air bubbles in the sample or the another solution.

38. The system of embodiment 35, wherein the one or more sensors and the one or more bypass channels work in concert to prevent the air bubbles from entering and reducing an efficiency of the one or more microfluidic cartridges.

39. The system of embodiment 35, wherein the one or more sensors and the one or more bypass channels work in concert to reduce or eliminate contamination in the product.

40. A system for generating a product enriched in one or more target particles, comprising:
- one or more microfluidic cartridges that are configured to separate the one or more target particles from a sample;
- a cassette to which the one or more microfluidic cartridges are releasably coupled and supported; and
- at least one degassing unit for removing dissolved gases and preventing bubble formation prior to the sample being circulated through the one or more microfluidic cartridges.

41. The system of embodiment 40, wherein the at least one degassing unit is integrated onto the cassette.

42. The system of embodiment 40, wherein the at least one degassing unit is fabricated as part of the cassette.

43. The system of embodiment 40, wherein the at least one degassing unit is located on the cassette in proximity to the one or more microfluidic cartridges.

44. The system of embodiment 40, wherein the at least one degassing unit is in fluidic communication with a plurality of pathways leading into the one or more microfluidic cartridges.

45. A system for generating a product enriched in one or more target particles, comprising:
- a cassette to which the one or more microfluidic cartridges are releasably coupled and supported, the cassette comprising (i) a plurality of inlets having a plurality of input containers releasably and fluidically coupled thereto, wherein at least one of the plurality of input containers comprises an incoming sample, (ii) a plurality of outlets having a plurality of output containers releasably and fluidically coupled thereto, (iii) one or more microfluidic cartridges for separating one or more target particles from the sample, and (iv) a plurality of fluidic channels extending between the plurality of inlets, the plurality of outlets, and the one or more microfluidic cartridges,
- wherein the cassette having the plurality of input containers, the plurality of output containers, and the one or more microfluidic cartridges coupled thereto, collectively provides a closed end-to-end sterile environment that enables inline continuous processing of the incoming sample without external manual handling or intervention, so as to generate a product that is enriched in one or more target particles and free of contamination.

46. The system of embodiment 45, wherein the plurality of inlets and the plurality of input containers are releasably and fluidically coupled using a plurality of sterile coupling mechanisms.

47. The system of embodiment 46, wherein the plurality of sterile coupling mechanisms comprises at least one sterile spike and at least one spike port.

48. The system of embodiment 45, wherein the product is collected in at least one of the plurality of output containers.

49. The system of embodiment 45, wherein the product is collected in at least one of the plurality of output containers without exposing the product to an external non-sterile environment.

50. The system of embodiment 45, wherein the product is collected in at least one of the plurality of output containers without exposing the product to an external non-sterile environment.

51. The system of embodiment 45, wherein the sample is input from the at least one of the plurality of input containers into the cassette without exposing the sample to an external non-sterile environment.

52. The system of embodiment 45, wherein the system does not require any intermediary reagent to be externally added from outside of the closed end-to-end sterile environment during the inline continuous processing of the incoming sample.

53. The system of embodiment 45, wherein the system does not require any intermediary byproduct to be removed outside of the closed end-to-end sterile environment during the inline continuous processing of the incoming sample.

54. The system of embodiment 45, wherein the sample has a volume of at least about 200 mL, and the system is configured to process the sample to generate in less than 1 hour the product being enriched with at least about 70% of the one or more target particles.

55. The system of embodiment 45, wherein the system is configured to process the sample at a rate equal to or greater than about 300 mL/hr.

56. A system for generating a product enriched in one or more target particles, comprising:
- one or more microfluidic cartridges that are configured to separate the one or more target particles from a sample; and
- a cassette to which the one or more microfluidic cartridges are releasably coupled and supported, the cassette comprising a mixer that is configured to mix the sample with a diluent inline on the cassette without using any moving parts, prior to the sample being circulated through the one or more microfluidic cartridges.

57. The system of embodiment 56, wherein the mixer comprises a first fluidic channel for the sample and a second fluidic channel for the diluent.

58. The system of embodiment 57, wherein the first fluidic channel and the second fluidic channel converge to permit mixing of the sample and the diluent.

59. The system of embodiment 57, wherein the first fluidic channel and the second fluidic channel comprise a plurality of structural elements for facilitating inline mixing of the sample and the diluent.

60. A method comprising:

(a) providing a system comprising a cassette to which one or more microfluidic cartridges are releasably coupled and supported;

(b) priming the cassette by flowing a priming solution through the system;

(c) processing a sample by flowing the sample through the system and using the one or more microfluidic cartridges to separate one or more target particles from the system;

(d) collecting a product comprising the one or more target particles that have been separated from the sample, wherein the sample has a volume of at least about 40 mL, the product is enriched with at least about 70% recovery of the one or more target particles, and (b) through (d) are completed continuously inline in a closed sterile environment in less than or equal to about 1 hour.

61. The method of embodiment 60, wherein (b) is completed in less than or equal to about 20 minutes.

62. The method of embodiment 60, wherein (c) and (d) are completed in less than or equal to about 40 minutes.

63. The method of embodiment 60, wherein the cassette and the one or more microfluidic cartridges are configured for single use.

64. The method of embodiment 60, wherein (b) permits the cassette to be reusable for multiple use.

65. The method of embodiment 60, wherein (b) permits the one or more microfluidic cartridges to be reusable for multiple use.

66. The method of any one of embodiments 60 to 65, wherein the sample is a human sample.

67. The method of any one of embodiments 60 to 66, wherein the sample comprises a blood-related product.

68. The method of embodiment 67, wherein the blood-related product comprises an apheresis product.

69. The method of embodiment 68, wherein the apheresis product is a leukapheresis product.

70. The method of any one of embodiments 60 to 69, wherein the one or more target particles that have been separated from the sample comprise cells.

71. The method of embodiment 70, wherein the cells are human cells.

72. The method of embodiment 70 or 71, wherein the cells are greater than about 90% viable upon recovery.

73. The method of any one of embodiments 70 to 72, wherein the cells comprise peripheral blood mononuclear cells.

74. The method of any one of embodiments 70 to 73, wherein the cells comprise CD3+ T cells.

75. The method of embodiment 74, wherein the T cells exhibit a naïve or central memory phenotype.

76. The method of any one of embodiments 70 to 75, further comprising culturing or expanding the cells in vitro.

77. The method of any one of embodiments 70 to 76, further comprising rendering the cells transgenic with an exogenous nucleic acid.

78. The method of embodiment 77, wherein the exogenous nucleic acid encodes a chimeric antigen receptor or a recombinant T cell receptor.

79. The method of embodiment 60, wherein the sample has a volume of at least about 300 mL.

80. The method of embodiment 60, wherein the sample has a volume of at least about 100 mL.

81. The method of embodiment 60, wherein the product is enriched with at least about 80% recovery of the one or more target particles.

82. The method of embodiment 60, wherein the product is enriched with at least about 90% recovery of the one or more target particles.

83. The method of embodiment 60, wherein the product is enriched with at least about 95% recovery of the one or more target particles.

84. A method comprising:

displaying a graphical user interface (GUI) on a computer, the GUI comprising (i) a control panel and (ii) a visual representation of a system, the system comprising (a) a cassette to which one or more microfluidic cartridges are releasably coupled and supported, and (b) a plurality of components for facilitating fluidic transport and process control;

receiving user input for a run protocol entered via the control panel;

activating the run protocol on the system to process a sample by using the one or more microfluidic cartridges to separate one or more target particles from the sample; and displaying substantially in real-time a progress or status as the system is processing the sample, wherein the progress or status is depicted by graphical changes to the visual representation of the system.

85. The method of embodiment 84, wherein the plurality of components comprises flow channels, valves, pressure sensors, and pumps.

86. The method of embodiment 85, wherein the plurality of components further comprises one or more bubble sensors and at least one degassing unit.

87. The method of embodiment 86, wherein the graphical changes comprise an on/off status of one or more of the plurality of components.

88. The method of embodiment 86, wherein the graphical changes comprise a fluidic flow of the sample or other media through the cassette and the one or more microfluidic cartridges.

89. The method of embodiment 84, further comprising: generating one or more notifications on the GUI that indicate that the system is processing the sample in accordance with the run protocol.

90. The method of embodiment 84, further comprising: generating one or more notifications on the GUI that indicate that the system is experiencing one or more deviations from the run protocol as the sample is being processed.

91. The method of embodiment 90, further comprising: generating one or more options on the GUI for a user to rectify the one or more deviations.

92. The method of embodiment 90, further comprising: automatically reducing a pressure and a flow rate of the sample upon detection of the one or more deviations from the run protocol.

93. The method of embodiment 84, further comprising: generating a report comprising a plurality of run metrics when the system has completed processing the sample.

94. The method of embodiment 84, wherein the GUI allows a user to view a status and control an operation of one or more of the plurality of components substantially in real-time as the system processing the sample.

95. The system of embodiment 1, wherein the system further comprises one or more mass sensors, and wherein the recirculation of the one or more target particles through the cassette is controlled based on one or more readings obtained from the one or more mass sensors.

96. The system of embodiment 40, wherein the system further comprises a panel operably coupled to the cassette, and wherein the at least one degassing unit is integrated onto the panel.

97. The method of embodiment 60, wherein the sample has a volume of at least about 100 mL.

98. The method of embodiment 60, wherein the sample has a volume of at least about 150 mL.

99. The method of embodiment 60, wherein the sample has a volume of at least about 200 mL.

100. The system of any one of embodiments 1 to 59 or the method of any one of embodiments 60 to 99, wherein leukocytes are enriched to at least about 85% or greater of a resulting product.

101. The system of any one of embodiments 1 to 59 or the method of any one of embodiments 60 to 99, wherein leukocytes are enriched to at least about 90% or greater of a resulting product.

102. The system of any one of embodiments 1 to 59 or the method of any one of embodiments 60 to 99, wherein leukocytes are enriched to at least about 85% or greater of a resulting product.

103. The system of any one of embodiments 1 to 59 or the method of any one of embodiments 60 to 99, wherein at least about $2\times10^9$ leukocytes are obtained from a leukopak of at least about 200 mL.

104. The system of any one of embodiments 1 to 59 or the method of any one of embodiments 60 to 99, wherein at least about $2\times10^9$ leukocytes are obtained from a leukopak of at least about 300 mL.

105. The system of any one of embodiments 1 to 59 or the method of any one of embodiments 60 to 99, wherein at least about $2\times10^9$ leukocytes are obtained from a 100 mL leukopak.

106. The system of any one of embodiments 1 to 59 or the method of any one of embodiments 60 to 99, wherein at least about $5\times10^9$ leukocytes are obtained from a leukopak of at least about 200 mL.

107. The system of any one of embodiments 1 to 59 or the method of any one of embodiments 60 to 99, wherein at least about $5\times10^9$ leukocytes are obtained from a leukopak of at least about 300 mL.

108. The system of any one of embodiments 1 to 59 or the method of any one of embodiments 60 to 99, wherein at least about $5\times10^9$ leukocytes are obtained from a leukopak of at least about 100 mL.

109. The system of any one of embodiments 1 to 59 or the method of any one of embodiments 60 to 99, wherein enriched leukocytes possess a telomere length of at least about 2 kilobases.

110. The system of any one of embodiments 1 to 59 or the method of any one of embodiments 60 to 99, wherein enriched leukocytes possess a telomere length of at least about 3 kilobases.

111. The system of any one of embodiments 1 to 59 or the method of any one of embodiments 60 to 99, wherein enriched leukocytes possess a telomere length of at least about 5 kilobases.

112. The system of any one of embodiments 1 to 59 or the method of any one of embodiments 60 to 99, wherein at least about $4\times10^8$ naïve T cells are obtained from a leukopak of at least about 200 mL.

113. The system of any one of embodiments 1 to 59 or the method of any one of embodiments 60 to 99, wherein at least about $4\times10^8$ naïve T cells are obtained from a leukopak of at least about 300 mL.

114. The system of any one of embodiments 1 to 59 or the method of any one of embodiments 60 to 99, wherein at least about $4\times10^8$ naïve T cells are obtained from a leukopak of at least about 100 mL.

115. The system of any one of embodiments 1 to 59 or the method of any one of embodiments 60 to 99, wherein at least about $5\times10^8$ central memory T cells are obtained from a leukopak of at least about 200 mL.

116. The system of any one of embodiments 1 to 59 or the method of any one of embodiments 60 to 99, wherein at least about $5\times10^8$ central memory T cells are obtained from a leukopak of at least about 300 mL.

117. The system of any one of embodiments 1 to 59 or the method of any one of embodiments 60 to 99, wherein at least about $5\times10^8$ central memory T cells are obtained from a leukopak of at least about 100 mL.

118. The system of any one of embodiments 1 to 59 or the method of any one of embodiments 60 to 99, wherein a product comprising at least about 1.5-fold, about 2.5 fold, or about 5 more leukocytes is obtained as compared to the number of leukocytes obtained by using a density gradient centrifugation method.

119. The system of any one of embodiments 1 to 59 or the method of any one of embodiments 60 to 99, wherein a product comprising CD 3+ cells, CD 45+ cells, CD 4+ cells, CD4+ naïve cells, CD 4+ memory cells, CD 4+ effector cells, CD 8+ cells, CD 8+ naïve cells, CD 8+ effector cells, CD 8+ memory cells, memory cells, effector cells, naïve cells, Temra cells, or any combination thereof is obtained.

120. The system of any one of embodiments 1 to 59 or the method of any one of embodiments 60 to 99, wherein a product comprising at least about 1.5-fold, about 2.5-fold, or about 5-fold more CD 45+ cells is obtained as compared to those obtained by using a density gradient centrifugation method.

121. The system of any one of embodiments 1 to 59 or the method of any one of embodiments 60 to 99, wherein a product comprising at least about 1.5-fold, about 2.5-fold, or about 5-fold more CD 3+ cells is obtained as compared to those obtained by using a density gradient centrifugation method.

122. The system of any one of embodiments 1 to 59 or the method of any one of embodiments 60 to 99, further comprising removing one or more target particles from the sample.

123. The method or system of embodiment 122, wherein the target particles are cells.

124. The method or system of embodiment 123, wherein the cells are red blood cells or platelets.

125. The method or system of embodiment 124, wherein at least about 95% of the red blood cells are removed from the sample.

126. The method of embodiment or system 124, wherein at least 95% of the platelets are removed from the sample.

127. The system of any one of embodiments 1 to 59 or the method of any one of embodiments 60 to 99, wherein a product is produced that comprises a mixture of red blood cells and leukocytes at a ratio less than 2.5:1, 1.5:1, or 0.7:1.

128. The system of any one of embodiments 1 to 59 or the method of any one of embodiments 60 to 99, wherein a product is produced that comprises a mixture of platelets and leukocytes at a ratio less than 9:1, 5:1, 3:1, 1.1:1.

129. The system of any one of embodiments 1 to 59 or the method of any one of embodiments 60 to 99, wherein a product is produced that comprises at least about 1.5-fold, about 2.5-fold, or about 5-fold more CD 4+ cells are obtained as compared to those obtained by using a density gradient centrifugation method.

130. The system of any one of embodiments 1 to 59 or the method of any one of embodiments 60 to 99, wherein a product is produced that comprises at least about 1.5-fold, about 2.5-fold, or about 5-fold more CD 8+ cells are obtained as compared to those obtained by using a density gradient centrifugation method.

131. The system of any one of embodiments 1 to 59 or the method of any one of embodiments 60 to 99, wherein a product is produced that comprises at least about 1.5-fold, about 2.5-fold, about 5-fold more naïve CD 4+ cells are obtained as compared to those obtained by using a density gradient centrifugation method.

132. The system of any one of embodiments 1 to 59 or the method of any one of embodiments 60 to 99, wherein a product is produced that comprises at least about 1.5-fold, about 2.5-fold, or about 2.5-fold more memory CD 4+ cells are obtained as compared to those obtained by using a density gradient centrifugation method.

133. The system of any one of embodiments 1 to 59 or the method of any one of embodiments 60 to 99, wherein a product is produced that comprises at least about 1.5-fold, about 2.5-fold, or about 2.5-fold more effector CD 4+ cells are obtained as compared to those obtained by using a density gradient centrifugation method.

134. The system of any one of embodiments 1 to 59 or the method of any one of embodiments 60 to 99, wherein a product is produced that comprises at least about 1.5-fold, about 2.5-fold, about 5-fold more naïve CD 8+ cells are obtained as compared to those obtained by using a density gradient centrifugation method.

135. The system of any one of embodiments 1 to 59 or the method of any one of embodiments 60 to 99, wherein a product is produced that comprises at least about 1.5-fold, about 2.5-fold, or about 5-fold more memory CD 8+ cells are obtained as compared to those obtained by using a density gradient centrifugation method.

136. The system of any one of embodiments 1 to 59 or the method of any one of embodiments 60 to 99, wherein a product is produced that comprises at least about 1.5-fold, about 2.5-fold, about 5-fold more effector CD 8+ cells are obtained as compared to those obtained by using a density gradient centrifugation method.

137. The system of any one of embodiments 1 to 59 or the method of any one of embodiments 60 to 99, wherein a product is produced that comprises at least about 1.5-fold, about 2.5-fold, or about 5-fold more leukocytes are obtained as compared to the number of leukocytes obtained by using a density gradient centrifugation method.

138. The system of any one of embodiments 1 to 59 or the method of any one of embodiments 60 to 99, wherein a product is produced that comprises at least 1.5-fold, about 2.5-fold, or about 3-fold fewer red blood cells than that of a product obtained by using a density gradient centrifugation method.

139. The system of any one of embodiments 1 to 59 or the method of any one of embodiments 60 to 99, wherein a product is produced that comprises at least 3-fold or 10-fold fewer platelets than that of a product obtained by using a density gradient centrifugation method.

140. A population of cells produced by the system of any one of embodiments 1 to 59 or the method of any one of embodiments 60 to 99, wherein the population of cells exhibits an increase in one or more biological properties when compared to a population of cells produced by a density gradient centrifugation method wherein the one more biological properties are selected from the list consisting of: ability to readily integrate a lentiviral vector, ability to expand in culture, ability to retain T cell memory composition while in cell culture, receptivity to viral transduction, average telomere length, ability to retain a relative population of less differentiated naïve and central memory cells, functional killing capacity, IFN gamma expression, GM-CSF expression, TNF-a expression, and viability.

141. The population of cells of embodiment 140, wherein the population of cells exhibits at least about 25% increase in ability to readily integrate a lentiviral vector when compared to a population of cells produced by a density gradient centrifugation method.

142. The population of cells of embodiment 140, wherein the population of cells exhibits an increased ability to expand in culture, wherein the cells are expanded before or after being genetically modified when compared to a population of cells produced by a density gradient centrifugation method.

143. The population of cells of embodiment 142, wherein the population of cells exhibits at least about 1.5-fold increased ability to expand in culture when compared to a population of cells produced by a density gradient centrifugation method.

144. The population of cells of embodiment 140, wherein the population of cells exhibits an increased ability to retain T cell memory composition while in cell culture comprising retaining about the same T cell memory composition after at least 9 days in culture when compared to a population of cells produced by a density gradient centrifugation method.

145. The population of cells of embodiment 140, wherein the population of cells exhibits at least 30% increase in receptivity to viral transduction when compared to a population of cells produced by a density gradient centrifugation method.

146. The population of cells of embodiment 140, wherein the population of cells exhibits at least 30% increase in telomere length when compared to a population of cells produced by a density gradient centrifugation method.

147. The population of cells of embodiment 140, wherein the population of cells exhibits an increased ability to retain a relative population of less differentiated naïve and central memory cells while in cell culture comprising retaining about the same relative population of less differentiated naïve and central memory cells after at least 9 days in culture when compared to a population of cells produced by a density gradient centrifugation method.

148. The population of cells of embodiment 140, wherein the population of cells exhibits at least 30% increase in functional killing capacity when compared to a population of cells produced by a density gradient centrifugation method.

149. The population of cells of embodiment 140, wherein the population of cells exhibits at least 2-fold increase in IFN gamma expression after 9 days in culture when compared to a population of cells produced by a density gradient centrifugation method.

150. The population of cells of embodiment 140, wherein the population of cells exhibits at least 1.5-fold increase in GM-CSF expression after 9 days in culture when compared to a population of cells produced by a density gradient centrifugation method.

151. The population of cells of embodiment 140, wherein the population of cells exhibits at least 10% increase in TNF-a expression after 9 days in culture when compared to a population of cells produced by a density gradient centrifugation method.

152. The population of cells of embodiment 140, wherein the population of cells exhibits at least 10% increase in viability when compared to a population of cells produced by a density gradient centrifugation method.

153. A population of cells produced by the system of any one of embodiments 1 to 59 or the method of any one of embodiments 60 to 99, wherein the population of cells exhibits a decrease in one or more biological properties when compared to a population of cells produced by a density gradient centrifugation method wherein the one more biological properties are selected from the list consisting of: time required to expand in culture to produce a single therapeutic dose equivalent of cells, time required to express a gene delivered by a vector, relative population of effector or Temra cells, IL-1Ra expression, IL-6 expression, IL-13 expression, MCP-1 expression, PD1 and Tim3 co-expression, cell senescence or exhaustion, propensity to trigger cytokine release syndrome, and time in culture required before being delivered to a patient.

154. The population of cells of embodiment 153, wherein the population of cells exhibits at least decrease of 3 days of time required to expand in culture to produce a single therapeutic dose equivalent of cells when compared to a population of cells produced by a density gradient centrifugation method.

155. The population of cells of embodiment 153, wherein the population of cells exhibits at least decrease of 1 day of time required to express a gene delivered by a vector when compared to a population of cells produced by a density gradient centrifugation method.

156. The population of cells of embodiment 153, wherein the population of cells exhibits at least 10% decrease in relative population of effector or Temra cells when compared to a population of cells produced by a density gradient centrifugation method.

157. The population of cells of embodiment 153, wherein the population of cells exhibits at least 40% decrease in IL-1Ra expression after 13 days in culture when compared to a population of cells produced by a density gradient centrifugation method.

158. The population of cells of embodiment 153, wherein the population of cells exhibits at least 60% decrease in IL-6 expression after 13 days in culture when compared to a population of cells produced by a density gradient centrifugation method.

159. The population of cells of embodiment 153, wherein the population of cells exhibits at least 10% decrease of IL-13 expression when compared to a population of cells produced by a density gradient centrifugation method.

160. The population of cells of embodiment 153, wherein the population of cells exhibits at least 20% decrease of MCP-1 expression when compared to a population of cells produced by a density gradient centrifugation method.

161. The population of cells of embodiment 153, wherein the population of cells exhibits at least 50% decrease in PD1 and Tim3 co-expression when compared to a population of cells produced by a density gradient centrifugation method.

162. The population of cells of embodiment 153, wherein the population of cells exhibits at least 50% decrease in cell senescence or exhaustion when compared to a population of cells produced by a density gradient centrifugation method.

163. The population of cells of embodiment 153, wherein the population of cells exhibits at least 20% decreased propensity to trigger cytokine release syndrome when compared to a population of cells produced by a density gradient centrifugation method.

164. The population of cells of embodiment 153, wherein the population of cells exhibits at least 3 day decrease in time in culture required before being delivered to a patient.

165. The population of cells of any one of embodiments 140 to 164, wherein the exhibited increase or decrease of one or more biological properties when compared to a population of cells produced by a density gradient centrifugation method is apparent at least at about 0, 3, 6, 9, 13, or 16 days after being produced.

What is claimed is:

1. A system for generating a product enriched in one or more target particles from a sample, comprising:

a cassette to which one or more microfluidic cartridges are releasably coupled and supported, the cassette comprising a plurality of fluidic channels extending longitudinally and spaced apart on the cassette; and a plurality of pumps peristaltically coupled to the plurality of fluidic channels to control flow of fluidic content through the plurality of fluidic channels downstream to the one or more microfluidic cartridges for separation of the one or more target particles from the sample, without any moving parts from the pumps directly contacting the fluidic content during its flow, wherein the plurality of fluidic channels comprises an obstacle array configured to enrich the one or more target particles by deterministic lateral displacement.

2. The system of claim 1, wherein the plurality of fluidic channels comprises flexible tubing.

3. The system of claim 1, wherein each of the plurality of pumps comprises a set of pump heads that are peristaltically coupled to each subset of the plurality of fluidic channels.

4. The system of claim 3, wherein the set of pump heads in each pump comprises two or more pump heads.

5. The system of claim 4, wherein the two or more pump heads comprises two or more sets of rollers.

6. The system of claim 5, wherein each subset of the plurality of fluidic channels comprises two or more fluidic channels.

7. The system of claim 1, wherein the fluidic content comprises the sample, a media solution, a diluent, and waste that is generated by the one or more microfluidic cartridges after the one or more target particles have been separated from the sample.

8. The system of claim 7, wherein the fluidic content further comprises a priming solution.

9. The system of claim 7, wherein the fluidic content further comprises a recirculated solution comprising a concentrated amount of the one or more target particles.

10. The system of claim 7, wherein the plurality of pumps comprises a first pump for controlling a flow of the sample, a second pump for controlling a flow of the media solution, a third pump for controlling a flow of the diluent, and a fourth pump for controlling a flow of the waste.

11. The system of claim 7, wherein the plurality of pumps are individually controllable to modulate relative flowrates between the sample, the media solution, the diluent, and the waste.

12. The system of claim 3, wherein the set of pump heads in each pump are configured to actuate out-of-phase relative to each other.

13. The system of claim 12, wherein the set of pump heads in each pump actuate out-of-phase by less than or equal to about 180 degrees.

14. The system of claim 3, wherein the set of pump heads in each pump have a fixed motion relative to each other.

15. The system of claim 14, wherein the fixed motion comprises the set of pump heads in each pump moving at a same rate and in a same direction relative to each other.

16. The system of claim 3, wherein, for each pump and each subset of fluidic channels, the fluidic content transported by the set of pump heads is combined together at an outlet of each subset of fluidic channels into a single fluid path.

17. The system of claim 3, wherein a pulsatility of each pump is reduced by moving the set of pump heads out of phase.

18. The system of claim 11, wherein the plurality of pumps are individually controllable to (a) control a ratio of an amount of the waste relative to an amount of the sample, (b) control a ratio of an amount of the sample relative to an amount of the diluent, or (c) adjust a dilution factor.

19. The system of claim 1, wherein the plurality of pumps are individually controllable to be in phase or out of phase relative to each other.

20. The system of claim 1, wherein the plurality of pumps are individually controllable to achieve a same flow rate, different flow rates, a same flow direction, or different flow directions.

21. The system of claim 1, wherein the plurality of pumps are individually controllable to adjust the flow of the fluidic content in real-time as the one or more microfluidic cartridges are separating out the one or more target particles from the sample.

22. The system of claim 1, wherein the plurality of pumps are individually controllable to enable a desired concentration of the one or more target particles in the product.

23. The system of claim 1, wherein the plurality of pumps comprises peristaltic pumps.

* * * * *